(12) United States Patent
Moctezuma de la Barrera et al.

(10) Patent No.: US 12,102,365 B2
(45) Date of Patent: Oct. 1, 2024

(54) BONE PLATE FOR ATTACHING TO AN ANATOMIC STRUCTURE

(71) Applicant: MAKO Surgical Corp., Weston, FL (US)

(72) Inventors: José Luis Moctezuma de la Barrera, Freiburg (DE); Timothy Wade Perez, Plantation, FL (US); Donald W. Malackowski, Schoolcraft, MI (US); John R. Fossez, Plano, TX (US)

(73) Assignee: MAKO Surgical Corp., Weston, FL (US)

(*) Notice: Subject to any disclaimer, the term of this patent is extended or adjusted under 35 U.S.C. 154(b) by 0 days.

(21) Appl. No.: 18/109,886

(22) Filed: Feb. 15, 2023

(65) Prior Publication Data

US 2023/0190347 A1    Jun. 22, 2023

Related U.S. Application Data

(60) Continuation of application No. 17/165,220, filed on Feb. 2, 2021, now Pat. No. 11,622,800, which is a (Continued)

(51) Int. Cl.
*A61B 17/80* (2006.01)
*A61B 34/20* (2016.01)
(Continued)

(52) U.S. Cl.
CPC ........ *A61B 17/809* (2013.01); *A61B 17/8028* (2013.01); *A61B 17/8061* (2013.01);
(Continued)

(58) Field of Classification Search
CPC .......... A61B 2090/3983; A61B 17/809; A61B 17/8695; A61B 17/8028; A61B 2017/0641
See application file for complete search history.

(56) References Cited

U.S. PATENT DOCUMENTS 3,741,205 A    6/1973   Markoff et al.
4,362,416 A   12/1982   Kaimo
(Continued)

FOREIGN PATENT DOCUMENTS

CN    2587369 Y    11/2003
CN    1658789 A     8/2005
(Continued)

OTHER PUBLICATIONS

U.S. Appl. No. 18/076,446, filed Dec. 7, 2022.
(Continued)

*Primary Examiner* — Olivia C Chang
(74) *Attorney, Agent, or Firm* — Howard & Howard Attorneys PLLC

(57) ABSTRACT

A plate for attaching to an anatomic structure with fasteners. The plate has a body with a top surface and a bottom surface opposite the top surface. The body defines one or more openings to receive a respective one of the one or more fasteners. The bottom surface is concave to define a space to accommodate a portion of the anatomic structure. A bone pad surface extends from the bottom surface. A spike extends away from the bone pad surface. An extension arm can be coupled to the plate and the extension arm can support a tracking head to implement a surgical tracking assembly.

18 Claims, 34 Drawing Sheets

Related U.S. Application Data continuation of application No. 15/978,107, filed on May 12, 2018, now Pat. No. 10,932,837, which is a division of application No. 15/248,859, filed on Aug. 26, 2016, now Pat. No. 9,993,273, which is a continuation-in-part of application No. 14/156,856, filed on Jan. 16, 2014, now Pat. No. 9,566,120.

(60) Provisional application No. 62/341,886, filed on May 26, 2016, provisional application No. 61/753,219, filed on Jan. 16, 2013.

(51) Int. Cl.
*A61B 34/30* (2016.01)
*A61B 90/10* (2016.01)
*A61B 17/00* (2006.01)
*A61B 90/00* (2016.01)

(52) U.S. Cl.
CPC .............. *A61B 34/20* (2016.02); *A61B 34/30* (2016.02); *A61B 90/10* (2016.02); *A61B 2017/00119* (2013.01); *A61B 2034/2055* (2016.02); *A61B 2090/3983* (2016.02)

(56) References Cited

U.S. PATENT DOCUMENTS

| | | |
|---|---|---|
| 5,017,139 A | 5/1991 | Mushabac |
| 5,108,395 A | 4/1992 | Laurain |
| 5,108,397 A | 4/1992 | White |
| 5,142,930 A | 9/1992 | Allen et al. |
| 5,167,464 A | 12/1992 | Voellmer |
| 5,174,772 A | 12/1992 | Vranish |
| 5,368,593 A | 11/1994 | Stark |
| 5,566,681 A | 10/1996 | Manwaring et al. |
| 5,676,673 A | 10/1997 | Ferre et al. |
| 5,683,118 A | 11/1997 | Slocum |
| 5,748,827 A | 5/1998 | Holl et al. |
| 5,834,759 A | 11/1998 | Glossop |
| 5,855,582 A | 1/1999 | Gildenberg |
| 5,987,960 A | 11/1999 | Messner et al. |
| 6,021,343 A | 2/2000 | Foley et al. |
| 6,052,611 A | 4/2000 | Yanof et al. |
| 6,066,141 A | 5/2000 | Dall et al. |
| 6,167,145 A | 12/2000 | Foley et al. |
| 6,190,395 B1 | 2/2001 | Williams |
| 6,193,430 B1 | 2/2001 | Culpepper et al. |
| 6,203,543 B1 | 3/2001 | Glossop |
| 6,226,548 B1 | 5/2001 | Foley et al. |
| 6,273,896 B1 | 8/2001 | Franck et al. |
| 6,322,562 B1 | 11/2001 | Wolter |
| 6,327,491 B1 | 12/2001 | Franklin et al. |
| 6,377,011 B1 | 4/2002 | Ben-Ur |
| 6,379,071 B1 | 4/2002 | Sorvino |
| 6,430,434 B1 | 8/2002 | Mittelstadt |
| 6,434,507 B1 | 8/2002 | Clayton et al. |
| 6,484,049 B1 | 11/2002 | Seeley et al. |
| 6,491,699 B1 | 12/2002 | Henderson et al. |
| 6,514,259 B2 | 2/2003 | Picard et al. |
| 6,517,484 B1 | 2/2003 | Wilk et al. |
| 6,529,765 B1 | 3/2003 | Franck et al. |
| 6,572,624 B2 | 6/2003 | U et al. |
| 6,640,128 B2 | 10/2003 | Vilsmeier et al. |
| 6,719,757 B2 | 4/2004 | Neubauer et al. |
| 6,729,589 B2 | 5/2004 | Shelef |
| 6,738,657 B1 | 5/2004 | Franklin et al. |
| 6,746,172 B2 | 6/2004 | Culpepper |
| 6,856,828 B2 | 2/2005 | Cossette et al. |
| 6,893,447 B2 | 5/2005 | Dominguez et al. |
| 6,932,823 B2 | 8/2005 | Grimm et al. |
| 6,974,461 B1 | 12/2005 | Wolter |
| 6,980,849 B2 | 12/2005 | Sasso |
| 6,993,374 B2 | 1/2006 | Sasso |
| 7,043,961 B2 | 5/2006 | Pandey et al. |
| 7,048,741 B2 | 5/2006 | Swanson |
| 7,104,996 B2 | 9/2006 | Bonutti |
| 7,107,091 B2 | 9/2006 | Jutras et al. |
| 7,153,297 B2 | 12/2006 | Peterson |
| 7,153,308 B2 | 12/2006 | Peterson |
| 7,166,114 B2 | 1/2007 | Moctezuma De La Barrera et al. |
| 7,233,820 B2 | 6/2007 | Gilboa |
| 7,274,958 B2 | 9/2007 | Jutras et al. |
| 7,300,432 B2 | 11/2007 | Surma et al. |
| 7,302,288 B1 | 11/2007 | Schellengberg |
| 7,302,355 B2 | 11/2007 | Jansen et al. |
| 7,314,048 B2 | 1/2008 | Couture et al. |
| 7,366,561 B2 | 4/2008 | Mills et al. |
| 7,366,562 B2 | 4/2008 | Dukesherer et al. |
| 7,377,924 B2 | 5/2008 | Raistrick et al. |
| 7,419,492 B2 | 9/2008 | Yoon et al. |
| 7,458,977 B2 | 12/2008 | McGinley et al. |
| 7,477,926 B2 | 1/2009 | McCombs |
| 7,547,307 B2 | 6/2009 | Carson et al. |
| 7,558,617 B2 | 7/2009 | Vilsmeier |
| 7,604,639 B2 | 10/2009 | Swanson |
| 7,641,660 B2 | 1/2010 | Lakin et al. |
| 7,643,862 B2 | 1/2010 | Schoenefeld |
| 7,646,899 B2 | 1/2010 | Fitzpatrick |
| 7,668,584 B2 | 2/2010 | Jansen |
| 7,688,998 B2 | 3/2010 | Tuma et al. |
| 7,702,379 B2 | 4/2010 | Avinash et al. |
| 7,725,162 B2 | 5/2010 | Malackowski et al. |
| 7,725,182 B2 | 5/2010 | Sutardja |
| 7,726,564 B2 | 6/2010 | Goldbach |
| 7,734,327 B2 | 6/2010 | Colquhoun |
| 7,736,368 B2 | 6/2010 | Couture et al. |
| 7,753,910 B2 | 7/2010 | Ritland |
| 7,764,985 B2 | 7/2010 | McCombs et al. |
| 7,771,436 B2 | 8/2010 | Moctezuma de la Barrera et al. |
| 7,776,000 B2 | 8/2010 | Schaffrath et al. |
| 7,780,681 B2 | 8/2010 | Sarin et al. |
| 7,794,469 B2 | 9/2010 | Kao et al. |
| 7,835,778 B2 | 11/2010 | Foley et al. |
| 7,857,821 B2 | 12/2010 | Couture et al. |
| 7,862,570 B2 | 1/2011 | Russell et al. |
| 7,875,039 B2 | 1/2011 | Vohra et al. |
| 7,876,942 B2 | 1/2011 | Gilboa |
| 7,881,770 B2 | 2/2011 | Melkent et al. |
| 7,925,328 B2 | 4/2011 | Urquhart et al. |
| 7,951,176 B2 | 5/2011 | Grady et al. |
| 7,970,174 B2 | 6/2011 | Goldbach |
| 7,970,190 B2 | 6/2011 | Steinle et al. |
| 7,993,353 B2 | 8/2011 | Roeßner et al. |
| 7,996,059 B2 | 8/2011 | Porath et al. |
| 8,021,369 B2 | 9/2011 | Curry |
| 8,066,961 B2 | 11/2011 | Costello, III et al. |
| 8,105,339 B2 | 1/2012 | Melkent et al. |
| 8,109,877 B2 | 2/2012 | Moctezuma de la Barrera et al. |
| 8,114,134 B2 | 2/2012 | Winslow et al. |
| 8,147,496 B2 | 4/2012 | Couture et al. |
| 8,152,726 B2 | 4/2012 | Amiot et al. |
| 8,165,658 B2 | 4/2012 | Waynik et al. |
| 8,202,322 B2 | 6/2012 | Doty |
| 8,226,724 B2 | 7/2012 | Doty |
| 8,239,001 B2 | 8/2012 | Verard et al. |
| 8,271,069 B2 | 9/2012 | Jacob et al. |
| 8,277,505 B1 | 10/2012 | Doty |
| 8,348,954 B2 | 1/2013 | Carls et al. |
| 8,357,165 B2 | 1/2013 | Grant et al. |
| 8,382,766 B2 | 2/2013 | Warkentine et al. |
| 8,386,022 B2 | 2/2013 | Jutras et al. |
| 8,457,719 B2 | 6/2013 | Moctezuma de la Barrera et al. |
| 8,460,277 B2 | 6/2013 | Suarez et al. |
| 8,469,965 B2 | 6/2013 | Neubauer et al. |
| 8,512,346 B2 | 8/2013 | Couture |
| 8,535,329 B2 | 9/2013 | Sarin et al. |
| 8,549,732 B2 | 10/2013 | Burg et al. |
| 8,611,985 B2 | 12/2013 | Lavallee et al. |
| 8,644,570 B2 | 2/2014 | Hartmann et al. |
| 8,657,809 B2 | 2/2014 | Schoepp |
| 8,672,490 B2 | 3/2014 | Shafer et al. |
| 8,706,185 B2 | 4/2014 | Foley et al. |
| 8,709,017 B2 | 4/2014 | Pla ky et al. |

(56) References Cited

U.S. PATENT DOCUMENTS

| | | | |
|---|---|---|---|
| 8,721,660 B2 | 5/2014 | Ulfarsson et al. |
| 8,747,419 B2 | 6/2014 | Solar et al. |
| 8,800,939 B2 | 8/2014 | Karsak et al. |
| 8,820,729 B2 | 9/2014 | Doi et al. |
| 8,845,655 B2 | 9/2014 | Henderson et al. |
| 8,862,200 B2 | 10/2014 | Sherman et al. |
| 8,942,788 B2 | 1/2015 | Roger |
| 8,945,132 B2 | 2/2015 | Pla y et al. |
| 9,008,757 B2 | 4/2015 | Wu |
| 9,044,269 B2 | 6/2015 | Woerlein |
| 9,066,751 B2 | 6/2015 | Sasso |
| 9,082,319 B2 | 7/2015 | Shimada et al. |
| 9,085,401 B2 | 7/2015 | Shafer et al. |
| 9,095,376 B2 | 8/2015 | Pla ky et al. |
| 9,119,655 B2 | 9/2015 | Bowling et al. |
| 9,125,624 B2 | 9/2015 | Dekel et al. |
| 9,131,987 B2 | 9/2015 | Stefanchik et al. |
| 9,157,698 B2 | 10/2015 | Cosentino |
| 9,161,799 B2 | 10/2015 | Benson et al. |
| 9,381,085 B2 | 7/2016 | Axelson, Jr. et al. |
| 9,495,509 B2 | 11/2016 | Amiot et al. |
| 9,513,113 B2 | 12/2016 | Yang et al. |
| 9,566,120 B2 | 2/2017 | Malackowski et al. |
| 9,707,043 B2 | 7/2017 | Bozung |
| 9,827,052 B2 | 11/2017 | Fowler et al. |
| 9,993,273 B2 | 6/2018 | Moctezuma de la Barrera et al. |
| 10,531,925 B2 | 1/2020 | Malackowski et al. |
| 10,537,395 B2 | 1/2020 | Perez |
| 10,932,837 B2 | 3/2021 | Moctezuma De la Barrera et al. |
| 11,369,438 B2 | 6/2022 | Malackowski et al. |
| 11,559,358 B2 | 1/2023 | Perez |
| 2002/0133175 A1 | 9/2002 | Carson |
| 2002/0147450 A1* | 10/2002 | LeHuec .............. A61B 17/1728 |
| | | 606/280 |
| 2003/0069591 A1 | 4/2003 | Carson et al. |
| 2003/0078565 A1 | 4/2003 | Vilsmeier et al. |
| 2003/0086748 A1 | 5/2003 | Culpepper |
| 2003/0135213 A1 | 7/2003 | LeHuec et al. |
| 2003/0225329 A1 | 12/2003 | Rossner et al. |
| 2004/0068263 A1 | 4/2004 | Chouinard et al. |
| 2004/0127902 A1 | 7/2004 | Suzuki et al. |
| 2004/0171930 A1 | 9/2004 | Grimm et al. |
| 2005/0010226 A1 | 1/2005 | Grady, Jr. et al. |
| 2005/0049485 A1 | 3/2005 | Harmon et al. |
| 2005/0109855 A1 | 5/2005 | McCombs |
| 2005/0124988 A1 | 6/2005 | Terrill-Grisoni et al. |
| 2005/0137599 A1 | 6/2005 | Masini |
| 2005/0149050 A1 | 7/2005 | Stifter et al. |
| 2005/0187562 A1 | 8/2005 | Grimm et al. |
| 2005/0203528 A1 | 9/2005 | Couture et al. |
| 2005/0228387 A1 | 10/2005 | Paul |
| 2005/0277933 A1 | 12/2005 | Wall et al. |
| 2006/0015018 A1 | 1/2006 | Jutras et al. |
| 2006/0015119 A1 | 1/2006 | Plassky et al. |
| 2006/0052691 A1 | 3/2006 | Hall et al. |
| 2006/0052792 A1 | 3/2006 | Boettiger et al. |
| 2006/0100642 A1 | 5/2006 | Yang et al. |
| 2006/0142656 A1 | 6/2006 | Malackowski et al. |
| 2006/0161059 A1 | 7/2006 | Wilson |
| 2006/0195111 A1 | 8/2006 | Couture |
| 2006/0235290 A1 | 10/2006 | Gabriel et al. |
| 2006/0241405 A1 | 10/2006 | Leitner et al. |
| 2007/0016008 A1 | 1/2007 | Schoenefeld |
| 2007/0055232 A1 | 3/2007 | Colquhoun |
| 2007/0073133 A1 | 3/2007 | Schoenefeld |
| 2007/0073297 A1 | 3/2007 | Reynolds |
| 2007/0118139 A1 | 5/2007 | Cuellar et al. |
| 2007/0233156 A1 | 10/2007 | Metzger |
| 2007/0287910 A1 | 12/2007 | Stallings et al. |
| 2008/0027452 A1 | 1/2008 | Sheffer et al. |
| 2008/0045972 A1 | 2/2008 | Wanger et al. |
| 2008/0065084 A1 | 3/2008 | Couture et al. |
| 2008/0114375 A1 | 5/2008 | von Jako |
| 2008/0161682 A1 | 7/2008 | Kendrick et al. |
| 2008/0177173 A1 | 7/2008 | Deffenbaugh |
| 2008/0183108 A1 | 7/2008 | Huber et al. |
| 2008/0195110 A1 | 8/2008 | Plassy et al. |
| 2009/0024127 A1 | 1/2009 | Lechner et al. |
| 2009/0076553 A1 | 3/2009 | Wolter |
| 2009/0099445 A1 | 4/2009 | Burger |
| 2009/0118742 A1 | 5/2009 | Hartmann et al. |
| 2009/0163930 A1 | 6/2009 | Aoude et al. |
| 2009/0183740 A1 | 7/2009 | Sheffer et al. |
| 2009/0247863 A1 | 10/2009 | Proulx |
| 2009/0270928 A1 | 10/2009 | Stone et al. |
| 2009/0281417 A1 | 11/2009 | Hartmann et al. |
| 2009/0281421 A1 | 11/2009 | Culp et al. |
| 2009/0306499 A1 | 12/2009 | Van Vorhis et al. |
| 2010/0004259 A1 | 1/2010 | Liu et al. |
| 2010/0023062 A1 | 1/2010 | Faillace et al. |
| 2010/0042111 A1 | 2/2010 | Qureshi et al. |
| 2010/0063511 A1 | 3/2010 | Plassky et al. |
| 2010/0094358 A1 | 4/2010 | Moore et al. |
| 2010/0100131 A1 | 4/2010 | Wallenstein |
| 2010/0125286 A1 | 5/2010 | Wang et al. |
| 2010/0160932 A1 | 6/2010 | Gschwandtner et al. |
| 2010/0192961 A1 | 8/2010 | Amiot et al. |
| 2011/0004259 A1 | 1/2011 | Stallings et al. |
| 2011/0098553 A1 | 4/2011 | Robbins et al. |
| 2011/0160572 A1 | 6/2011 | McIntosh |
| 2011/0160738 A1 | 6/2011 | McIntosh |
| 2011/0166446 A1 | 7/2011 | Whitmore, III et al. |
| 2011/0263971 A1 | 10/2011 | Nikou et al. |
| 2012/0016427 A1 | 1/2012 | Stindel et al. |
| 2012/0109228 A1 | 5/2012 | Boyer et al. |
| 2012/0143048 A1 | 6/2012 | Finlay |
| 2012/0197266 A1 | 8/2012 | Sasso |
| 2013/0053648 A1 | 2/2013 | Abovitz et al. |
| 2013/0053895 A1 | 2/2013 | Stoll et al. |
| 2013/0060278 A1 | 3/2013 | Bozung et al. |
| 2013/0096573 A1 | 4/2013 | Kang et al. |
| 2013/0123580 A1 | 5/2013 | Peters et al. |
| 2013/0165947 A1 | 6/2013 | Nguyen et al. |
| 2013/0261783 A1 | 10/2013 | Daon et al. |
| 2013/0331686 A1 | 12/2013 | Freysinger et al. |
| 2013/0345718 A1 | 12/2013 | Crawford et al. |
| 2014/0039681 A1 | 2/2014 | Bowling et al. |
| 2014/0049629 A1 | 2/2014 | Siewerdsen et al. |
| 2014/0084809 A1 | 3/2014 | Catalano |
| 2014/0088410 A1 | 3/2014 | Wu |
| 2014/0200621 A1 | 7/2014 | Malackowski et al. |
| 2014/0236159 A1* | 8/2014 | Haider ............... A61B 17/1626 |
| | | 606/88 |
| 2014/0276943 A1 | 9/2014 | Bowling et al. |
| 2014/0364858 A1 | 12/2014 | Li et al. |
| 2015/0031982 A1 | 1/2015 | Piferi et al. |
| 2015/0088108 A1 | 3/2015 | Tyc et al. |
| 2015/0173911 A1 | 6/2015 | Doty |
| 2015/0182285 A1 | 7/2015 | Yen et al. |
| 2015/0182293 A1 | 7/2015 | Yang et al. |
| 2015/0209119 A1 | 7/2015 | Theodore et al. |
| 2015/0257851 A1 | 9/2015 | Plassky et al. |
| 2015/0265769 A1 | 9/2015 | Bratbak et al. |
| 2015/0282735 A1 | 10/2015 | Rossner |
| 2015/0309187 A1 | 10/2015 | Shafer et al. |
| 2016/0249988 A1 | 9/2016 | Pfeifer et al. |
| 2017/0034039 A1 | 2/2017 | Yadlapalli et al. |
| 2017/0119478 A1 | 5/2017 | Malackowski et al. |
| 2017/0245945 A1 | 8/2017 | Zuhars et al. |
| 2017/0333136 A1 | 11/2017 | Hladio et al. |
| 2017/0340395 A1 | 11/2017 | Perez |
| 2018/0263678 A1 | 9/2018 | Moctezuma De la Barrera et al. |
| 2019/0142525 A1 | 5/2019 | Malackowski et al. |
| 2020/0100849 A1 | 4/2020 | Malackowski et al. |
| 2020/0146756 A1 | 5/2020 | Perez |
| 2021/0153918 A1 | 5/2021 | Moctezuma de la Barrera et al. |
| 2022/0249176 A1 | 8/2022 | Malackowski et al. |

FOREIGN PATENT DOCUMENTS

| | | |
|---|---|---|
| CN | 101032426 A | 9/2007 |
| CN | 101311882 A | 11/2008 |
| CN | 101327148 A | 12/2008 |
| CN | 101536013 A | 9/2009 |

(56) References Cited

FOREIGN PATENT DOCUMENTS

| | | |
|---|---|---|
| CN | 102449666 A | 5/2012 |
| DE | 19629011 A1 | 1/1998 |
| DE | 4343117 C2 | 11/1999 |
| DE | 19962317 A1 | 3/2001 |
| DE | 10335388 B4 | 6/2006 |
| DE | 19858889 B4 | 8/2008 |
| EP | 1143867 B1 | 7/2002 |
| EP | 1211994 B1 | 4/2005 |
| EP | 1570802 A2 | 9/2005 |
| EP | 1211993 B1 | 10/2005 |
| EP | 1873666 A1 | 1/2008 |
| FR | 2435243 A1 | 4/1980 |
| JP | 2007503898 A | 3/2007 |
| JP | 2008538184 A | 10/2008 |
| JP | 2009511211 A | 3/2009 |
| JP | 2011515163 A | 5/2011 |
| WO | 02080773 A1 | 10/2002 |
| WO | 2004069073 A2 | 8/2004 |
| WO | 2004069073 A3 | 11/2004 |
| WO | 2005104783 A2 | 11/2005 |
| WO | 2006091494 A1 | 8/2006 |
| WO | 2007014470 A2 | 2/2007 |
| WO | 2007038135 A2 | 4/2007 |
| WO | 2008082574 A1 | 7/2008 |
| WO | 2008104548 A1 | 9/2008 |
| WO | 2008113008 A2 | 9/2008 |
| WO | 2008133615 A1 | 11/2008 |
| WO | 2009117832 A1 | 10/2009 |
| WO | 2010055193 A1 | 5/2010 |
| WO | 2010111090 A1 | 9/2010 |
| WO | 2012103407 A1 | 8/2012 |
| WO | 2012127353 A1 | 9/2012 |
| WO | 2013091112 A1 | 6/2013 |
| WO | 2013177334 A1 | 11/2013 |
| WO | 2013192598 A1 | 12/2013 |
| WO | 2014091053 A1 | 6/2014 |
| WO | 2014139022 A1 | 9/2014 |
| WO | 2014198784 A1 | 12/2014 |
| WO | 2015013518 A1 | 1/2015 |
| WO | 2015067743 A2 | 5/2015 |
| WO | 2015090434 A1 | 6/2015 |
| WO | 2015150877 A1 | 10/2015 |

OTHER PUBLICATIONS

English language abstract and machine-assisted English translation for CN 101311882 A extracted from espacenet.com database on Feb. 14, 2022, 17 pages.

English language abstract and machine-assisted English translation for CN 101327148 A extracted from espacenet.com database on Feb. 14, 2022, 13 pages.

English language abstract and machine-assisted English translation for CN 2587369 extracted from espacenet.com database on Jun. 13, 2018, 13 pages.

English language abstract and machine-assisted English translation for DE 103 35 388 extracted from espacenet.com database on Oct. 11, 2017, 14 pages.

English language abstract and machine-assisted English translation for DE 19629011 extracted from espacenet.com database on Jan. 12, 2017; 7 pages.

English language abstract and machine-assisted English translation for DE 19858889 extracted from espacenet.com database on Jan. 12, 2017; 13 pages.

English language abstract and machine-assisted English translation for DE 4343117 extracted from espacenet.com database on Jan. 12, 2017; 7 pages.

English language abstract and machine-assisted English translation for FR 2 435 243 A1 extracted from the www.espacenet.com database on Jul. 31, 2022, 4 pages.

English language abstract and machine-assisted English translation for WO 2008/104548 extracted from espacenet.com database on Oct. 12, 2017, 20 pages.

English language abstract and machine-assisted translation of JP2011515163 extracted from espacenet.com on Jan. 29, 2018; 22 pages.

English language abstract for CN 101032426 A extracted from espacenet.com database on Mar. 29, 2021, 1 page.

English language abstract for CN 101536013 A extracted from espacenet.com database on Mar. 29, 2021, 2 pages.

English language abstract for CN 10244966 A extracted from espacenet.com database on Mar. 29, 2021, 2 pages.

English language abstract for CN 1658789 A extracted from espacenet.com database on Mar. 29, 2021, 1 page.

English language abstract for DE 19 962 317 A1 extracted from espacenet.com database on Aug. 11, 2022, 1 page.

English language abstract for EP 1 873 666 A1 extracted from the www.espacenet.com database on Dec. 12, 2018.

English language abstract for FR 2435243 extracted from espacenet.com database on Dec. 16, 2016; 2 pages.

English language abstract for JP 2007 503898 A extracted from the www.espacenet.com database on May 2, 2014.

English language abstract for JP 2008-538184 extracted from espacenet.com database on Jun. 18, 2018, 2 pages.

English language abstract for JP 2009 511211 A extracted from the www.espacenet.com database on May 2, 2014.

English language abstract for JP 2011-515163 extracted from espacenet.com database on Jun. 18, 2018, 2 pages.

English language abstract for WO 2014/091053 and machine-assisted English translation for equivalent ES 2477140 of WO 2014/091053 extracted from espacenet.com database on Oct. 26, 2017, 10 pages.

English language abstract for WO 2015/067743 extracted from espacenet.com database on Oct. 12, 2017, 2 pages.

International Search Report for Application No. PCT/US2014/011821 dated Jul. 18, 2014; 7 pages.

Liebergall, Meier et al., "Computer-Aided Orthopaedic Surgery in Skeletal Trama", Rockwood & Green's Fractures in Adults, 6th Edition, 2006 Lippincott Williams & Wilkins, pp. 739-767; 60 pages.

U.S. Appl. No. 16/701,972, filed Dec. 3, 2019.

Written Opinion for Application No. PCT/US2014/011821 dated Jul. 18, 2014; 10 pages.

* cited by examiner

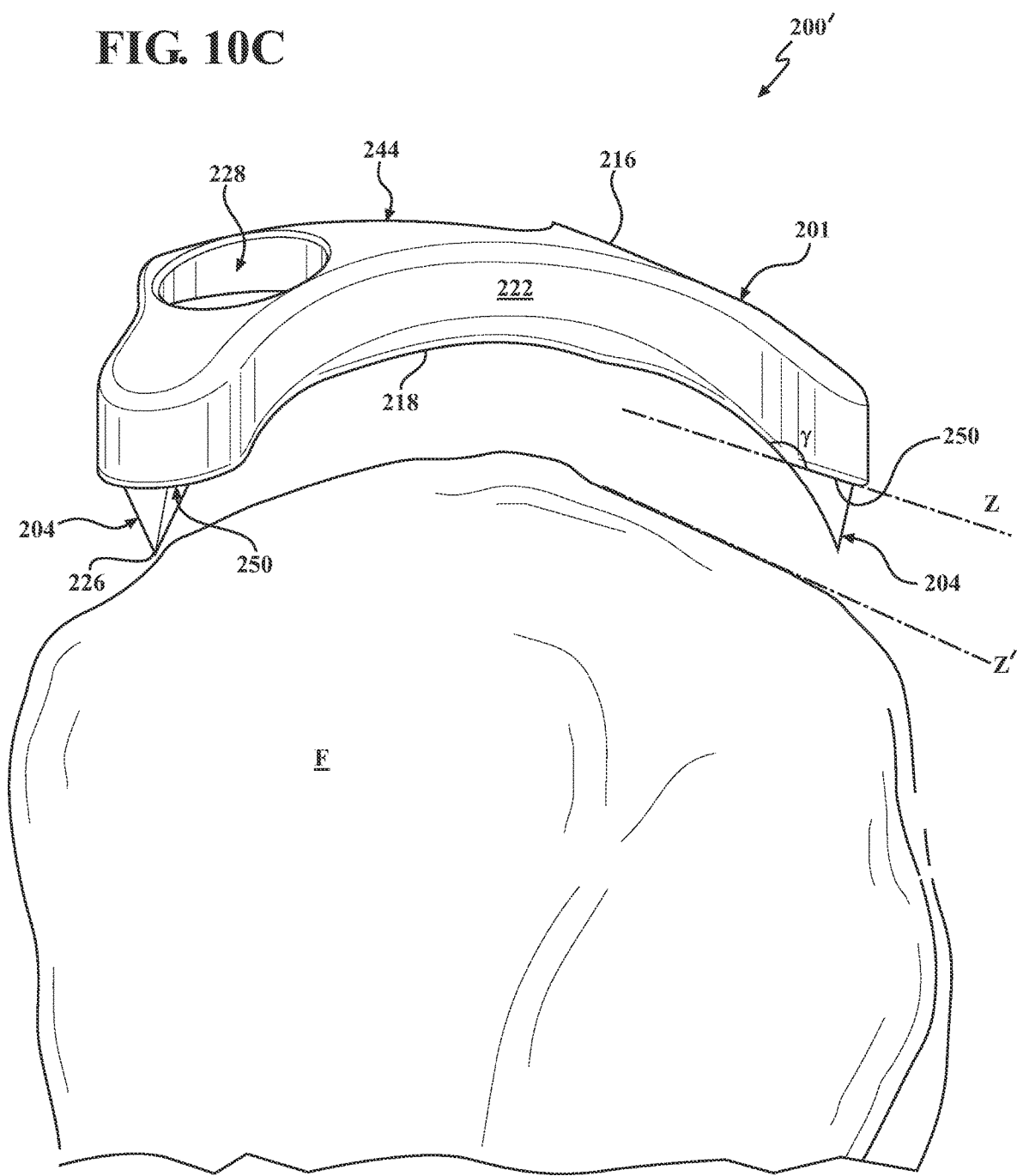

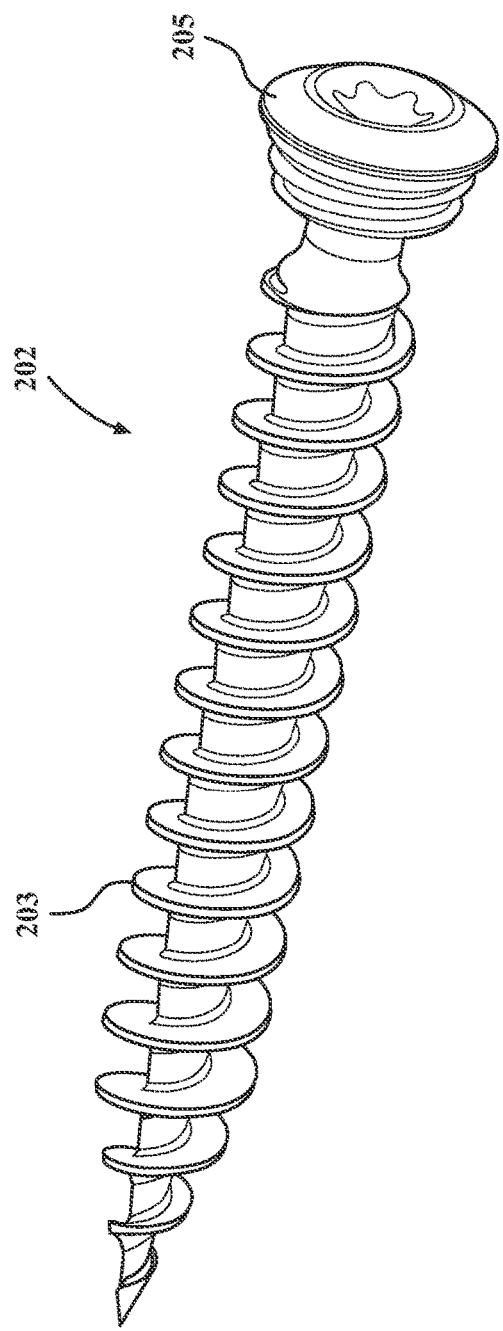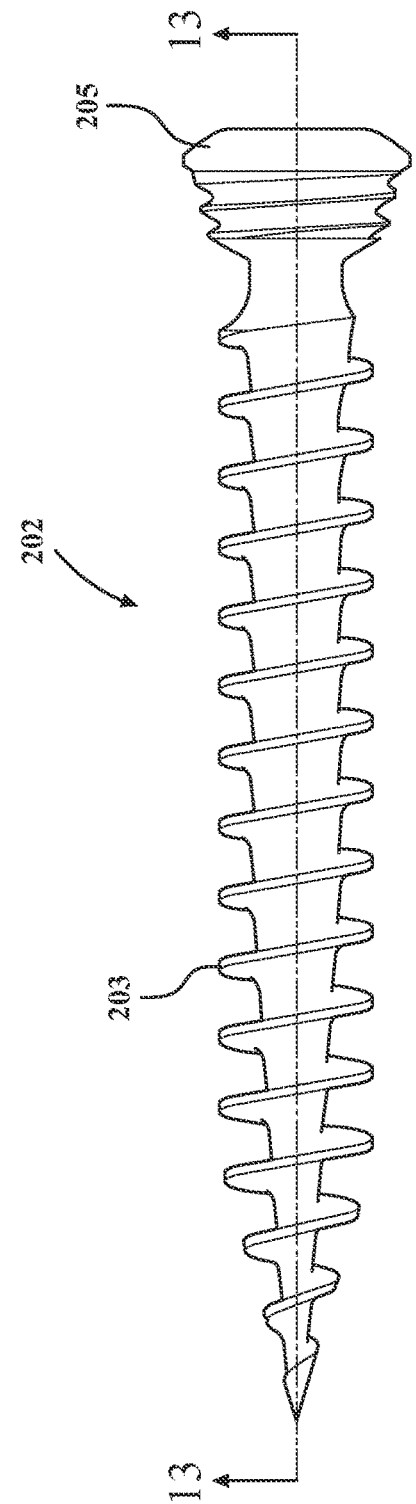
FIG. 11
FIG. 12

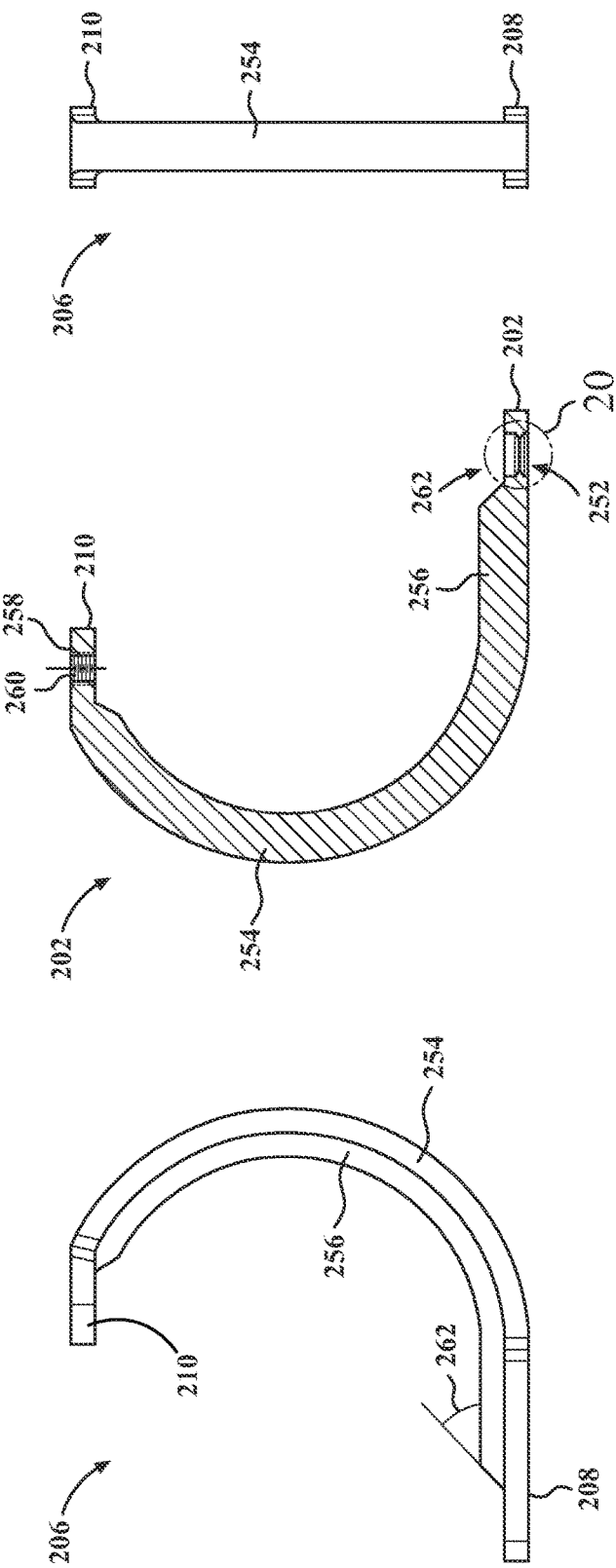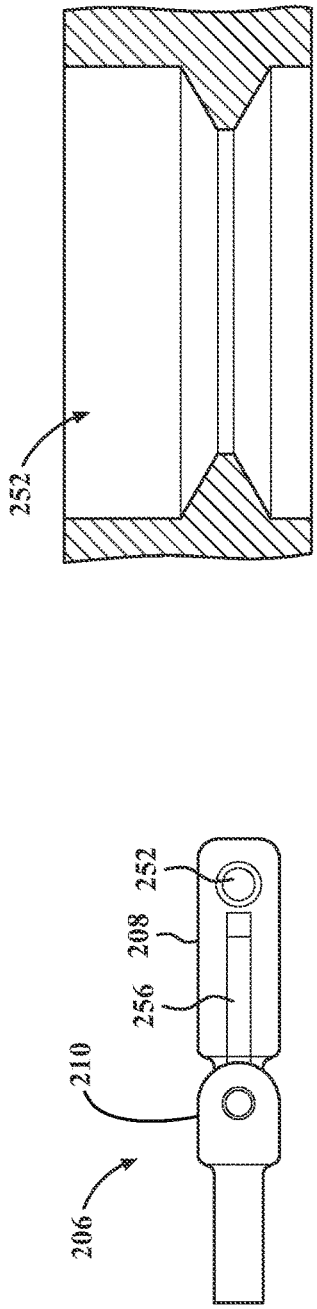
FIG. 16
FIG. 17
FIG. 18
FIG. 19
FIG. 20

BONE PLATE FOR ATTACHING TO AN ANATOMIC STRUCTURE

CROSS-REFERENCE TO RELATED APPLICATIONS

The subject application is a continuation of U.S. patent application Ser. No. 17/165,220, filed Feb. 2, 2021, which is a continuation of U.S. patent application Ser. No. 15/978,107, filed May 12, 2018, now U.S. Pat. No. 10,932,837, which is a divisional of U.S. patent application Ser. No. 15/248,859, filed on Aug. 26, 2016, now U.S. Pat. No. 9,993,273, which is a continuation-in-part application of U.S. patent application Ser. No. 14/156,856, filed on Jan. 16, 2014, now U.S. Pat. No. 9,566,120, which claims priority to and the benefit of U.S. Provisional Patent App. No. 61/753,219, filed on Jan. 16, 2013.

U.S. patent application Ser. No. 15/248,859 also claims priority to and the benefit of U.S. Provisional Patent App. No. 62/341,886, filed on May 26, 2016. The entire contents of each of the aforementioned applications are hereby incorporated by reference.

TECHNICAL FIELD

The disclosure relates generally to bone plates and tracking devices employing bone plates for attaching to a patient anatomy.

BACKGROUND

Navigation systems assist users in locating objects. Navigation systems may employ light signals, sound waves, magnetic fields, radio frequency signals, etc. in order to track the position and/or orientation of objects. A localizer cooperates with tracking elements on tracking devices to ultimately determine a position and orientation of the objects. Navigation systems are often used in industrial, aerospace, defense, and medical applications. In the medical field, navigation systems assist surgeons in placing surgical instruments relative to a patient's anatomy. Exemplary surgeries in which navigation systems are used include neurosurgery and orthopedic surgery.

Often the surgical navigation system includes attaching the tracking device to an anatomic object, typically bony anatomy, with a bone screw or other suitable fastener. Once secured to the bony anatomy, and particularly after the tracking device is registered with the localizer, it is essential that the tracking device does not move relative to the anatomy. Misalignment due to movement of the tracking device relative to the anatomy can require recalibration or re-registration of the tracking device, or if unnoticed, can result in serious consequences during the surgical procedure, including inadvertent collision with critical anatomic structures, suboptimally located surgical hardware, and the like.

A bone plate is often secured to the bony anatomy through overlying soft tissue such as skin, fat, muscle, and vascular structures, after which the tracking device is coupled to the bone plate. The soft tissues between the bone plate and the bony anatomy can endure appreciable compressive forces, resulting in possible surgical complication and/or delayed recovery.

Therefore, a need exists in the art for a tracking device designed to overcome one or more of the aforementioned disadvantages.

SUMMARY

According to a first aspect, a plate is provided for attaching to an anatomic structure with one or more fasteners, the plate comprising: a body comprising a top surface, and a bottom surface opposite the top surface, the body defining one or more openings configured to receive a respective one of the one or more fasteners, wherein the bottom surface is concave to define a space configured to accommodate a portion of the anatomic structure; a bone pad surface extending from the bottom surface; and a spike extending away from the bone pad surface.

According to a second aspect, a surgical tracking assembly is provided, comprising: a tracking head; an extension arm comprising a mounting end and a base end, and the tracking head being coupled to the extension arm at the mounting end; and a plate coupled to the extension arm at the base end, the plate configured for attachment to an anatomic structure with one or more fasteners, the plate comprising: a body comprising a top surface, and a bottom surface opposite the top surface, the body defining one or more openings configured to receive a respective one of the one or more fasteners, wherein the bottom surface is concave to define a space configured to accommodate a portion of the anatomic structure; a bone pad surface extending from the bottom surface; and a spike extending away from the bone pad surface.

BRIEF DESCRIPTION OF THE DRAWINGS

Advantages of the present disclosure will be readily appreciated as the same becomes better understood by reference to the following detailed description when considered in connection with the accompanying drawings wherein:

FIG. 10C is an elevational view of the bone plate of FIG. 10A positioned proximate to the bone;

FIG. 11 is a perspective view of a bone screw;

FIG. 12 is an elevational view of the bone screw;

FIG. 16 is an elevational view of an extension arm;

FIG. 17 is a cross-sectional view of the extension arm taken down the center of the extension arm;

FIG. 18 is a rear view of the extension arm;

FIG. 19 is a top view of the extension arm;

FIG. 20 is a blown-up view from FIG. 17;

DETAILED DESCRIPTION

Figure 1:
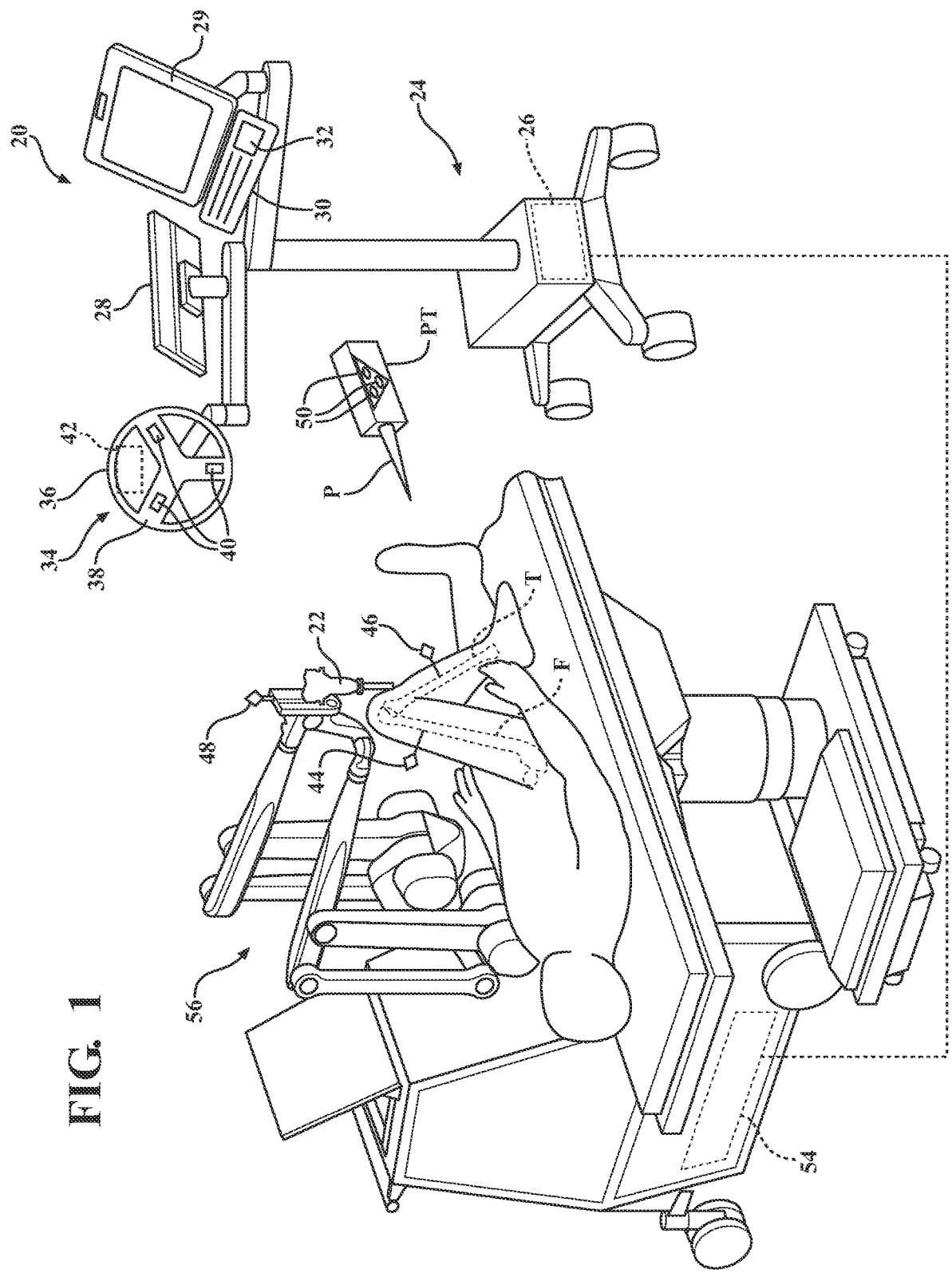
FIG. 1 is a perspective view of a navigation system of the present disclosure being used in conjunction with a robotic manipulator.

Referring to FIG. 1 a navigation system 20 is illustrated. The navigation system 20 is shown in a surgical setting such as an operating room of a medical facility. The navigation system 20 is set up to track movement of various objects in the operating room. Such objects include, for example, a surgical instrument 22, a femur F of a patient, and a tibia T of the patient. The navigation system 20 tracks these objects for purposes of displaying their relative positions and orientations to the surgeon and, in some cases, for purposes of controlling or constraining movement of the surgical instrument 22 relative to a predefined path or anatomical boundary.

The navigation system 20 includes a computer cart assembly 24 that houses a navigation computer 26. A navigation interface is in operative communication with the navigation computer 26. The navigation interface includes a first display 28 adapted to be situated outside of a sterile field and a second display 29 adapted to be situated inside the sterile field. The displays 28, 29 are adjustably mounted to the computer cart assembly 24. First and second input devices 30, 32 such as a mouse and keyboard can be used to input information into the navigation computer 26 or otherwise select/control certain aspects of the navigation computer 26. Other input devices are contemplated including a touch screen (not shown) on displays 28, 29 or voice-activation.

A localizer 34 communicates with the navigation computer 26. In the embodiment shown, the localizer 34 is an optical localizer and includes a camera unit 36 (also referred to as a sensing device). The camera unit 36 has an outer casing 38 that houses one or more optical position sensors 40. In some embodiments at least two optical sensors 40 are employed, preferably three. The optical sensors 40 may be three separate charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Camera unit 36 is mounted on an adjustable arm to position the optical sensors 40 with a field of view of the below discussed trackers that, ideally, is free from obstructions.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation computer 26.

Position and orientation signals and/or data are transmitted to the navigation computer 26 for purposes of tracking the objects. The computer cart assembly 24, display 28, and camera unit 36 may be like those described in U.S. Pat. No. 7,725,162 to Malackowski, et al. issued on May 25, 2010, entitled "Surgery System", hereby incorporated by reference.

The navigation computer 26 can be a personal computer or laptop computer. Navigation computer 26 has the displays 28, 29, central processing unit (CPU) and/or other processors, memory (not shown), and storage (not shown). The navigation computer 26 is loaded with software as described below. The software converts the signals received from the camera unit 36 into data representative of the position and orientation of the objects being tracked.

Navigation system 20 includes a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Other methods of attachment are described further below. In additional embodiments, a tracker (not shown) is attached to the patella to track a position and orientation of the patella. In yet further embodiments, the trackers 44, 46 could be mounted to other tissue types or parts of the anatomy.

An instrument tracker 48 is firmly attached to the surgical instrument 22. The instrument tracker 48 may be integrated into the surgical instrument 22 during manufacture or may be separately mounted to the surgical instrument 22 in preparation for the surgical procedures. The working end of the surgical instrument 22, which is being tracked, may be a rotating bur, electrical ablation device, or the like.

The trackers 44, 46, 48 can be battery powered with an internal battery or may have leads to receive power through the navigation computer 26, which, like the camera unit 36, preferably receives external power.

In the embodiment shown, the surgical instrument 22 is an end effector of a surgical manipulator. Such an arrangement is shown in U.S. patent application Ser. No. 13/958,070, filed Aug. 2, 2013, entitled, "Surgical Manipulator Capable of Controlling a Surgical Instrument in Multiple Modes", the disclosure of which is hereby incorporated by reference.

In other embodiments, the surgical instrument 22 may be manually positioned by only the hand of the user, without the aid of any cutting guide, jib, or other constraining mechanism such as a manipulator or robot. Such a surgical instrument is described in U.S. patent application Ser. No. 13/600,888, filed Aug. 31, 2012, entitled, "Surgical Instrument Including Housing, a Cutting Accessory that Extends from the Housing and Actuators that Establish the Position of the Cutting Accessory Relative to the Housing", the disclosure of which is hereby incorporated by reference.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers 50 for transmitting light signals to the optical sensors 40. The active markers 50 can be, for example, light emitting diodes (LEDs) 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 1000 Hz. The sampling rate is the rate at which the optical sensors 40 receive light signals from sequentially fired LEDs 50. In some embodiments, the light signals from the LEDs 50 are fired at different rates for each tracker 44, 46, 48.

Figure 2:
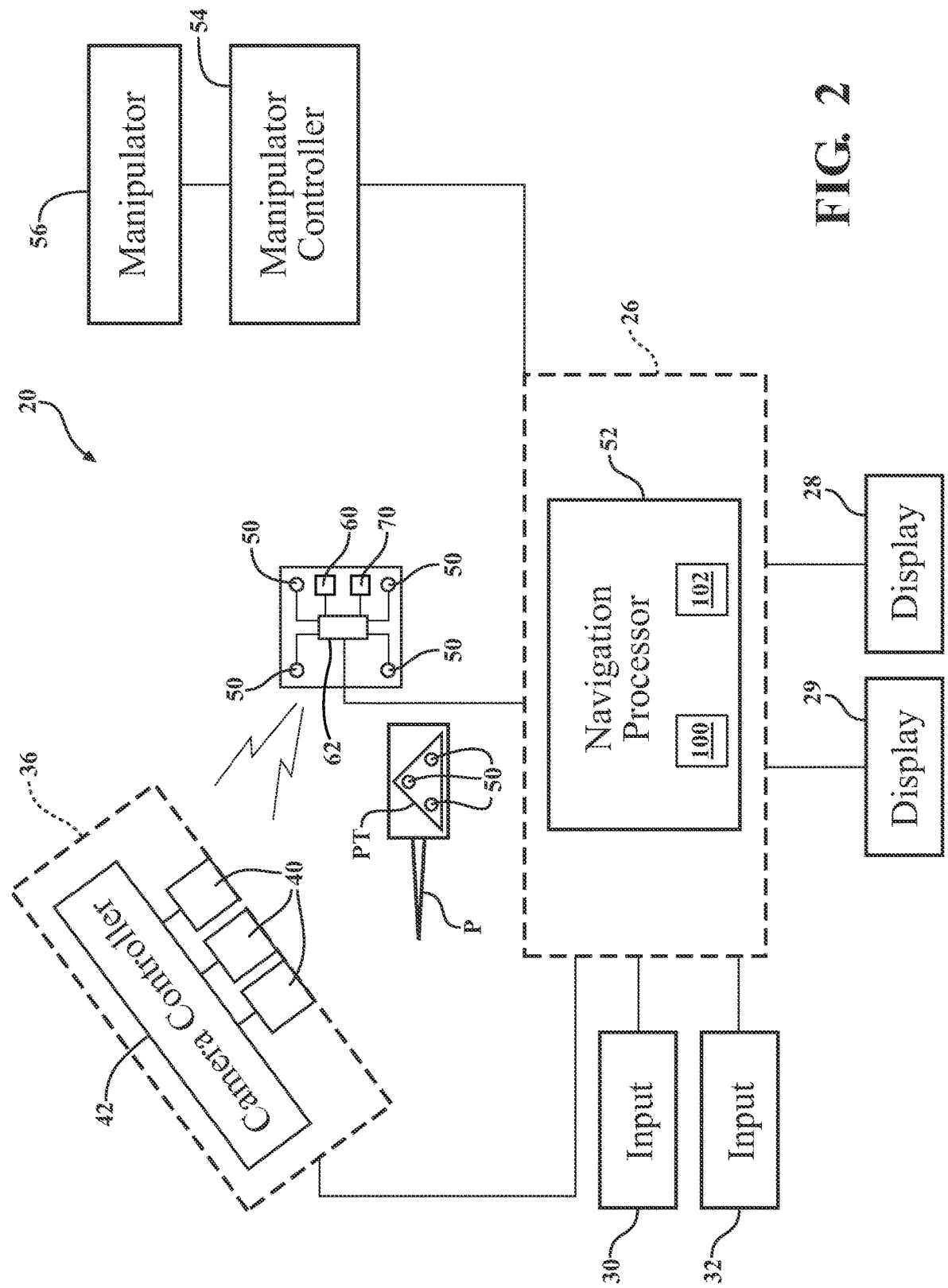
FIG. 2 is a schematic view of the navigation system.

Referring to FIG. 2, each of the LEDs 50 are connected to a tracker controller 62 located in a housing (not shown) of the associated tracker 44, 46, 48 that transmits/receives data to/from the navigation computer 26. In one embodiment, the tracker controllers 62 transmit data on the order of several Megabytes/second through wired connections with the navigation computer 26. In other embodiments, a wireless connection may be used. In these embodiments, the navigation computer 26 has a transceiver (not shown) to receive the data from the tracker controller 62.

In other embodiments, the trackers 44, 46, 48 may have passive markers (not shown), such as reflectors that reflect light emitted from the camera unit 36. The reflected light is then received by the optical sensors 40. Active and passive marker arrangements are well known in the art.

Each of the trackers 44, 46, 48 also includes a 3-dimensional gyroscope sensor 60 that measures angular velocities of the trackers 44, 46, 48. As is well known to those skilled in the art, the gyroscope sensors 60 output readings indicative of the angular velocities relative to x, y, and z axes of a gyroscope coordinate system. These readings are multiplied by a conversion constant defined by the manufacturer to obtain measurements in degrees/second with respect to each of the x, y, and z axes of the gyroscope coordinate system. These measurements can then be converted to an angular velocity vector defined in radians/second.

The angular velocities measured by the gyroscope sensors 60 provide additional non-optically based kinematic data for the navigation system 20 with which to track the trackers 44, 46, 48. The gyroscope sensors 60 may be oriented along the axis of each coordinate system of the trackers 44, 46, 48. In other embodiments, each gyroscope coordinate system is transformed to its tracker coordinate system such that the gyroscope data reflects the angular velocities with respect to the x, y, and z axes of the coordinate systems of the trackers 44, 46, 48.

Each of the trackers 44, 46, 48 also includes a 3-axis accelerometer 70 that measures acceleration along each of x, y, and z axes of an accelerometer coordinate system. The accelerometers 70 provide additional non-optically based data for the navigation system 20 with which to track the trackers 44, 46, 48.

The accelerometers 70 may be oriented along the axis of each coordinate system of the trackers 44, 46, 48. In other embodiments, each accelerometer coordinate system is transformed to its tracker coordinate system such that the accelerometer data reflects the accelerations with respect to the x, y, and z axes of the coordinate systems of the trackers 44, 46, 48.

Each of the gyroscope sensors 60 and accelerometers 70 communicate with the tracker controller 62 located in the housing of the associated tracker that transmits/receives data to/from the navigation computer 26. The data can be received either through a wired or wireless connection.

The navigation computer 26 includes a navigation processor 52. The camera unit 36 receives optical signals from the LEDs 50 of the trackers 44, 46, 48 and outputs to the processor 52 signals and/or data relating to the position of the LEDs 50 of the trackers 44, 46, 48 relative to the localizer 34. The gyroscope sensors 60 transmit non-optical signals to the processor 52 relating to the 3-dimensional angular velocities measured by the gyroscope sensors 60. Based on the received optical and non-optical signals, navigation processor 52 generates data indicating the relative positions and orientations of the trackers 44, 46, 48 relative to the localizer 34.

It should be understood that the navigation processor 52 could include one or more processors to control operation of the navigation computer 26. The processors can be any type of microprocessor or multi-processor system. The term processor is not intended to be limited to a single processor.

Prior to the start of the surgical procedure, additional data are loaded into the navigation processor 52. Based on the position and orientation of the trackers 44, 46, 48 and the previously loaded data, navigation processor 52 determines the position of the working end of the surgical instrument 22 and the orientation of the surgical instrument 22 relative to the tissue against which the working end is to be applied. In some embodiments, navigation processor 52 forwards these data to a manipulator controller 54. The manipulator controller 54 can then use the data to control a robotic manipulator 56 as described in U.S. patent application Ser. No. 13/958,070, filed Aug. 2, 2013, entitled, "Surgical Manipulator Capable of Controlling a Surgical Instrument in Multiple Modes", the disclosure of which is hereby incorporated by reference.

The navigation processor 52 also generates image signals that indicate the relative position of the surgical instrument working end to the surgical site. These image signals are applied to the displays 28, 29. Displays 28, 29, based on these signals, generate images that allow the surgeon and staff to view the relative position of the surgical instrument working end to the surgical site. The displays, 28, 29, as discussed above, may include a touch screen or other input/output device that allows entry of commands.

Figure 3:
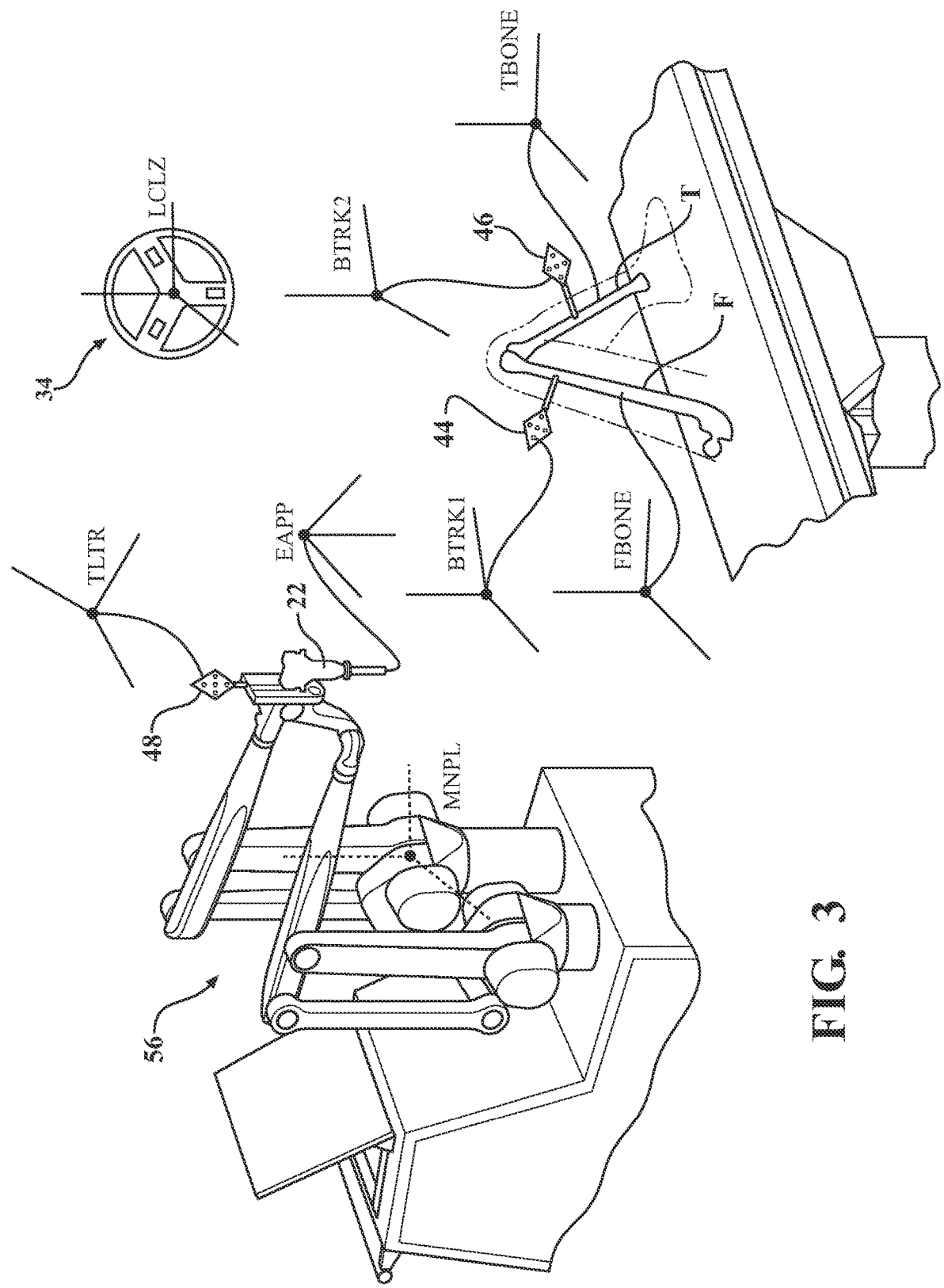
FIG. 3 is schematic view of the coordinates systems used in the navigation system.

Referring to FIG. 3, tracking of objects is generally conducted with reference to a localizer coordinate system LCLZ. The localizer coordinate system has an origin and an orientation (a set of x, y, and z axes).

Each tracker 44, 46, 48 and object being tracked also has its own coordinate system separate from localizer coordinate system LCLZ. Components of the navigation system 20 that have their own coordinate systems are the bone trackers 44, 46 and the instrument tracker 48. These coordinate systems are represented as, respectively, bone tracker coordinate systems BTRK1, BTRK2, and instrument tracker coordinate system TLTR.

Navigation system 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the procedure, pre-operative images of the femur F and tibia T are generated (or of other tissues in other embodiments). These images may be based on magnetic resonance imaging (MRI) scans, radiological scans or computed tomography (CT) scans of the patient's anatomy. These images are mapped to the femur coordinate system FBONE and tibia coordinate system TBONE using well known methods in the art. In one embodiment, a pointer instrument P, such as disclosed in U.S. Pat. No. 7,725,162 to Malackowski, et al., hereby incorporated by reference, having its own tracker PT (see FIG. 2), may be used to map the femur coordinate system FBONE and tibia coordinate system TBONE to the pre-operative images. These images are fixed in the femur coordinate system FBONE and tibia coordinate system TBONE.

During the initial phase of the procedure, the bone trackers 44, 46 are firmly affixed to the bones of the patient. The pose (position and orientation) of coordinate systems FBONE and TBONE are mapped to coordinate systems BTRK1 and BTRK2, respectively. Given the fixed relationship between the bones and their bone trackers 44, 46, the pose of coordinate systems FBONE and TBONE remain fixed relative to coordinate systems BTRK1 and BTRK2, respectively, throughout the procedure. The pose-describing data are stored in memory integral with both manipulator controller 54 and navigation processor 52.

The working end of the surgical instrument 22 (also referred to as energy applicator distal end) has its own coordinate system EAPP. The origin of the coordinate system EAPP may represent a centroid of a surgical cutting bur, for example. The pose of coordinate system EAPP is fixed to the pose of instrument tracker coordinate system TLTR before the procedure begins. Accordingly, the poses of these coordinate systems EAPP, TLTR relative to each other are determined. The pose-describing data are stored in memory integral with both manipulator controller 54 and navigation processor 52.

Referring to FIG. 2, a localization engine 100 is a software module that can be considered part of the navigation system 20. Components of the localization engine 100 run on navigation processor 52. In some versions, the localization engine 100 may run on the manipulator controller 54.

Localization engine 100 receives as inputs the optically-based signals from the camera controller 42 and the non-optically based signals from the tracker controller 62. Based on these signals, localization engine 100 determines the pose of the bone tracker coordinate systems BTRK1 and BTRK2 in the localizer coordinate system LCLZ. Based on the same signals received for the instrument tracker 48, the localization engine 100 determines the pose of the instrument tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the patient trackers 44, 46. Coordinate transformer 102 also stores the data indicating the pose of the working end of the surgical instrument 22 relative to the instrument tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of both the coordinate system EAPP, and the bone coordinate systems, FBONE and TBONE to the localizer coordinate system LCLZ.

As a result, coordinate transformer 102 generates data indicating the position and orientation of the working end of the surgical instrument 22 relative to the tissue (e.g., bone) against which the instrument working end is applied. Image signals representative of these data are forwarded to displays 28, 29 enabling the surgeon and staff to view this information. In certain embodiments, other signals representative of these data can be forwarded to the manipulator controller 54 to control the manipulator 56 and corresponding movement of the surgical instrument 22.

Steps for determining the pose of each of the tracker coordinate systems BTRK1, BTRK2, TLTR in the localizer coordinate system LCLZ and systems and methods for determining the pose of the trackers 44, 46, 48 and the corresponding poses of the surgical instrument 22 with respect to the femur F and tibia T are described in greater detail in U.S. patent application Ser. No. 14/035,207, filed Sep. 24, 2013, entitled "Navigation System Including Optical and Non-Optical Sensors", the disclosure of which is hereby incorporated by reference.

In some embodiments, only one LED 50 can be read by the optical sensors 40 at a time. The camera controller 42, through one or more infrared or RF transceivers (on camera unit 36 and trackers 44, 46, 48), or through a wired connection, may control the firing of the LEDs 50, as described in U.S. Pat. No. 7,725,162 to Malackowski, et al., hereby incorporated by reference. Alternatively, the trackers 44, 46, 48 may be activated locally (such as by a switch on trackers 44, 46, 48) which then fires its LEDs 50 sequentially once activated, without instruction from the camera controller 42.

Figure 4:
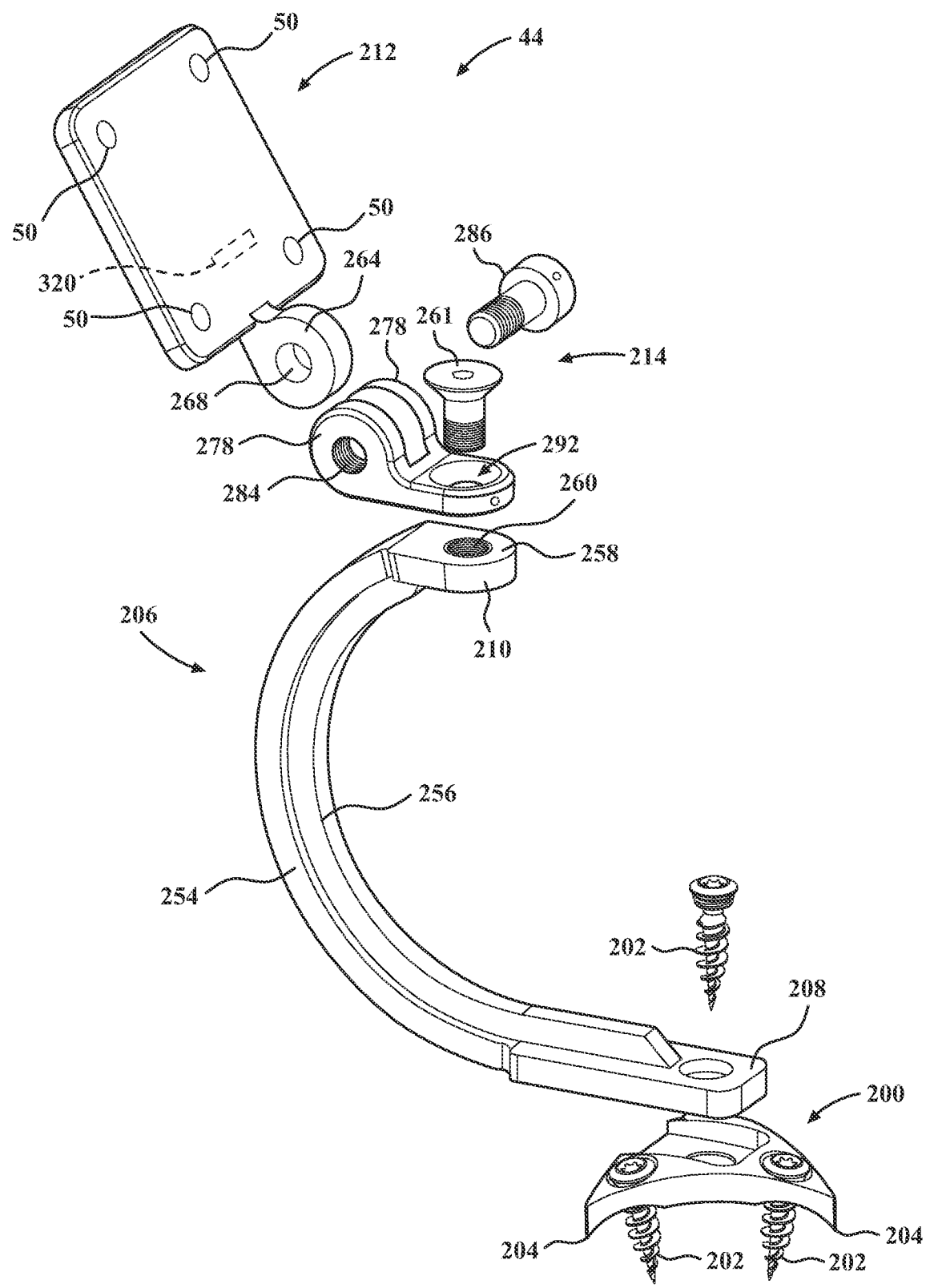
FIG. 4 is an exploded view of a tracking device.
Figure 5:
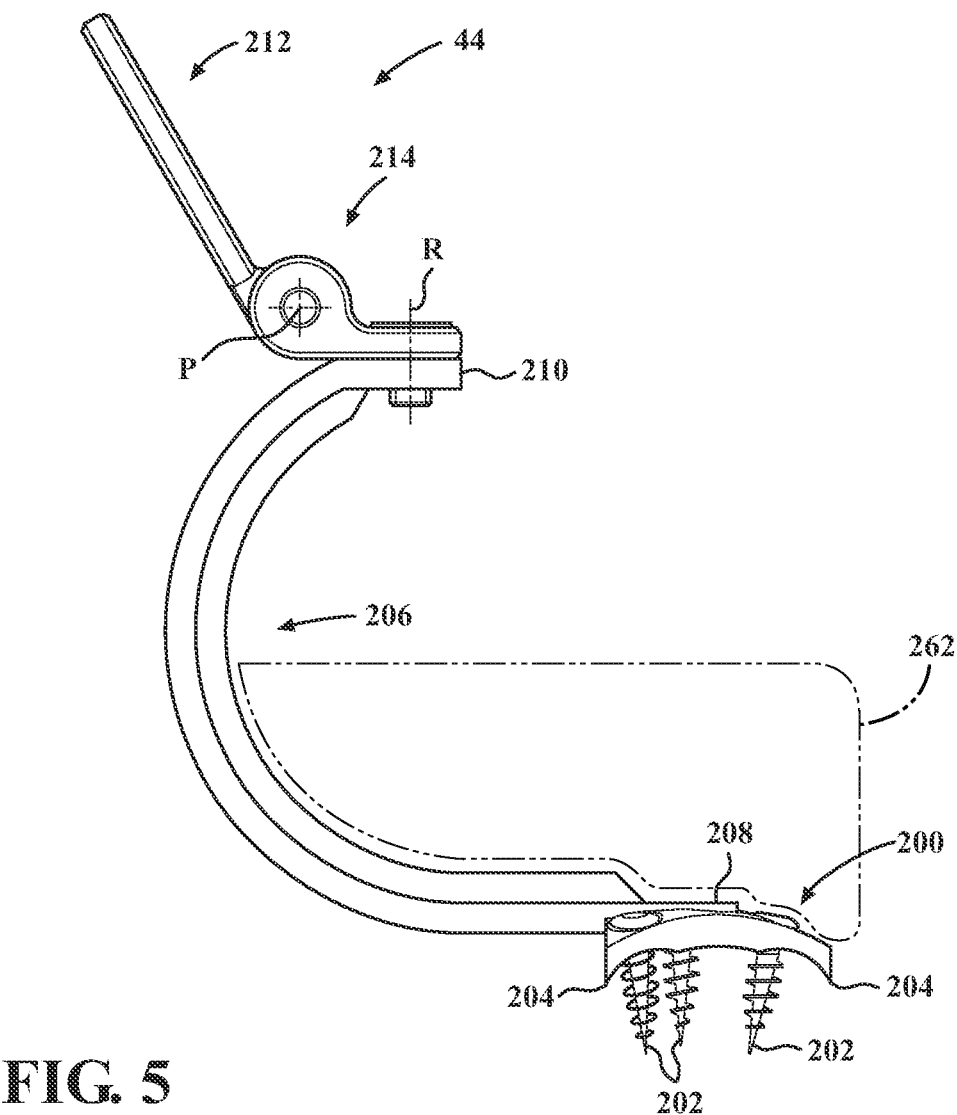
FIG. 5 is an elevational view of the tracking device of FIG. 4.
Figure 6:
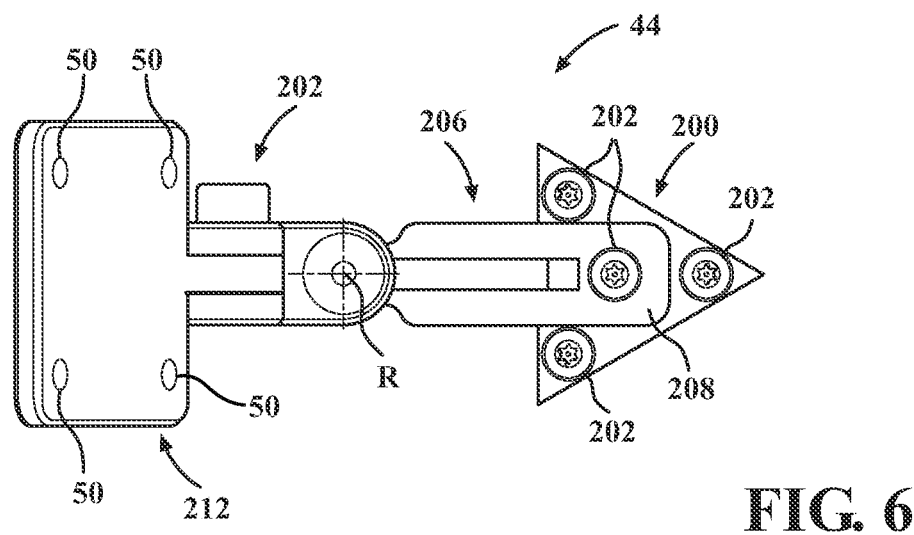
FIG. 6 is a top view of the tracking device of FIG. 4.

One embodiment of trackers 44, 46 is shown in FIGS. 4-6. Trackers 44, 46 are configured to be attached to bone and fixed in position relative to the bone. As a result, movement of the bone results in corresponding and like movement of the trackers 44, 46. In some versions of the navigation system 20, both trackers 44, 46 comprise the same or substantially the same components. In other versions, the trackers 44, 46 differ in one or more components. For simplicity, only tracker 44 will be described below, but it is understood that tracker 46 may be the same or substantially the same as tracker 44.

Referring to FIGS. 4-6, tracker 44 includes a base for attaching to the patient's anatomy. The base can be attached directly to the anatomy being tracked or through other tissue. In the embodiment shown, the base is a bone plate 200 for attaching to the patient's bone—for instance the femur F. A plurality of fasteners secures the bone plate 200 in place. In one embodiment, the fasteners are bone screws 202.

The bone plate 200 includes a plurality of protrusions for engaging the bone. In the embodiment shown, the protrusions are spikes 204. Once the bone plate 200 is secured in place with one or more bone screws, the spikes 204 prevent rotation of the bone plate 200 relative to the bone.

An extension arm 206 is mounted to the bone plate 200. The extension arm 206 has a base plate 208 that is secured to the bone plate 200 with one of the bone screws 202. The extension arm 206 extends arcuately in a C-shape from the base plate 208 to a mounting end 210.

A tracking head 212 is coupled to the mounting end 210 of the extension arm 206. The tracking head 212 includes tracking elements. The tracking elements, in the embodiment shown and described, are the LEDs 50, gyroscope sensor 60 (not shown), and accelerometer 70 (not shown). These tracking elements operate as previously described. In further embodiments, the tracking head 212 may include other types of tracking elements such as radio frequency receivers and/or transmitters, magnetic field sensors and/or generators, passive reflector balls, ultrasonic transmitters and/or receivers, or the like.

A connector assembly 214 couples the tracking head 212 to the extension arm 206. The connector assembly 214 supports the tracking head 212 for movement in two degree of freedom. In the embodiment shown, the tracking head 212 is rotatably and tiltably mounted to the mounting end 210 of the support arm 206 via the connector assembly 214.

Referring to FIGS. 7-10, the bone plate 200 is shown in greater detail. The bone plate 200 is generally triangular and concave between each spike 204 (see FIG. 9). This concavity conforms to or otherwise accommodates the shape of bone or other tissue to which the bone plate 200 is to be secured.

The bone plate 200 has top and bottom surfaces 216, 218 with three side surfaces 220, 222, 224. The side surfaces 220, 222, 224 extend between the top and bottom surfaces 216, 218. The concavity of the bone plate 200 can be given by a radius of curvature R1 of the top surface 216 of from about 5 millimeters to about 50 millimeters and a radius of curvature R2 of the bottom surface 218 of from about 5 millimeters to about 50 millimeters (see FIG. 9). In other embodiments, the radius of curvature R1 is from about 15 millimeters to about 35 millimeters and the radius of curvature R2 is from about 15 millimeters to about 35 millimeters.

Three spikes 204 are formed as integral extensions of surfaces 218, 220, 222, 224. Each spike 204 has a sharp tip 226 (see FIG. 10) that is formed near the intersection of the bottom surface 218 and two adjacent side surfaces 220, 222, 224. The bottom surface 218 extends arcuately along each spike 204 to the sharp tip 226 to form a gradual taper to the sharp tip 226. The bottom surface 218 is generally concavely shaped between sharp tips 226.

The sharp tips 226 are formed to cut through soft tissue, such as the periosteum, and pierce into bone when the bone plate 200 is secured to bone. When one or more of the sharp tips 226 pierce into bone, they, in conjunction with one or more of the bone screws 202, prevent movement of the bone plate 200 relative to the bone.

The sharp tips 226, when engaged in bone, also support the bone plate 200 to provide a space beneath the bone plate 200 and above the surface of the bone. In some cases, tissue such as muscle, ligaments, and the like may be present on top of the bone to which the bone plate 200 is to be secured. This tissue can be accommodated in this space without affecting the engagement of the sharp tips 226 in the bone.

Three openings 228 are defined through the bone plate 200 to receive the bone screws 202. These three openings 228 have the cross-sectional configuration shown in FIG. 10. One embodiment of this configuration is shown in U.S. Pat. No. 6,322,562 to Wolter, hereby incorporated by reference, in order to receive threaded heads 205 of the bone screws 202 shown in FIGS. 11-15.

Each of the openings 228 are defined about an axis A. Each opening 228 comprises a generally cylindrical throughbore 230 defined by inner surface 234. The throughbore 230 is centered about the axis A.

An integral flange 232 is located in the throughbore 230 and directed radially inward toward axis A. The flange 232 is spaced from the top and bottom surfaces 216, 218 of the bone plate 200. This flange 232 is disposed annularly about axis A and generally perpendicular to axis A. The flange 232 tapers in cross-section from the inner surface 234 to an end surface 236. The end surface 236 defines an opening (not numbered) that is cylindrical in shape. The taper of the flange 232 is symmetrically formed by upper and lower surfaces 240, 242. The upper surface 240 extends at an acute angle α from end surface 236 to inner surface 234. The lower surface 242 extends at the same acute angle α from the end surface 236 to the inner surface 234, but in the opposite direction.

Referring back to FIG. 7, a recess 244 is defined in the top surface 216 of the bone plate 200. The recess 244 is generally rectangular in shape for mating reception of the base plate 208 of the extension arm 206. The base plate 208 is sized so that once located in the recess 244 the extension arm 206 is substantially prevented from rotation relative to the bone plate 200.

A central opening 246 is located in the recess 244 and is defined through the bone plate 200. The central opening 246 receives a bone screw 202 similar to the openings 228, but has a different cross-section than openings 228. The central opening 246 is a generally cylindrical throughbore of single diameter that is substantially perpendicular to the bone plate 200 at that location.

Figure 8:
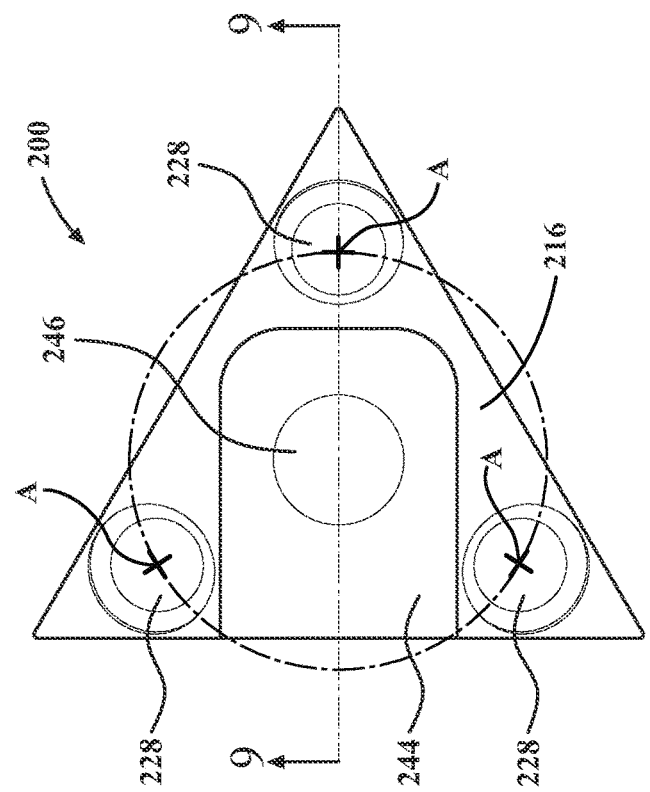
FIG. 8 is a top view of the bone plate of FIG. 7.
Figure 7:
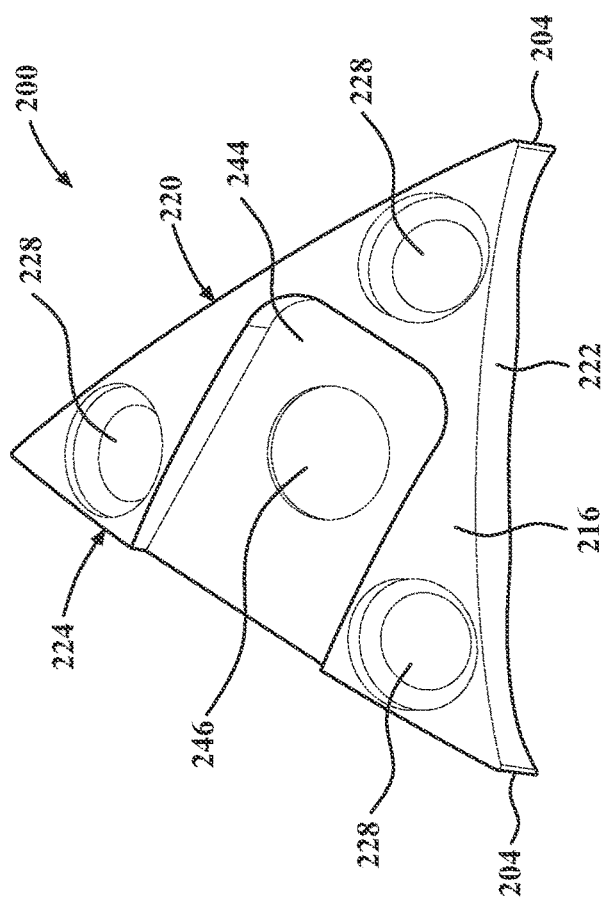
FIG. 7 is a perspective view of a bone plate in accordance with a first embodiment of the present disclosure.
Figure 10:
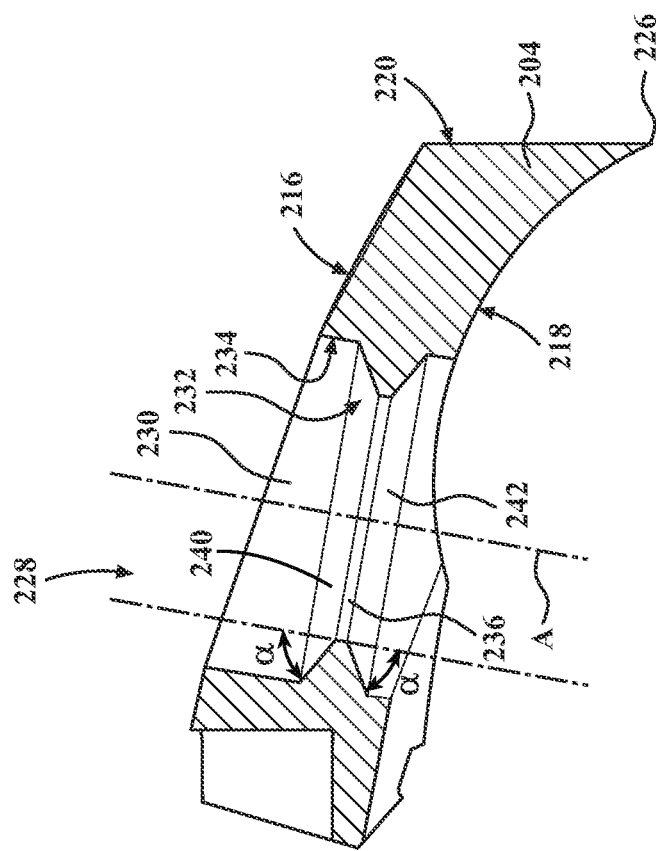
FIG. 10 is a blown-up view from FIG. 9.
Figure 9:
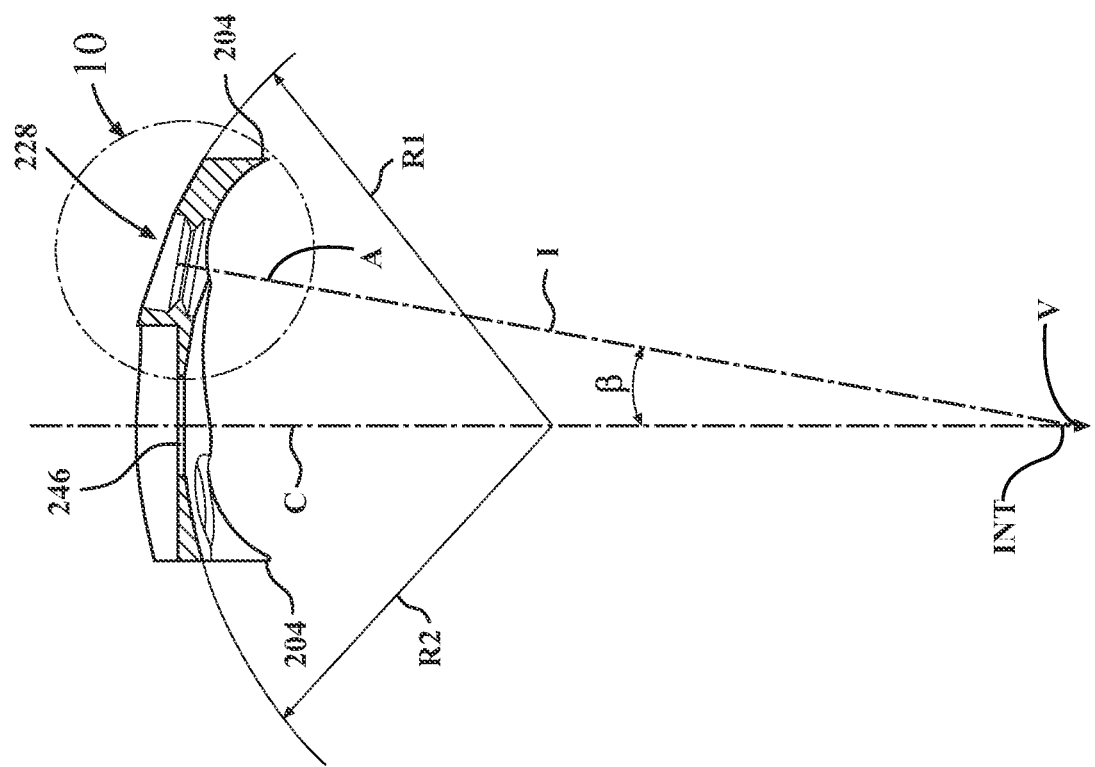
FIG. 9 is a cross-sectional view of the bone plate of FIG. 7 taken generally along the line 9-9 in FIG. 8.

An axis C defines a center of the throughbore 246, as shown in FIG. 9. The openings 228 are spaced equidistantly from the axis C. Additionally, the openings 228 are spaced equally circumferentially about an imaginary circle defined through axes A of each of the openings 228 (see FIG. 8).

Referring to FIG. 9, a normal directional vector V to the bone plate 200 is defined downwardly along axis C toward the patient's anatomy when mounted. Inclined directional vectors I, arranged at acute angle β to the normal directional vector V, are defined downwardly along axes A. In one embodiment, these inclined directional vectors I are generally directed toward the normal directional vector V and cross the normal directional vector V at the same point INT along axis C. This orientation assists with preventing pull-out of the bone screws 202 from forces acting on the bone plate 200.

Figure 10A:
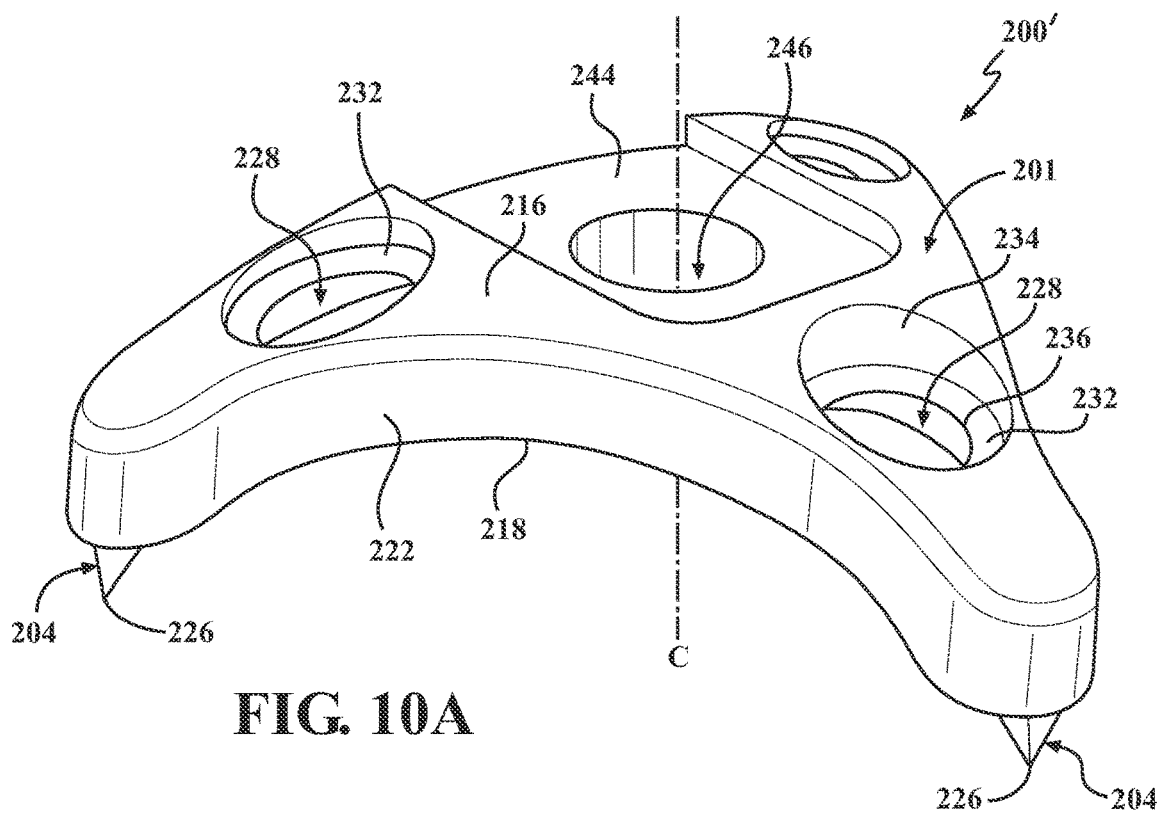
FIG. 10A is a perspective view of a bone plate in accordance with a second embodiment of the present disclosure.
Figure 10B:
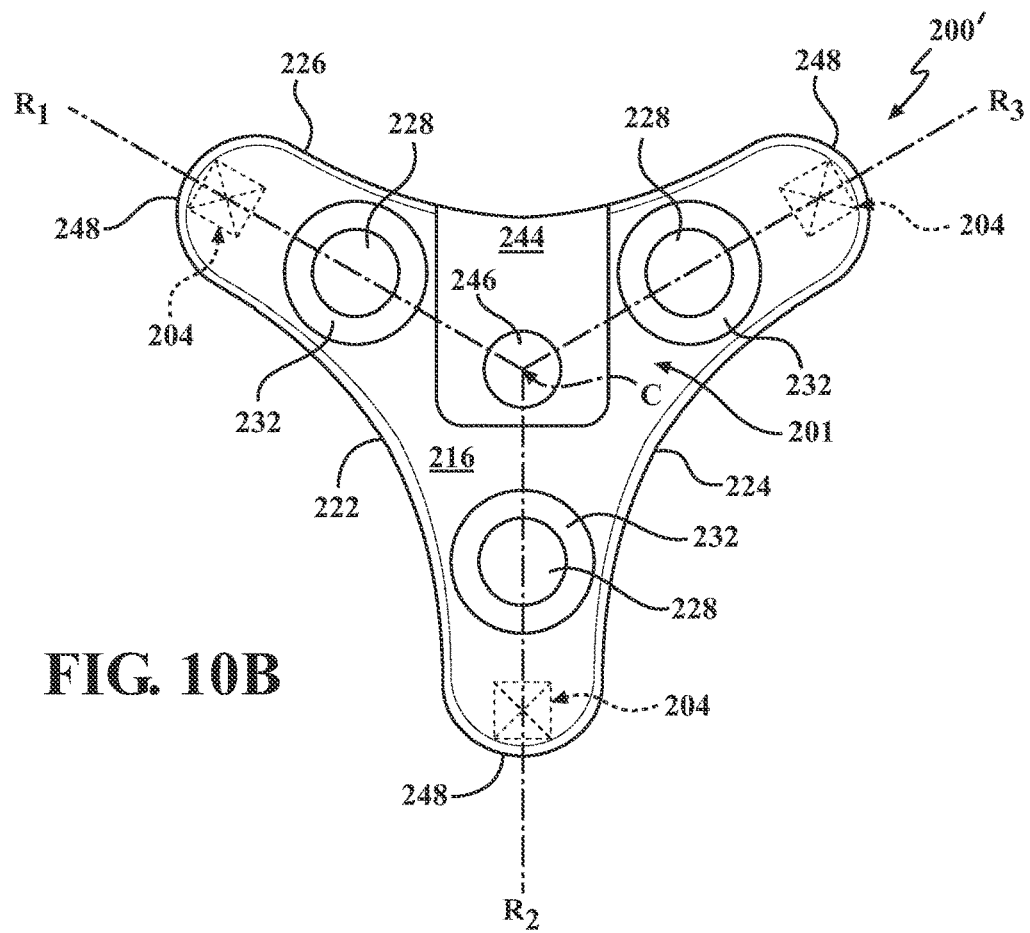
FIG. 10B is a top view of the bone plate of FIG. 10A.

FIGS. 10A and 10B show a bone plate 200' in accordance with another exemplary embodiment of the present disclosure. In many respects, the bone plate 200' is similar in structure and function as the bone plate 200 previously disclosed. The bone plate 200' comprises a body 201 including the top surface 216 and the bottom surface 218 opposite the top surface 216. The body 201 defines the opening(s) 228 extending through the top surface 216 and the bottom surface 218. In the illustrated embodiment, the body 201 defines three openings, like the bone plate 200 previously disclosed; however, any number of openings 228 are contemplated.

Spikes 204 are associated with the body 201 and are configured to penetrate the anatomical structure such as a femur, F, tibia, T, or any bony or other anatomy capable of securely receiving a fastener such as the bone screw 202. In conjunction with the fastener, the spikes 204 prevent rotational movement of the body 201 relative to the anatomic structure F as previously disclosed herein. More specifically, the spikes 204 comprise a gradual taper to a sharp tip 226 formed to penetrate the anatomic structure such as bone.

Figure 10D:
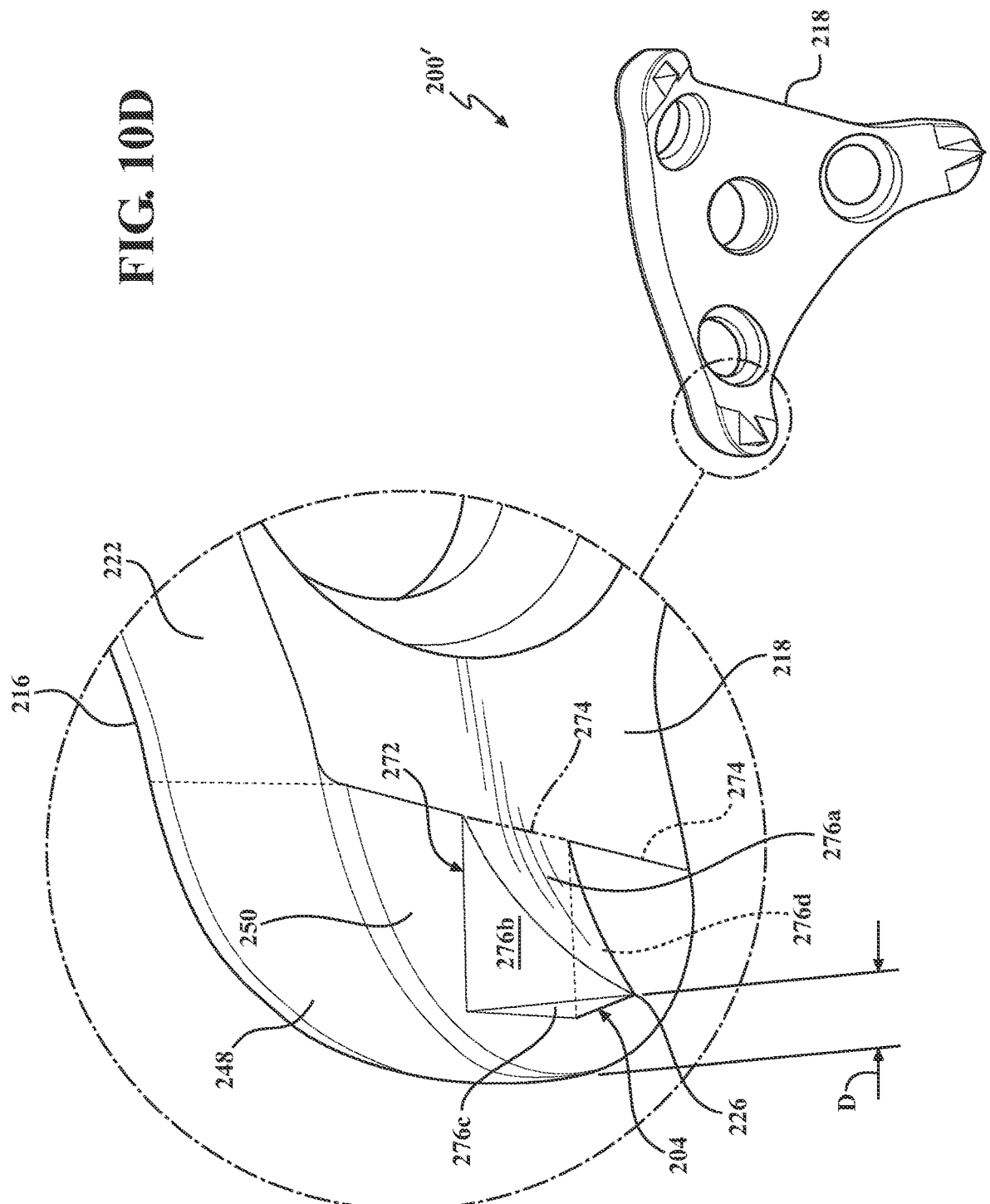
FIG. 10D a bottom perspective view of the bone plate of FIG. 10A, with a blown-up view detailing a spike and a bone pad surface in accordance with a version of the second embodiment of the present disclosure.
Figure 10E:
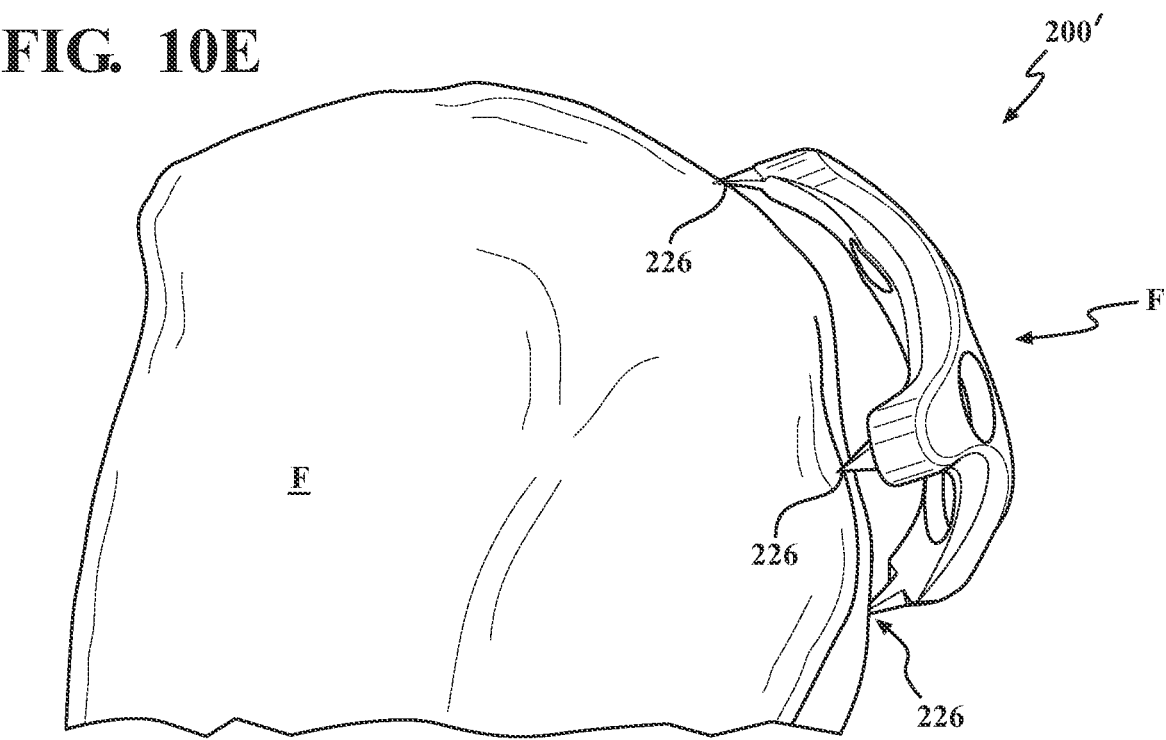
FIG. 10E a perspective bone of the bone plate of FIG. 10A prior to engagement with the bone.
Figure 10F:
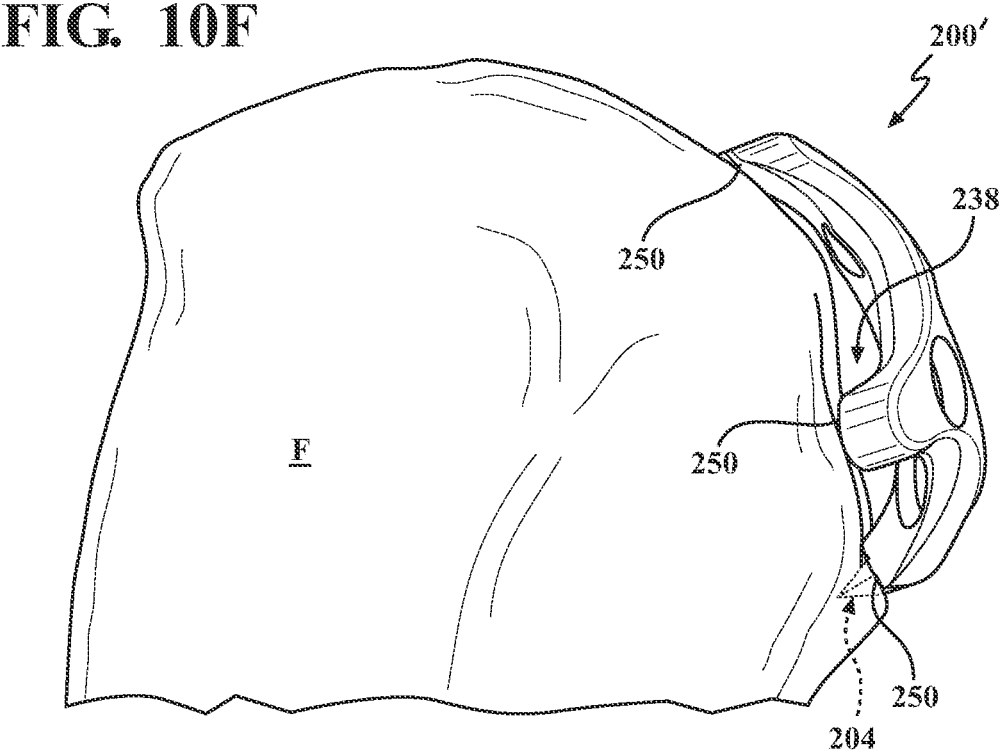
FIG. 10F a perspective view of the bone plate of FIG. 10A following engagement with the bone.

The bottom surface 218 is concave between the spikes 204, as best illustrated in FIGS. 9 and 10C and 10F. When the body 201 is attached to the anatomic structure, the bottom surface 218 defines a space 238 configured to accommodate portions of the anatomic structure, as best illustrated in FIG. 10F and as previously disclosed herein.

FIG. 10B illustrates a top plan view of the bone plate 200'. When viewed in plan, the top surface 216 and the bottom surface 218 define a generally triangular shape of the body 201, preferably an equilateral triangle. The side surfaces 222 can extend between the top surface 216 and the bottom surface 218. Whereas the previously disclosed bone plate 200 can comprise adjacent side surfaces 222 intersecting at a point (see FIG. 8), the bone plate 200' of FIGS. 10A and 10B illustrate peripheral edges 248 arcuately extending between adjacent side surfaces 222. Similarly, whereas the previously disclosed bone plate 200 can comprise substantially linear side surfaces 222 (see FIG. 8), the bone plate 200' of FIGS. 10A and 10B illustrate arcuate side surfaces 222. The arcuate side surfaces 222 can be concave, as illustrated, or convex or linear. The concave side surfaces 222 and the peripheral edges 248 advantageously provide for improved control of the bone plate 200' during handling and/or surgical placement and removal. The peripheral edges 248 and the side surfaces 222 generally define a periphery of the bone plate 200'.

The center axis, C, can be defined equidistant from the side surfaces 222, as illustrated in FIG. 10A. Like the first embodiment of the bone plate 200, the second embodiment illustrated in FIGS. 10A and 10B shows the center axis, C extending through the throughbore 246 (see also FIG. 9). A center of each of the openings 228 can be equidistant from the center axis, C, as illustrated in FIGS. 8 and 10B. Further, referring to FIG. 10B, radial axes, $R_1$, $R_2$, $R_3$, extend from the center axis, C, through a center of each of the openings 228. The openings 228 can be radially spaced equally about the center axis, C. In other words, an angle between an adjacent two of the three radial axes, $R_1$, $R_2$, $R_3$, can be 120 degrees.

Furthermore, the spikes 204 can be positioned along the radial axes $R_1$, $R_2$, $R_3$. With continued reference to FIG. 10B, each of the spikes 204 can be radially spaced equally about the center axis, C, with an angle between an adjacent two of the three spikes 204 being 120 degrees. Further, the spikes 204 can be positioned outwardly towards the peripheral edge 248 relative to the openings 228.

While some embodiments comprise a generally triangular plate with three openings and three spikes positioned radially about a center of the bone plate, numerous variations are contemplated. The body 201 can be a square, rhombus, trapezoid, pentagon, hexagon, or any other suitable shape. The shape may be based, at least in part, on the surgical application, and more particularly, on the shape of the anatomic structure to which the bone plate is attached and/or the desired number of fasteners to be utilized. While each opening is configured to receive a fastener, not using a fastener with one or more of the openings may be surgically indicated for any number of reasons. Thus, for example, the bone plate may be generally hexagonal having six spikes and six openings, only four of which receive fasteners based on a particular anatomic shape (e.g., scapula, iliac crest, etc.).

Other variations are also contemplated. The spikes may be positioned inwardly from the peripheral edge relative to the openings. In such a configuration, the openings are positioned proximate to an intersection of two of the adjacent side surfaces. Spacing the openings at a greater distance from the center axis, C, can provide for a more secure connection between the bone plate 200' and the anatomic structure. Further, based on the curvature of the top surface and the bottom surface, spacing the openings a greater distance from the center axis, C, orients the fasteners on a greater angle, β, to further assist with preventing pull-out of the fasteners from forces acting on the bone plate (see FIG. 9).

As mentioned, the sharp tips 226 are configured to penetrate the anatomic structure such that the spikes 204 prevent rotation of the bone plate 200, 200' relative to the bone. In the first embodiment of the bone plate 200, as the bone screws 202 are tightened during attachment of the bone plate 200, and the depth at which the spikes 204 penetrate the anatomic structure is limited primarily by the user applying a tightening force to the fasteners, and limited ultimately by the bottom surface 218 contacting the anatomic structure. Yet, the space 238 defined by the concave bottom surface 218 is provided to accommodate a portion of the anatomic structure and/or anatomic material such as tissue, muscle, ligaments and the like, without affecting the engagement of the sharp tips 226 and the anatomic structure. Therefore, those having skill in the art appreciate that in some cases there is an optimal depth to which the sharp tips 226 should penetrate the anatomic structure to generate the requisite engagement while providing the desired space 238 defined by the concave bottom surface 218.

Figure 10G:
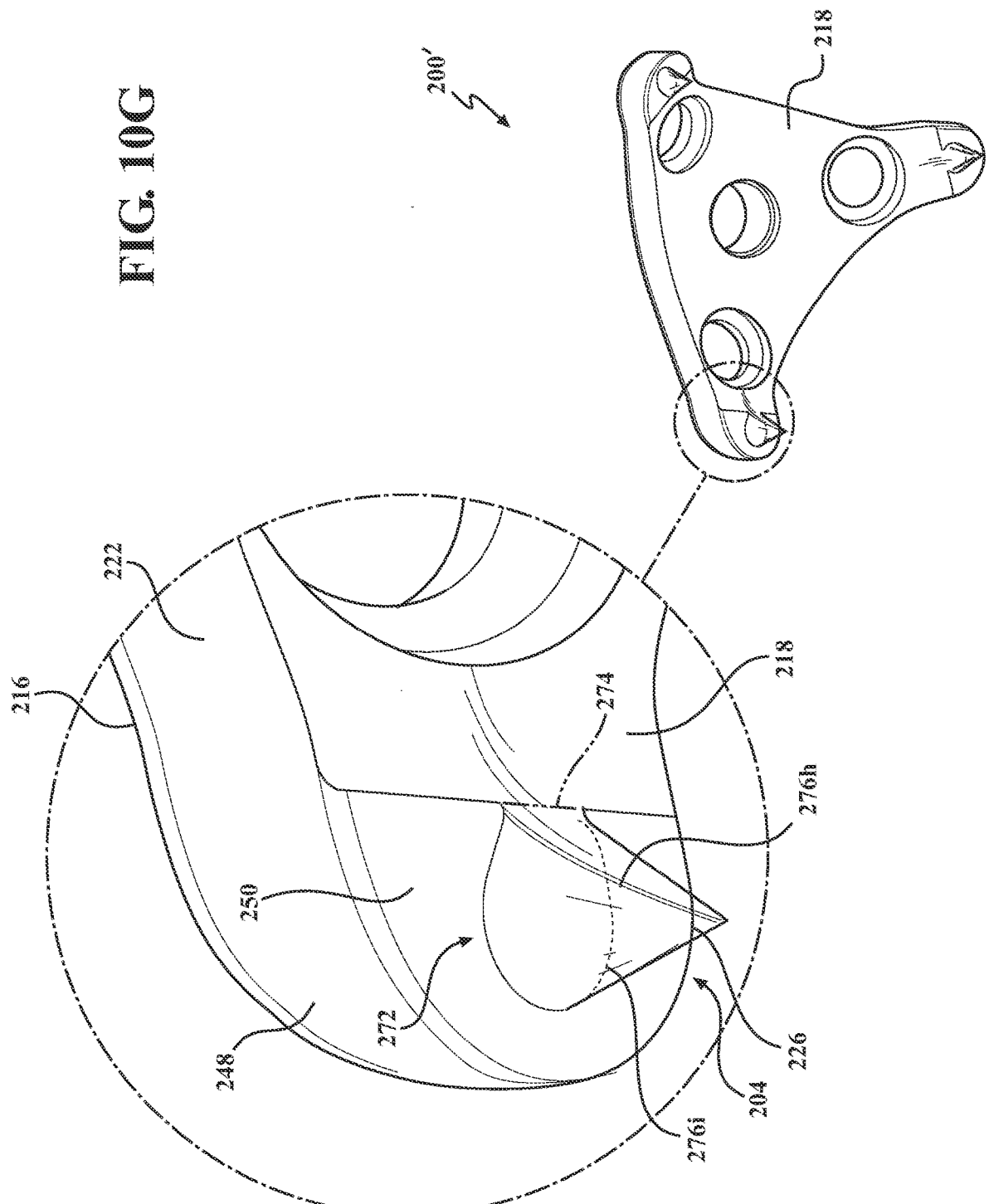
FIG. 10G a bottom perspective view of the bone plate of FIG. 10A, with a blown-up view detailing a spike and a bone pad surface in accordance with another version of the second embodiment of the present disclosure.
Figure 10H:
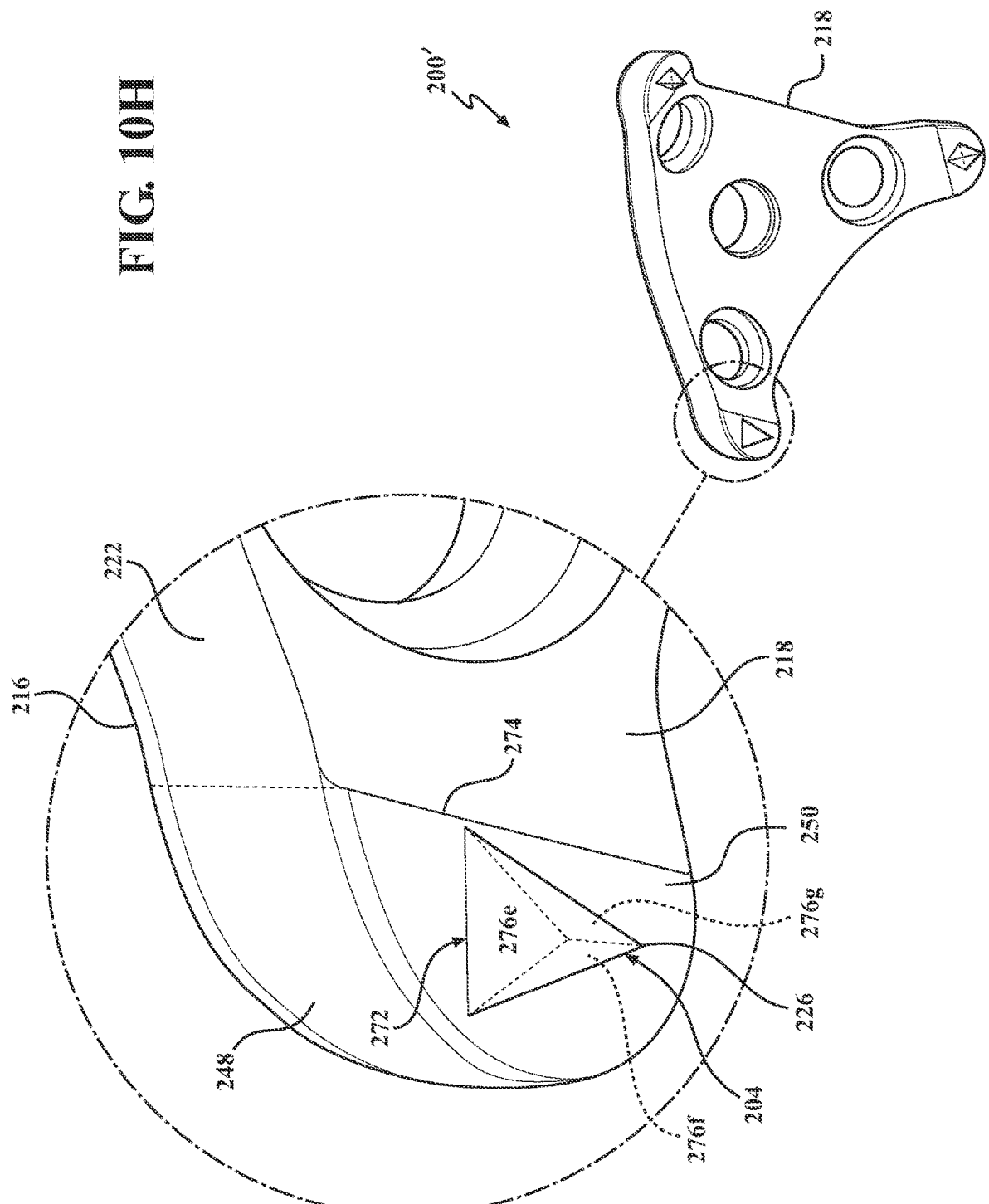
FIG. 10H a bottom perspective view of the bone plate of FIG. 10A, with a blown-up view detailing a spike and a bone pad surface in accordance with still another version of the second embodiment of the present disclosure.

According to a second embodiment of the bone plate 200', bone pad surfaces 250 are provided. Referring to FIGS. 10C and 10D, the body 201 of the bone plate 200' further comprises the bone pad surfaces 250 configured to prevent further penetration of the spikes 204 into the anatomic structure. To do so, the bone pad surfaces 250 contact the anatomic structure after the spikes 204 have penetrated the anatomic structure by a predetermined depth. Referring to FIGS. 10D, 10G and 10H, the spikes 204 each comprise a base 272 coupled to and extending away from the bone pad surface 250. The base 272 gradually tapers to the sharp tip 226.

The spikes 204 can be coupled to the bone pad surfaces 250 with a fastener or other joining means including but not limited to welding, brazing, soldering, and the like. A fastener such as a bolt, can extend through a borehole within the body 201 to fixedly secure the spikes 204 to the bone pad surfaces 250. In a preferred embodiment, the spikes 204 are integrally formed with the bone pad surfaces 250 of the body 201.

In a general sense, the bone pad surfaces 250 separate the body 201 and the spikes 204. The body 201 of the bone plate 200' can be defined between the top surface 216, the bottom surface 218, the side surfaces 222 (and the peripheral edges 248), as best illustrated in FIG. 10D. The bone pad surfaces 250 are effectively a boundary between the body 201 and the spikes 204.

To prevent further penetration of the spikes 204, the bone pad surfaces 250 are designed to create sufficient interference with the anatomic structure adjacent the spikes 204. More specifically, the bone pad surfaces 250 are oriented such that, when in contact with the anatomic structure, attempts to further penetrate the anatomic structure with the spikes 204 (e.g., via tightening of the bone screws 202) cannot overcome the interference created by the bone pad surfaces 250. To create sufficient interference, the bone pad surfaces 250 adjacent or proximate the spikes 204 can be substantially parallel to the anatomic structure. Referring to FIG. 10C, line Z is associated with one of the bone pad surfaces 250 and line Z' is generally tangent to a portion of the femur, F, proximate to the penetrating spike 204. Lines Z and Z' are substantially parallel such that, when the bone plate 200' is attached to the femur, a contact area between the bone pad surface 250 and the portion of the femur is maximized to create sufficient interference to prevent further penetration of the spikes 204. Doing so prevents a decrease of the space 238 defined by the concave bottom surface 218 between the spikes 204. The result advantageously ensures the bone plate 200' is unable to rotate relative to the anatomic structure, while maximizing space to accommodate a portion of the anatomic structure or other soft tissues or body structures.

A portion of the process of attaching the bone plate 200' to the anatomic structure is illustrated in FIGS. 10E and 10F. The bone plate 200' is positioned adjacent to the anatomic structure of interest. In the unattached configuration of FIG. 10E, the sharp tips 226 of the spikes 204 have yet to pierce the anatomic structure. A force, F, is applied to the bone plate 200', either with a bone hammer or other surgical instrument. Alternatively, the force can be applied during tightening of the bone screws 202 extending through the openings 228 until the body 201 in operable engagement with the bone plate 200'. Provided the force exceeds the requisite threshold to penetrate the anatomic structure, the bone plate 200' moves towards the same. Once the bone pad surfaces 250 contact the anatomic structure, the bone plate 200' is in an attached configuration and generally unable to further penetrate and/or move towards the anatomic structure. The user, typically a surgeon, feels the appreciable increase in resistance, after which the surgeon can insert the fasteners (or cease tightening the fasteners). In the attached configuration, the spikes 204, in conjunction with the fasteners, prevent rotational movement of the body 201 relative to the anatomic structure. Further, the space 238 defined by the concave bottom surface 218 between the spikes 204, accommodates a portion of the anatomic structure, F, and/or anatomic material such as skin, muscle, fat, vascular structures, and the like.

Figure 10I:
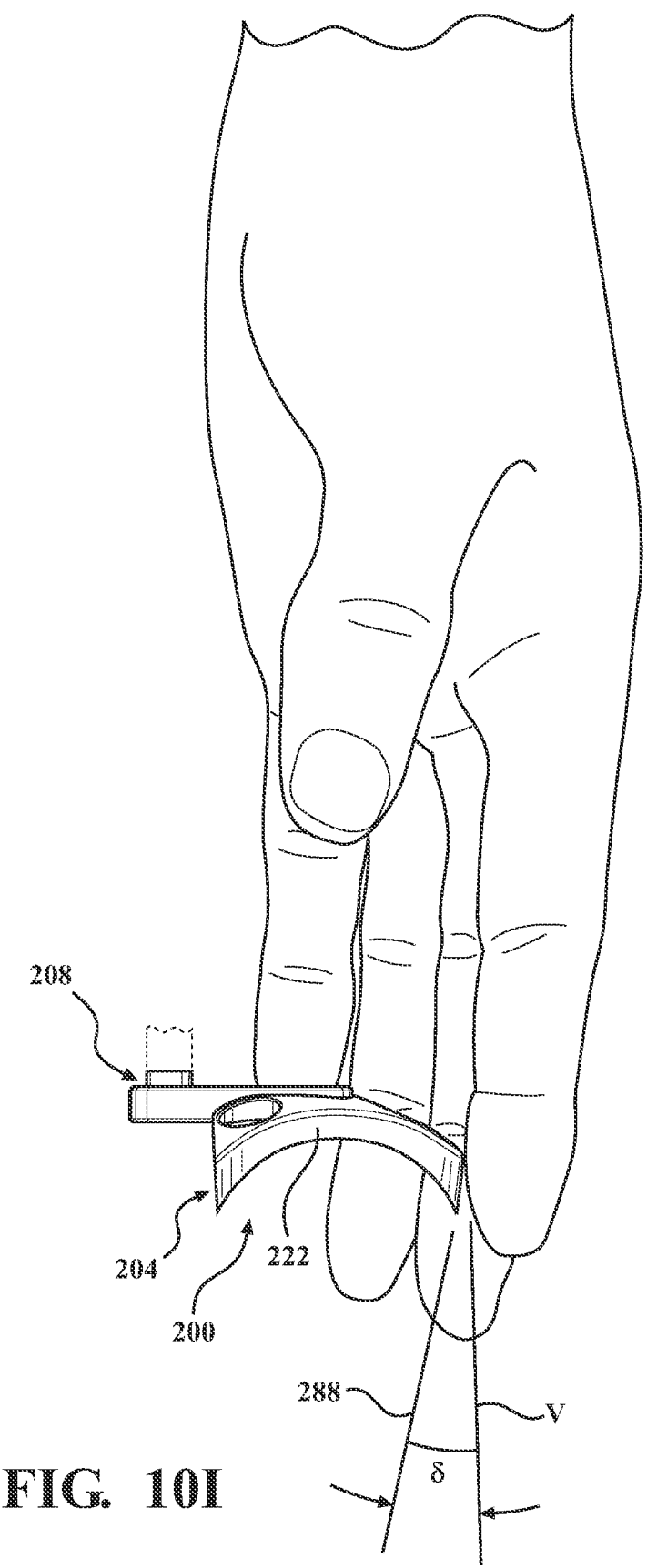
FIG. 10I is an elevational view of the bone plate of FIG. 7.
Figure 10J:
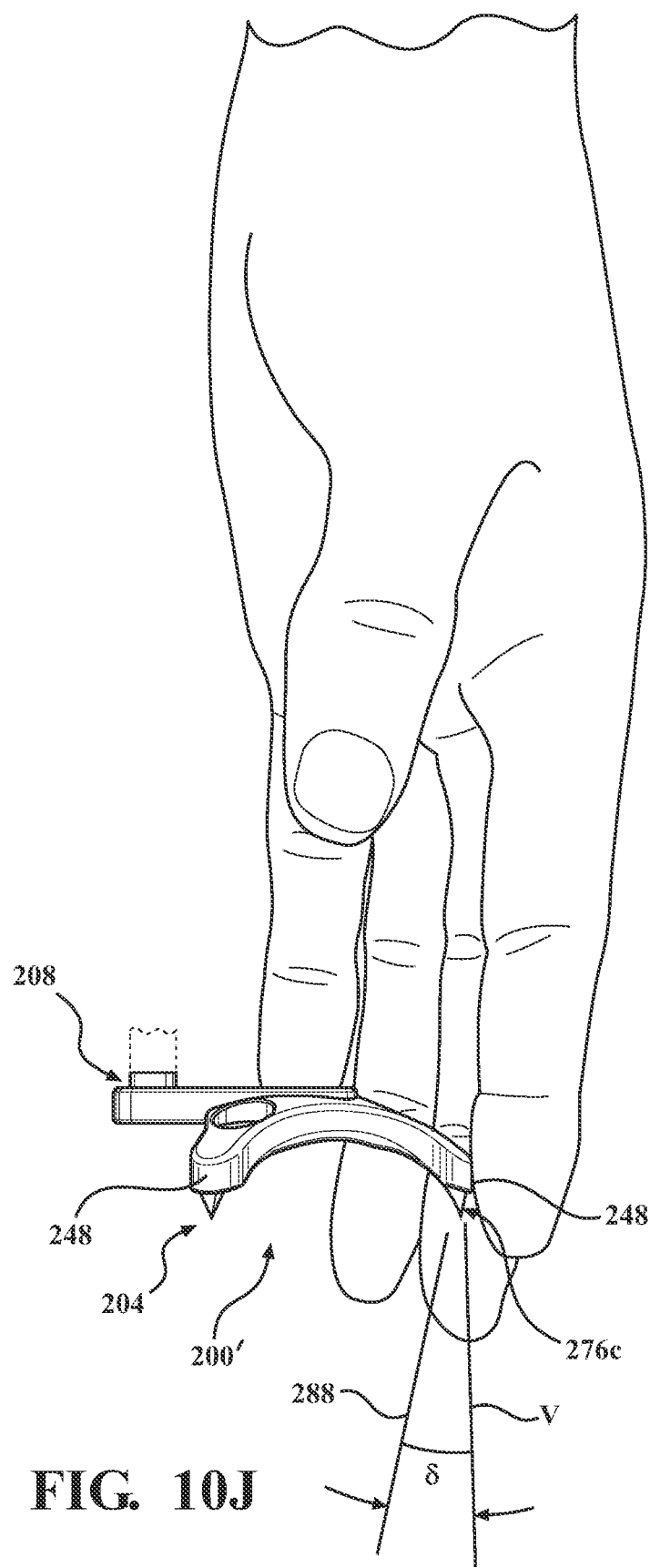
FIG. 10J is an elevational view of the bone plate of FIG. 10A.
Figure 10K:
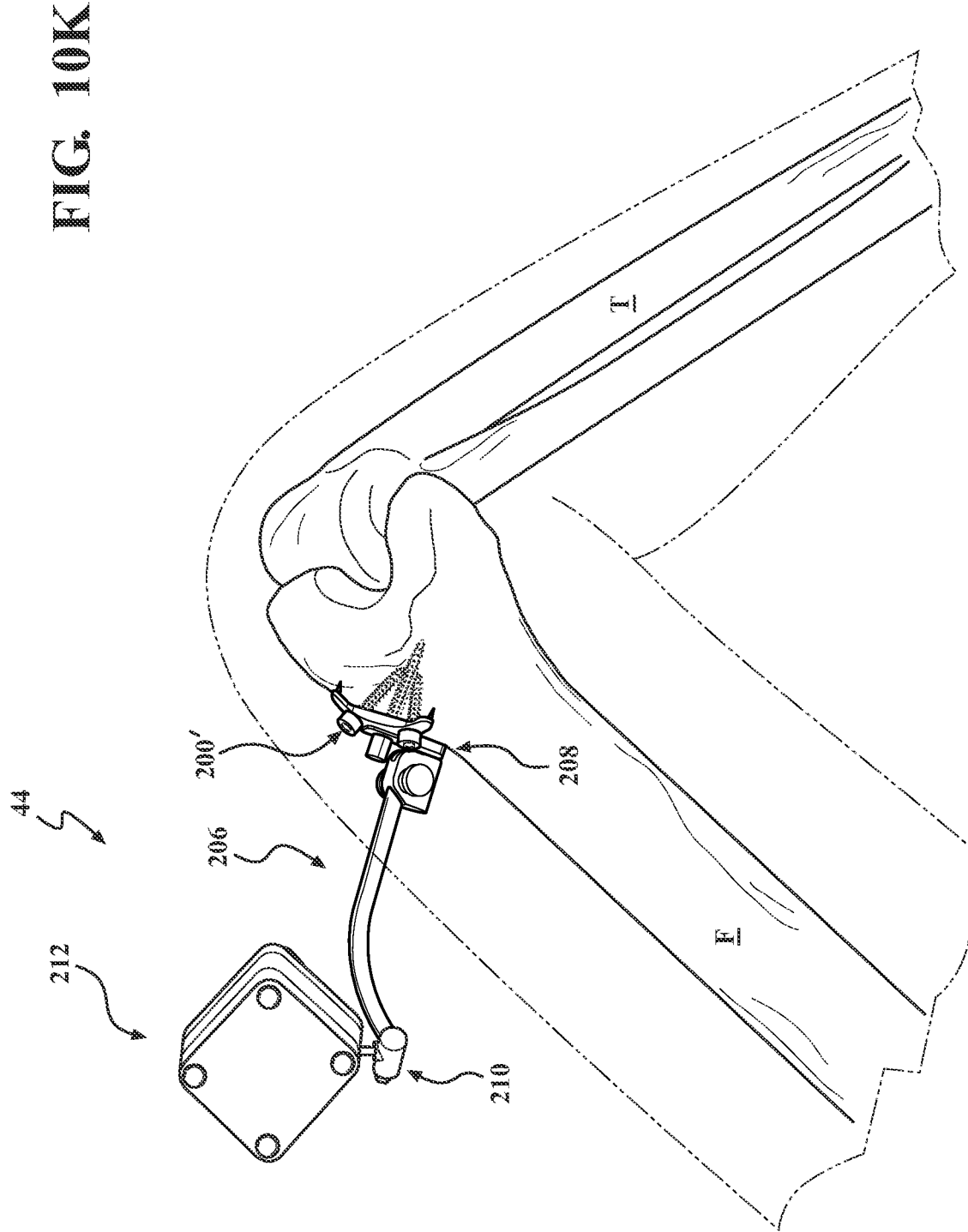
FIG. 10K is a schematic view of a tracking device with the bone plate of FIG. 10A.
Figure 13:
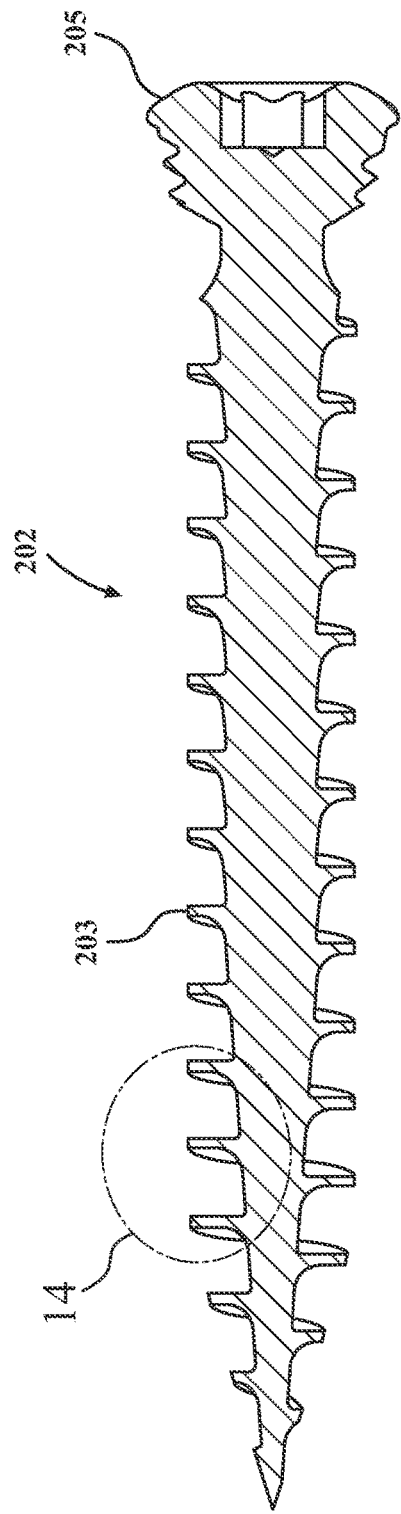
FIG. 13 is a cross-sectional view of the bone screw taken down the center of the bone screw.
Figure 15:
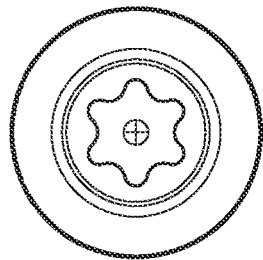
FIG. 15 is an end view of the bone screw of FIG. 12.
Figure 14:
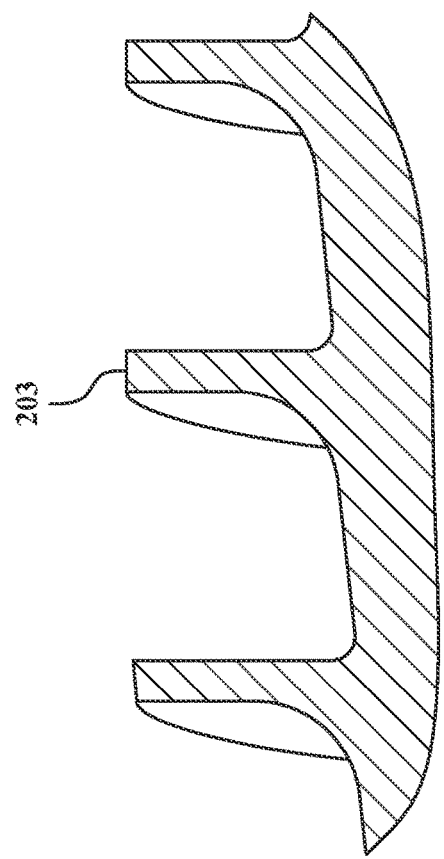
FIG. 14 is a blown-up view from FIG. 13.

Furthermore, during the surgical procedure, unanticipated forces may act upon the bone plate 200', via the tracking head 212, the extension arm 206, or otherwise (see FIGS. 1 and 10K). For example, during attachment of the tracking device to the extension arm 206, a torque may be applied to the bone plate 200, 200' previously secured to the anatomic structure. In such a scenario, the bone pad surfaces 250 advantageously prevent the sharp tip(s) 226 from further penetrating the anatomic structure, which would otherwise loosen the bone plate from the anatomic structure by creating a void between the spike 204 and the anatomic structure. This prevents the bone plate, and thus the tracking device, from wobble, which could compromise the accuracy of the surgical navigation system.

Referring to FIGS. 10C and 10D, the bone pad surfaces 250 are positioned adjacent the bottom surface 218 and the peripheral edges 248. To orient the bone pad surfaces 250 in a manner that creates sufficient interference with the anatomic structure, the bone pad surfaces 250 can be angled at an obtuse angle, γ, relative to the bottom surface 218 at a boundary 274 separating the bone pad surfaces 250 from the bottom surface 218. Doing so effectively transitions the bottom surface 218, which approaches the anatomic structure at a steeper angle (and thus more likely to permit further penetration of the anatomic structure with the spikes 204), to the bone pad surfaces 250 at a suitable orientation relative to the anatomic structure.

The angle, γ, can be designed based on the needs of the surgical application. Generally, the angle, γ, is between 90 degrees and 180 degrees. Within such a range, the bottom surface 218 more quickly achieves a greater distance from the anatomic structure. In other words, a lower angle, γ, provides for a relatively deeper space 238, whereas a greater angle, γ, provides for a relatively shallower space 238. For example, relatively deeper space 238 may be desired if the portion of the anatomic structure to which the bone plate 200' is being attached has protrusions and/or appreciable overlying soft tissue structures. For another example, a relatively shallower space 238 may be desired to limit the pull-out forces on the fasteners by minimizing the distance between the fasteners and the connection point to the extension arm 206 (i.e., the recess 244).

Focusing on FIG. 10D, the bone pad surfaces 250 can be substantially planar, or of any suitable profile to best approximate the corresponding profile of the anatomic structure adjacent the spikes 204. For example, the bone pad surfaces 250 can be arcuate and concave between the boundary 274 and the peripheral edge 248. A slightly concave bone pad surface 250 may better approximate spherical-shaped anatomic structures such as a condyle of the femur, an epicondyle of the humerus, the skull, and the like.

The spikes 204 can be substantially pyramidal in shape having inclined surfaces 276 tapering to the sharp tip 226. FIG. 10D illustrates a spike 204 that comprises four inclined surfaces 276a, 276b, 276c, 276d; however, the present disclosure contemplates any number of inclined surfaces. For example, FIG. 10G illustrates the spike 204 that comprises three inclined surfaces 276e, 276f, 276g. Alternatively or additionally, the spikes 204 can comprise shapes other than pyramids, including a conical spike (FIG. 10H), a compression-tree spike, or any combination thereof.

One of the inclined surfaces 276 of the spikes 204 can be integral and continuous with the bottom surface 218. Whereas the boundary 274 is generally associated with an abrupt change in angle between the bone pad surfaces 250 and the bottom surface 218, a surface integral and continuous with the bottom surface 218 effectively is an extension of the bottom surface 218 (i.e., the arcuate bottom surface 218 comprises a portion of the spikes 204). With continued reference to FIG. 10D, inclined surface 276a is integral and continuous with the bottom surface 218. Stated differently, the inclined surface 276a is arcuate with a radius of curvature equal to that of bottom surface 218. In such a configuration, the bottom surface 218 can extend arcuately along each of the spikes 204 to the sharp tips 226. The remaining three of the four inclined surfaces 276a, 276b, 276c are adjacent to the bone pad surface 250. During attachment of the bone plate 200' to the anatomic structure, the inclined surfaces 276 penetrate the anatomic structure until the bone pad surface 250 contacts the anatomic structure, after which further penetration is prevented.

FIG. 10G illustrates a spike 204 comprising a cone in accordance with another version of the second embodiment. One of the spikes 204 of FIG. 10G comprises a base 272 at least partially surrounded by the bone pad surface 250. The spike 204 can further comprise a surface 276h integral and continuous with the bottom surface 218. The surface 276h can be inclined and arcuate having the same radius of curvature as the bottom surface 218. In such an embodiment, the spike 204 is only partially a cone with the surface 276h comprising a chord of the base 272. A remaining portion 276i of the spike 204 is adjacent to the bone pad surface 250.

Referring to FIG. 10H, a spike 204 comprising a pyramid with the three inclined surfaces 276e, 276f, 276g is illustrated. In many respects the spike 204 of FIG. 10G is similar to the spike 204 of FIG. 10D. In FIG. 10H, however, none of the inclined surfaces 276e, 276f, 276g is integral and continuous with the bottom surface 218. Rather, the bone pad surface 250 extends around an entirety of the base 272 of the spike 204. More specifically, each of the three inclined surfaces 276e, 276f, 276g is adjacent to the bone pad surface 250. Such a configuration can be extended to any of the aspects of the second embodiment disclosed herein. In the context of the spike 204 of FIG. 10D, all of the four inclined surfaces 276a, 276b, 276c, 276d are adjacent to the bone pad surface 250. In the context of the spike 204 of FIG. 10G, the entirety of the base 272 of the cone is surrounded by the bone pad surface 250. The present disclosure also contemplates the bone pad surfaces 250 may be adjacent to one, two or five or more sides of the base 272 of the spikes 204, depending on the geometry of the spikes 204.

A further objective is to improve safety during handling of the bone plate 200, 200'. One manner by which this is achieved is illustrated in FIGS. 10I and 10J. The spikes 204 are angled away from a user to avoid accidental injury while handling the bone plate 200, 200', typically during attachment and removal. A tilt axis 288 associated with an outer surface of the spike 204 is oriented at an angle, δ, relative to vertical, V. For the first embodiment of the bone plate 200, the outer surface is an edge comprising an intersection between an adjacent two of the side surfaces 222. For the second embodiment of the bone plate 200', the outer surface can comprise one or more of the inclined surfaces 276a-276i proximate the peripheral edge 248. For example, as illustrated in FIG. 10J, the inclined surface 276c proximate to the peripheral edge 248 is oriented at an angle, δ, relative to vertical, V. Generally, the angle, δ, is an acute angle, and preferably between 5 degrees and 20 degrees. As illustrated in FIGS. 10I and 10J, the inwardly angled spikes 204 angled away from a user assist in avoiding a puncture wound or other injury from the sharp tips 226 during handling.

Alternatively or additionally, the second embodiment of the bone plate 200' comprises another manner by which safety during handling is achieved. As best shown in FIGS. 10D, the spikes 204 are spaced inwardly from the peripheral edge 248 of the body 201 by a distance, D. Thus, providing a portion of the bone pad surfaces 250 between the base 272 of the spikes 204 and the peripheral edges 248 can also serve as a safety mechanism. The user is less likely to suffer an injury when grasping the bone plate 200' from above as illustrated in FIG. 10J.

The bone plate 200, 200' may be formed of stainless steel, cobalt base alloys, bioceramics, titanium alloys, titanium, or other biocompatible materials. The material(s) are preferably rigid and non-conformable and configured to maintain relative positioning of the tracking head 212 under any conditions typically associated with surgical operations.

The second embodiment of the bone plate 200' is configured to be coupled to a tracking device for a surgical navigational system. Referring to FIGS. 1 and 10K, the trackers 44, 46, 48 include a tracking head 212 comprising tracking elements configured to transmit tracking information to the surgical navigation system, as previously disclosed herein. The extension arm 206 comprising the mounting end 210 and the base plate 208 is coupled to 212 tracking head at the mounting end 210. The bone plate 200' is coupled to the extension arm 206 at the base plate 208. More specifically, a recess 244 within the top surface 216 to couples the base plate 208 and the extension arm 206 to prevent rotation of the extension arm 206 relative to the body 201.

Bone screws 202 are shown in FIGS. 11-15. In one embodiment, the bone screws are similar to those shown in U.S. Pat. No. 6,322,562, incorporated by reference herein. Each of the bone screws 202 has self tapping threads 203 for engaging bone. The bone screws 202 also have the threaded heads 205 for engaging the flanges 232 of the openings 228. The bone screws 202 may be of different sizes depending on the tissue to which they are being mounted. For instance, if the bone plate 200, 200' is configured for mounting to a patella, smaller bone screws may be utilized. If the bone plate 200, 200' is being mounted to the tibia, which is typically harder than other bones of the body, smaller bone screws may be used. For soft bone, longer bone screws that implant deeper into the bone may be desired.

FIGS. 16-20 show the extension arm 206 in greater detail. The base plate 208 of the extension arm 206 defines a plate opening 252 that is the same in shape and size to the openings 228. The plate opening 252 has the same features as openings 228 and will not be described further. Plate opening 252 receives a central fastener such as bone screw 202 in the same manner as openings 228. In the embodiment shown, the base plate 208 is secured to the bone plate 200, 200' by virtue of compression of the base plate 208 against the bone plate 200, 200' when the bone screw 202 is fastened to bone through the plate opening 252 and central opening 246.

An arcuate segment 254 extends from the base plate 208 to the mounting end 210. A rib 256 is disposed partially on the base plate 208, extends along the arcuate segment 254, and ends at the mounting end 210. The rib 256 provides additional rigidity to the extension arm 206 to prevent bending, buckling, twisting, or other deformation of the extension arm 206.

A mounting surface 258 is located at the mounting end 210 of the extension arm 206. The mounting surface 258 is configured to support the connector assembly 214 and tracking head 212. The mounting surface 258 is generally planar. A threaded opening 260 is defined through the mounting end 210 for receiving a threaded adjustment fastener 261 (see FIG. 4).

The extension arm 206 interconnects the bone plate 200, 200' and the tracking head 212. The extension arm 206 spaces the tracking elements (such as LEDs 50) of the tracking head 212 from the bone plate 200, 200'. The tracking elements are spaced in this manner to extend above the anatomy thereby improving line-of-sight potential between the tracking elements and the optical sensors 40 of camera unit 36.

Figure 21:
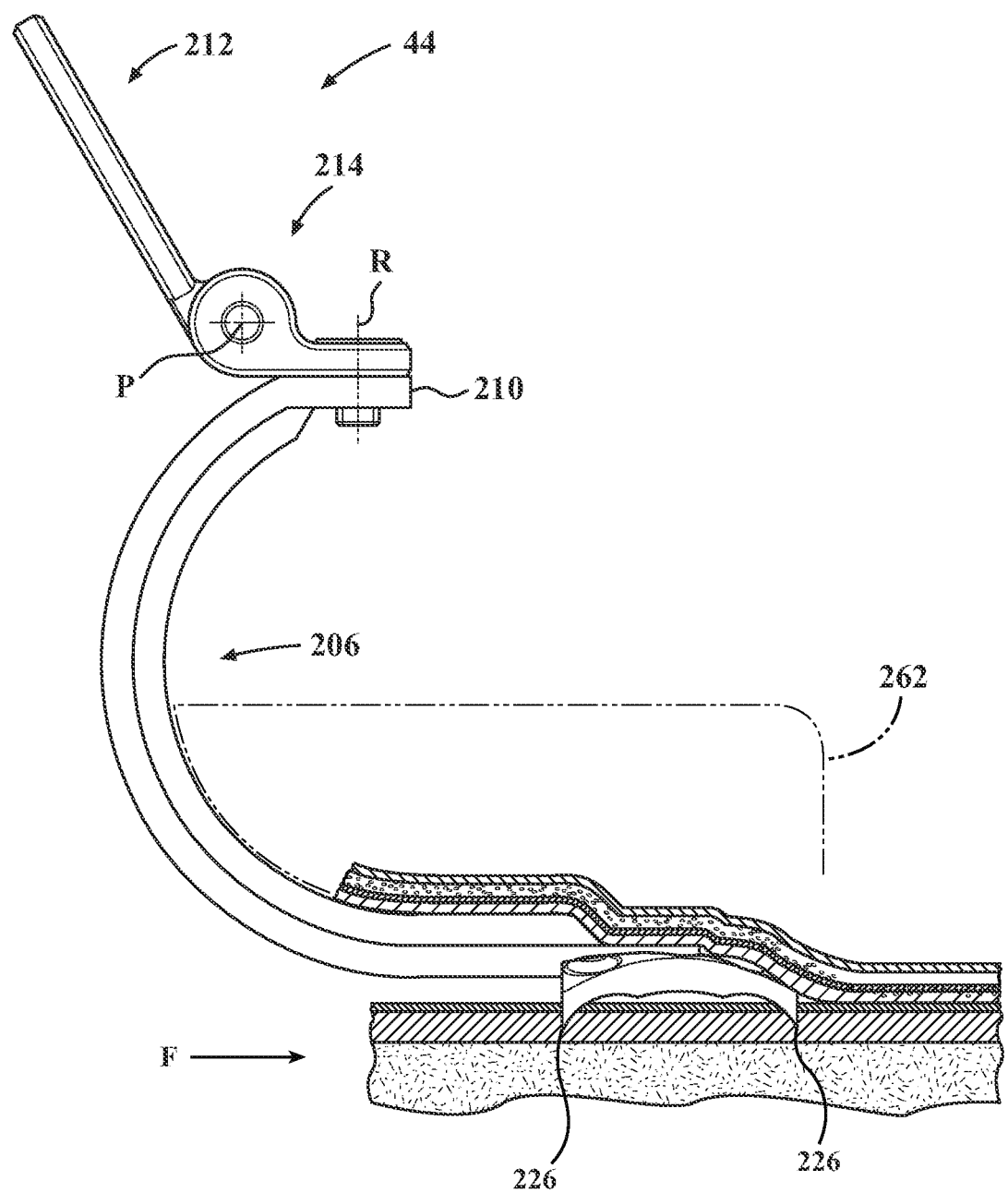
FIG. 21 is an elevational view of the tracker assembly of FIG. 4 shown attached to bone.
Figure 23:
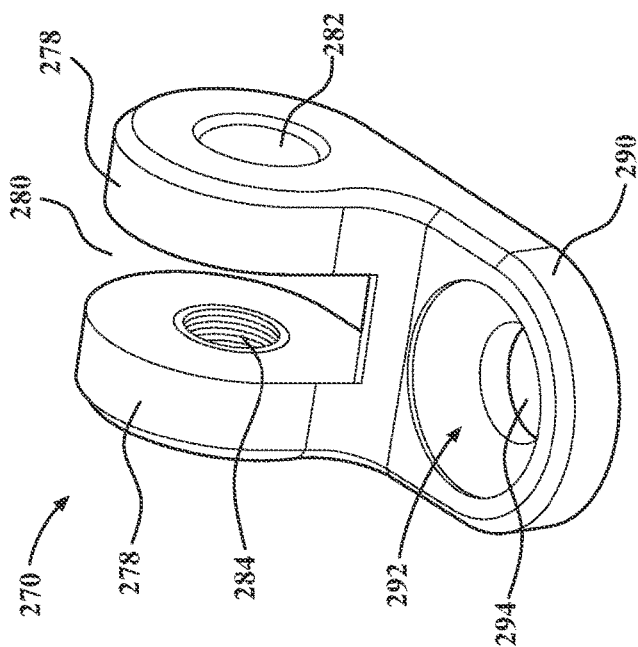
FIG. 23 is a perspective view of a connector.
Figure 25:
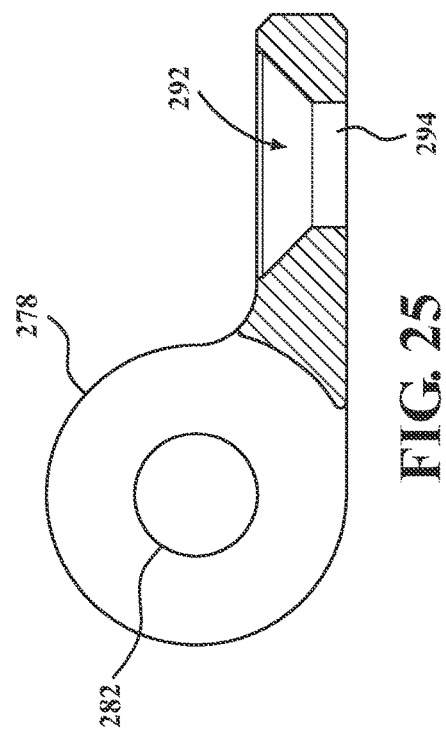
FIG. 25 is a cross-sectional view of the connector taken generally along the line 25-25 in FIG. 24.

Referring to FIG. 21, the extension arm 206 is generally C-shaped to define a tissue receiving area 262 between the tracker head 212 and the bone plate 200, 200'. The tissue receiving area 262 is configured to receive soft tissue such as skin, fat, muscle, etc. above the bone plate 200, 200' when the bone plate 200, 200' is mounted to the bone.

The tissue receiving area 262 enables the user to retract soft tissue away from bone, mount the bone plate 200, 200' directly to the bone, and then release the soft tissue back to a position above the bone plate 200, 200'. Accordingly, the soft tissue is not required to be continually retracted during the entire surgical procedure. FIG. 21 shows layers of skin, fat, muscle, and fascia being located in the tissue receiving area 262 while the bone plate 200, 200' is mounted to the femur F. In particular, the sharp tips 226 penetrate through the periosteum into the hard cortical bone of the femur F.

The bone plate 200, 200' is firmly mounted in bone unicortically—meaning the bone screws 202 only penetrate the cortical bone layer once, from the outside.

The extension arm 206 may be formed of stainless steel, cobalt base alloys, bioceramics, titanium alloys, titanium, or other biocompatible materials.

Figure 22:
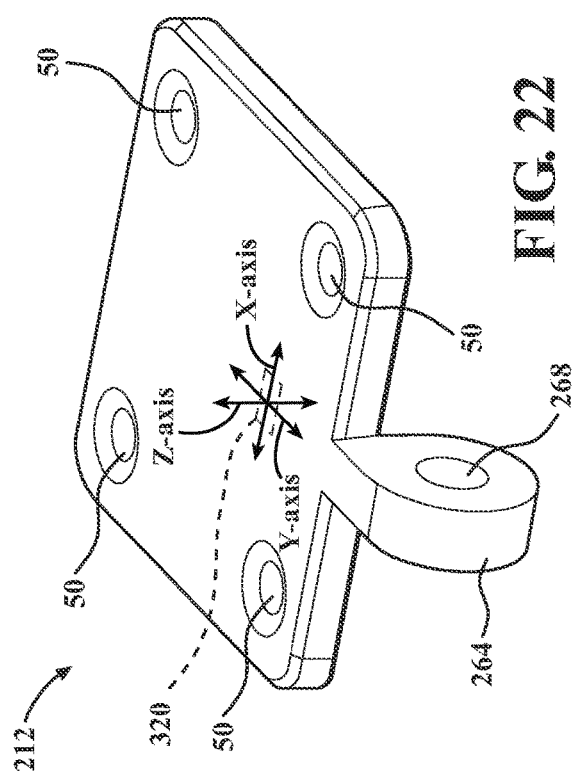
FIG. 22 is a perspective view of a tracking head.
Figure 24:
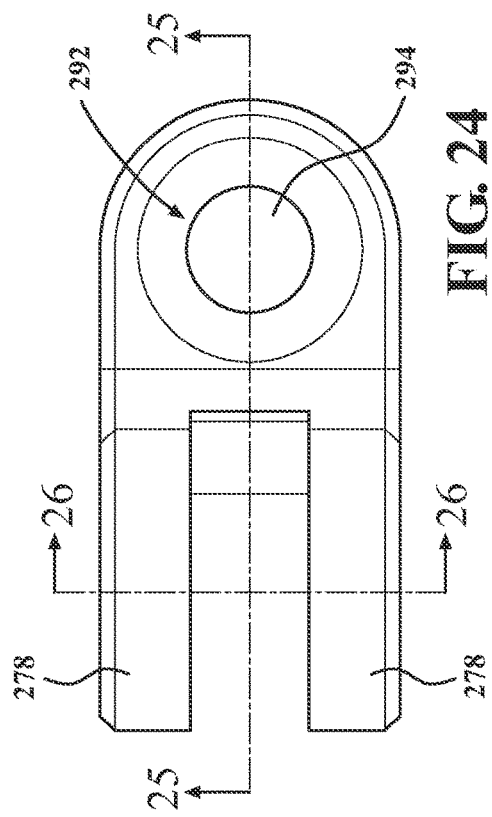
FIG. 24 is a top view of the connector.
Figure 26:
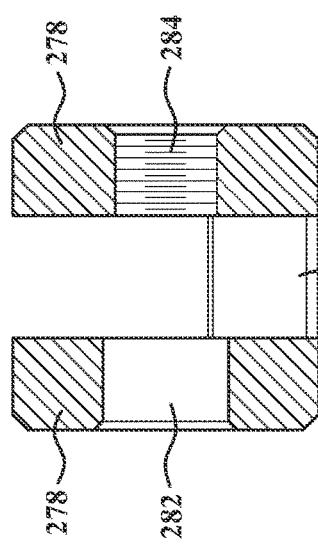
FIG. 26 is a cross-sectional view of the connector taken generally along the line 26-26 in FIG. 24.

Referring to FIG. 22, the tracking head 212 includes the plurality of LEDs 50, gyroscope sensor 60 (not shown), accelerometer 70 (not shown), and a transceiver (not shown) for receiving and transmitting signals to and from the camera unit 36 and/or navigation computer 26. The tracking head 212 may also be connected to the navigation computer 26 via a wired connection as previously described.

The tracking head 212 includes a first hinge member 264 for mounting to the connector assembly 214. The first hinge member 264 defines a non-threaded bore 268.

The connector assembly 214 is shown in FIGS. 4 and 23-26. The connector assembly 214 includes a connector 270 for interconnecting the tracking head 212 and the extension arm 206. The connector 270 includes a pair of second hinge members 278. A space 280 is defined between the second hinge members 278 for receiving the first hinge member 264. One of the second hinge members 278 has a non-threaded bore 282, while the other has a threaded bore 284. A threaded adjustment fastener 286 (see FIG. 4) passes through the non-threaded bore 282 into the threaded bore 284.

When tightening the adjustment fastener 286 the second hinge members 278 are drawn together to compress against the first hinge member 264. This prevents movement of the first hinge member 264 relative to the second hinge members 278. When the adjustment fastener 286 is loosened, the second hinge members 278 relax to a non-compressed position in which the first hinge member 264 is freely movable in the space 280.

The tracking head 212 can be tilted relative to the bone plate 200, 200' via the hinge created by the hinge members 264, 278. Tilting occurs in one degree of freedom about pivot axis P (see FIG. 5). Pivot axis P is defined centrally through the bores 268, 282, 284.

The connector 270 also has a rotational base 290. The rotational base 290 is integral with the second hinge members 278. The rotational base 290 has a flat bottom (not numbered) for mating with the mounting surface 258.

The rotational base 290 defines an opening 292. The opening 292 is shaped to receive a frusto-conical head (not separately numbered) of the adjustment fastener 261 (see FIG. 4). The opening 292 also has a cylindrical bore 294. The bore 294 is shaped so that a threaded shaft (not separately numbered) of the adjustment fastener 261 passes therethrough into the threaded opening 260 in the mounting end 210 of the extension arm 206.

When tightening the adjustment fastener 261 the rotational base 290 is drawn against the mounting surface 258. Friction between the bottom of the rotational base 290 and the mounting surface 258 prevents rotational movement of the connector 270 relative to the mounting surface 258. When the adjustment fastener 261 is loosened, the connector 270 can be rotated freely relative to the mounting surface 258. Thus, the tracking head 212 can be rotated relative to the bone plate 200, 200'. Rotation occurs in one degree of freedom about rotational axis R (see FIGS. 5 and 6). Rotational axis R is defined centrally through bore 294 and threaded opening 260.

Some of the tracking elements, such as the LEDs 50, rely on line-of-sight with the optical sensors 40 to transmit tracking signals to the optical sensors 40. As a result, these tracking elements are also referred to as line-of-sight tracking elements. These tracking elements must be within the field of view of the camera unit 36 and not be blocked from transmitting tracking signals to the camera unit 36. When the signal path of one or more tracking elements is obstructed, an error message, in certain situations, may be generated.

The optical sensors 40 of the navigation system 20 are configured to receive signals from the LEDs 50. The navigation system 20 controls activation of the LEDs 50, as previously described, so that the navigation system 20 can anticipate when a signal should be received. When an anticipated signal from an LED 50 is not received one possibility is that the signal path is obstructed and the signal is blocked from being sent to the camera unit 36. Another possibility is that the LED 50 is not functioning properly.

The navigation computer 26 determines that there is an error if any one of the optical sensors 40 fails to receive a signal from an LED 50, even though other sensors 40 still receive the signal. In other embodiments, navigation computer 26 determines that there is an error if none of the optical sensors 40 receive the signal. In either case, when the navigation system 20 determines that there is an error based on the failure of one or more sensors 40 to receive signals from one or more LEDs 50, an error signal is generated by the navigation computer 26. An error message then appears on displays 28, 29. The navigation computer 26 also transmits an error signal to the tracker controller 62.

Figure 27:
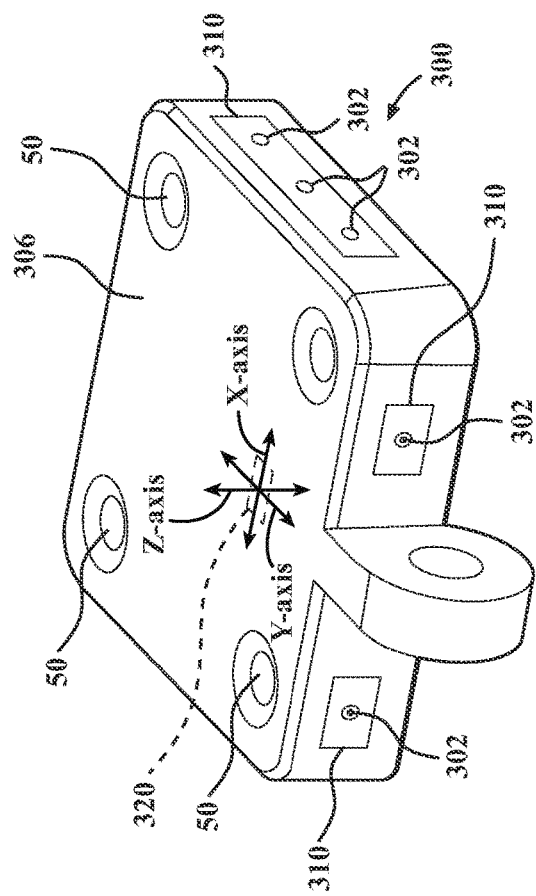
FIG. 27 is a perspective view of an alternative tracking head.

An error indicator 300 is located on tracking head 312 in the embodiment shown in FIG. 27. The tracker controller 62 activates the indicator 300 so that the user is aware of the error, e.g., that the signal from one or more of the LEDs 50 is blocked. Since the navigation computer 26 can determine which specific LED or LEDs 50 has failed to successfully transmit a signal to the optical sensor or sensors 40, in some embodiments each LED 50 on the tracker 44, 46, 48 may have a separate indicator so that the user knows specifically which of the LEDs 50 are blocked.

The indicator 300 includes indicating light emitters such as indicating light emitting diodes (LEDs) 302. The indicating LEDs 302 emit a first colored light when the tracker controller 62 receives the error signal from the navigation computer 26, such as a red, yellow, or orange colored light. The indicating LEDs 302 emit a second colored light when no error signal is received or when an all clear signal is received from the navigation computer 26 after the error is cleared, such as a green or blue colored light. This indicates that the line-of-sight is not broken and is being maintained between at least a required number of the LEDs 50 and the optical sensor or sensors 40. When an error is again detected the light changes from the second colored light to the first colored light. It should be appreciated that the indicating LEDs 302 may include separate indicating LEDs that are alternately activated based on the error status—one or more first colored indicating LEDs for error and one or more second colored indicating LEDs for no error. In other embodiments, the indicator 300 may include an LED or LCD display with error message and/or audible alerts when there is an error.

Tracking head 312 has a body 306 supporting the LEDs 302. The body 306 defines openings (not numbered) covered by transparent windows 310. The LEDs 302 are located inside the body 306 behind the windows 310 so that light from the LEDs 302 can be emitted through the windows 310 so that the light is visible to the user. The windows 310 may also include lenses (not shown) to provide desired lumination characteristics for the LEDs 302.

Figure 29:
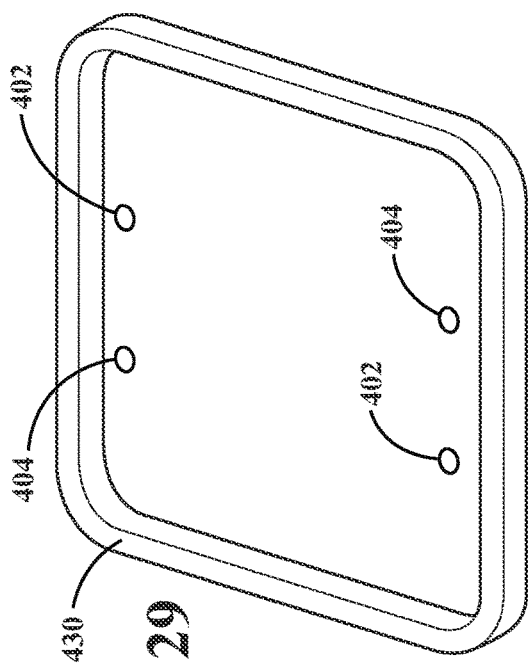
FIG. 29 is a perspective view of a light ring.
Figure 28:
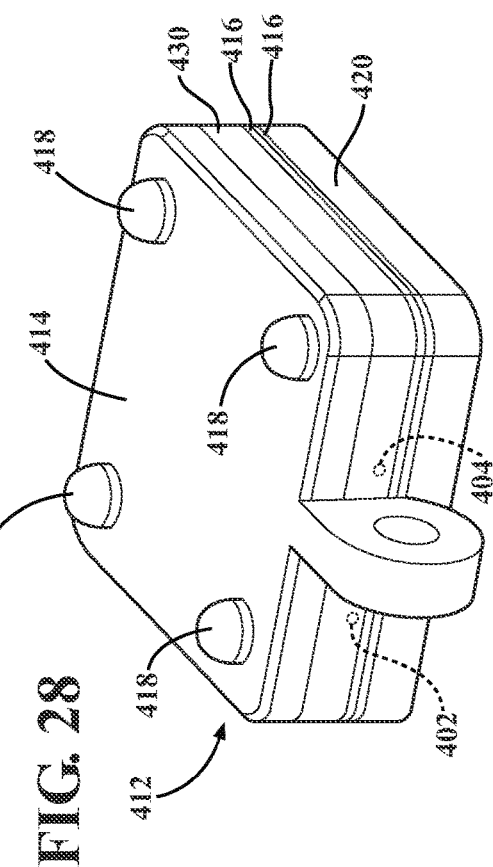
FIG. 28 is a perspective view of yet another alternative tracking head.

In another embodiment shown in FIGS. 28 and 29, tracking head 412 supports first indicator LEDs 402 that emit orange colored light and second indicator LEDs 404 that emit green colored light. The tracking head 412 includes a top 414 supporting the LEDs 50. Sapphire domes 418 cover the LEDs 50. The tracking head 412 further includes a bottom 420.

Figure 30:
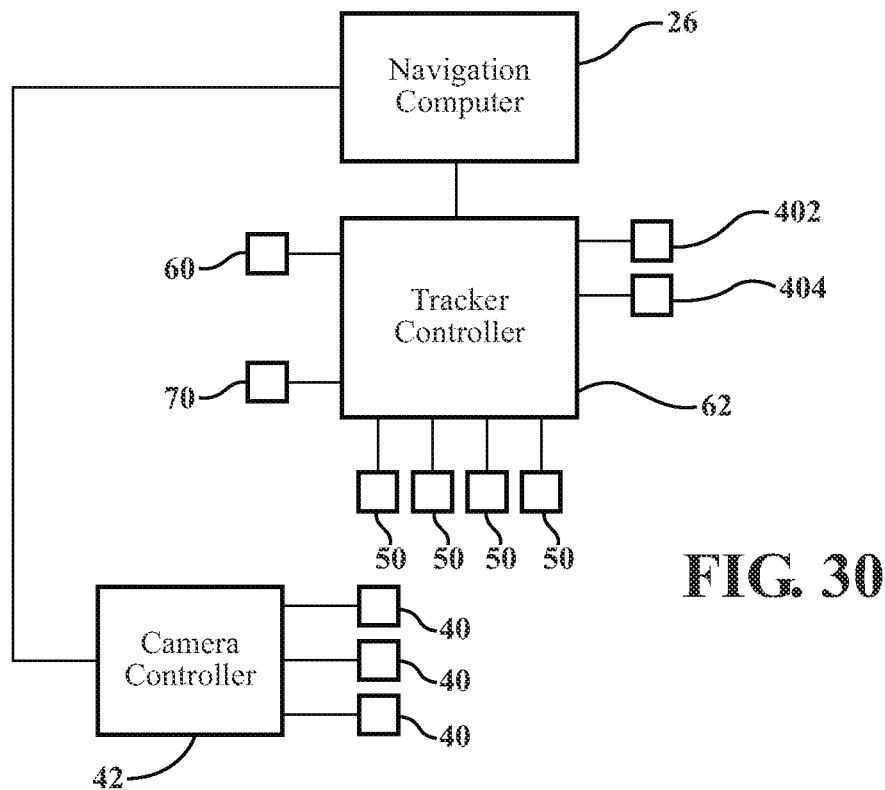
FIG. 30 is a schematic view of the navigation system.

A light ring 430 is captured between the top 414 and bottom 420. The indicator LEDs 402, 404 are located inside the tracking head 412 within the light ring 430, as schematically shown in FIG. 29. The light ring 430 is preferably formed of white alumina material and has a rectangular ring shape. The light ring 430 illuminates either orange or green, depending on which of the indicator LEDs 402, 404 are activated. The indicator LEDs 402, 404 are in electronic communication with the tracker controller 62, as shown in FIG. 30. Weld rings 416 are located between the light ring 430 and the bottom 420 to facilitate assembly.

The light ring 430 is illuminated with the orange colored light from the first indicator LEDs 402 when the tracker controller 62 receives the error signal from the navigation computer 26. The light ring 430 is illuminated with the green colored light from the second indicator LEDs 404 when no error signal is received or when an all clear signal is received from the navigation computer 26 after the error is cleared. When an error is again detected the light ring 430 changes from being illuminated green to being illuminated orange. The indicator LEDs 402, 404 are alternately activated based on the error status—one or more first indicator LEDs 402 are activated for error conditions and one or more second indicator LEDs 404 are activated when no error conditions exist.

Figure 31:
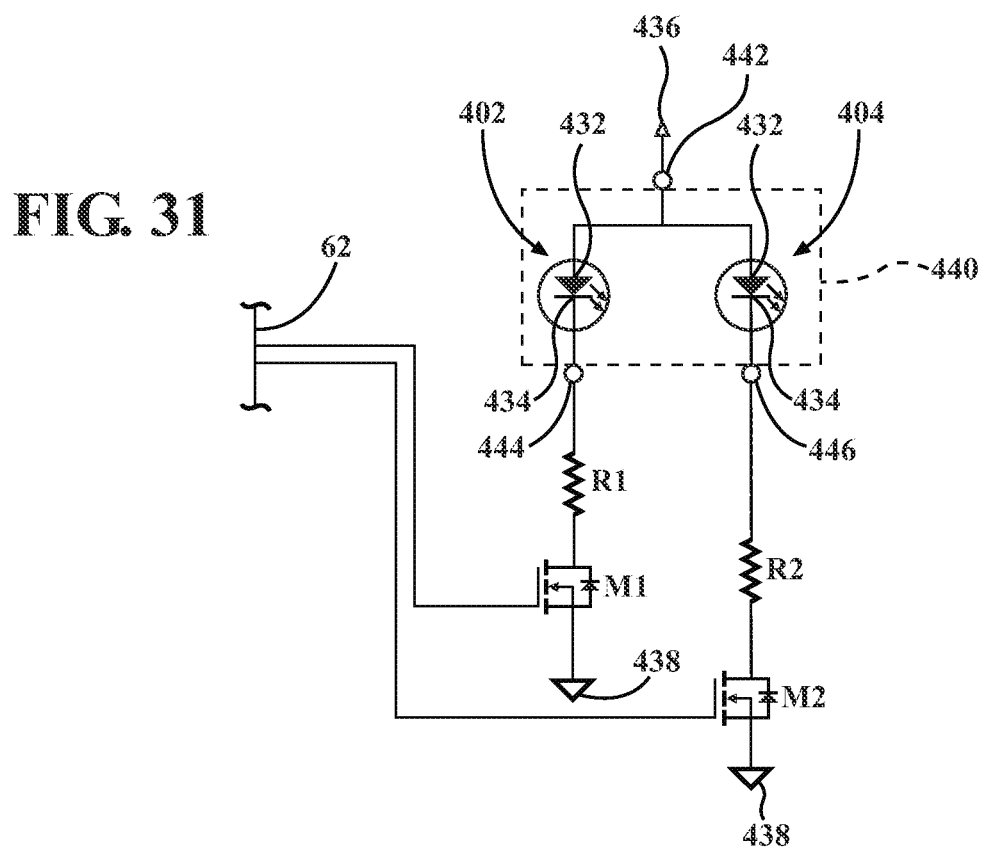
FIG. 31 is an electrical schematic of two indicating LEDs.

Alternating activation of the indicator LEDs 402, 404 are carried out using the circuit shown in FIG. 31. FIG. 31 shows an electrical schematic of the tracker controller 62 and the indicator LEDs 402, 404. The electrical schematic shows the electrical components that facilitate alternating activation/deactivation of the indicator LEDs 402, 404.

Each of the indicator LEDs 402, 404 includes an anode 432 and a cathode 434. In FIG. 31, the anode 432 of each of the indicator LEDs 402, 404 connects to a first voltage reference 436 and the cathode 434 of each of the indicator LEDs 402, 404 connects to a second voltage reference 438. In one embodiment, the first voltage reference 436 is +5 VDC and the second voltage reference 438 is signal ground. The anode 432 of each of the indicator LEDs 402, 404 may connect to the first voltage reference 438 separately, or in combination, as shown in FIG. 31.

Switching elements M1, M2 respectfully connect between the cathodes 434 of the indicator LEDs 402, 404 and the second voltage reference 438. The switching elements M1, M2 control current flow through the indicator LEDs 402, 404 thereby controlling operation of the indicator LEDs 402, 404. The switching elements M1, M2 may be further defined as transistors, and more specifically, N-channel MOSFETs. Each of the MOSFETs M1, M2 includes a gate, source, and drain. The gate of each MOSFET M1, M2 connects to the tracker controller 62. The source of each MOSFET M1, M2 connects to the second reference voltage 438, and more specifically, signal ground. The drain of each MOSFET M1, M2 connects to the cathode 434 of the respective indicator LED 402, 404. Resistors R1, R2 respectfully connect between the cathode 434 of each of the indicator LEDs 402, 404 and the drain of each MOSFET M1, M2. The resistors R1, R2 limit current flow through the indicator LEDs 402, 404 to suitable operating levels.

The tracker controller 62 controls activation/deactivation of the indicator LEDs 402, 404. The tracker controller 62 selectively controls the switching elements M1, M2 to allow or prevent current flow through the indicator LEDs 402, 404.

In one embodiment, the tracker controller 62 sends a first indicator control signal to the gate of the MOSFET M1. The tracker controller 62 may send the first indicator control signal in response to the tracker controller 62 receiving the error signal from the navigation computer 26. The first indicator control signal causes the MOSFET M1 to form a closed circuit path between the source and the drain such that current freely flows through indicator LED 402 between the first and second voltage references 436, 438 to illuminate indicator LED 402.

In other embodiments, the tracker controller 62 sends a second indicator control signal to the gate of the MOSFET M2. The tracker controller 62 may send the second indicator control signal in response to the tracker controller 62 receiving an all clear signal or no error signal from the navigation computer 26. In turn, the second indicator control signal causes the MOSFET M2 to form a closed circuit path between the source and the drain such that current freely flows through indicator LED 404 between the first and second voltage references 436, 438 to illuminate indicator LED 404.

The first and second indicator control signals may correspond to any suitable predetermined voltage or current for controlling MOSFETs M1, M2.

The tracker controller 62 may alternate activation/deactivation of the indicator LEDs 402, 404. In one embodiment, the tracker controller 62 sends the second indicator control signal to the gate of the MOSFET M2 to deactivate indicator LED 404. According to one embodiment, the tracker controller 62 does so during activation of indicator LED 402. To deactivate indicator LED 404, the second indicator control signal causes the MOSFET M2 to form an open circuit between the source and the drain such that current is prevented from flowing through indicator LED 404 between the first and second voltage references 436, 438. Alternatively, the tracker controller 62 may send the first indicator control signal to the gate of the MOSFET M1 to deactivate indicator LED 402 during activation of LED indicator 404.

In one embodiment, the indicator LEDs 402, 404 may be selectively detachable from and attachable to the tracking head 412. The tracking head 412 may include a printed circuit board (PCB) assembly (not shown) disposed therein with the indicator LEDs 402, 404 being electrically connected to the PCB assembly. In FIG. 31, the indicator LEDs 402, 404 are coupled to a unit 440 that is detachable from and attachable to the PCB assembly. For simplicity, the unit 440 is represented in FIG. 31 by a dotted line surrounding indicator LEDs 402, 404. The unit 440 includes a first, second, and third terminal 442, 444, 446 for selectively connecting the indicator LEDs 402, 404 to the PCB assembly. The first terminal 442 selectively connects the anode 432 of each of the indicator LEDs 402, 404 to the first voltage reference 436. The second and third terminals 444, 446 selectively connect the cathode 434 of each of the indicator LEDs 402, 404 to the MOSFETs M1, M2 for each respective indicator LED 402, 404.

Figure 32:
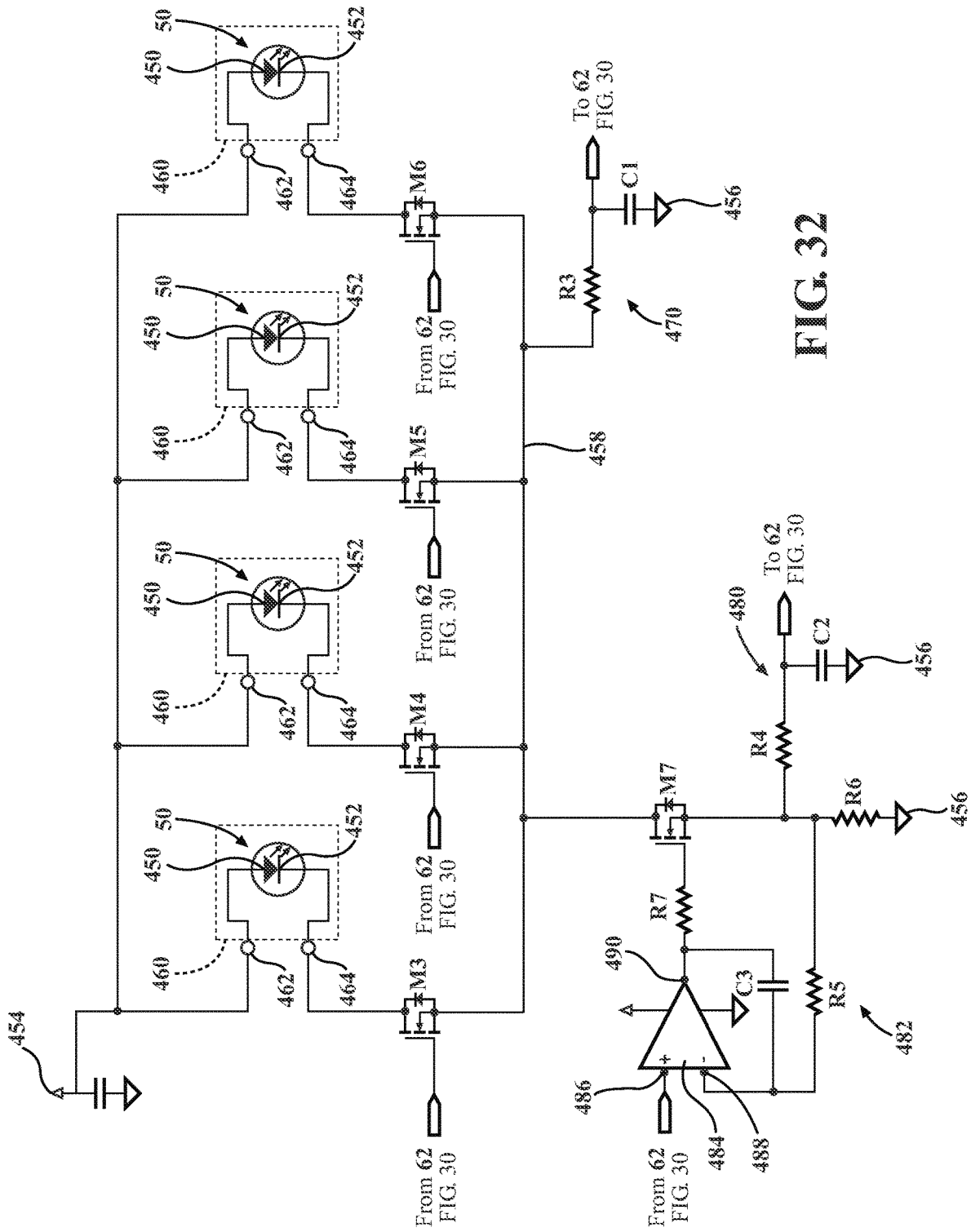
FIG. 32 is an electrical schematic of four tracking LEDs.

Control of the LEDs 50 is carried out using the circuit shown in FIG. 32. FIG. 32 shows an electrical schematic of the LEDs 50 connected to the tracker controller 62. The electrical schematic shows the electrical components that facilitate control of the LEDs 50.

In FIG. 32, each of the LEDs 50 includes an anode 450 and a cathode 452. The anode 450 of each of the LEDs 50 connects to a third voltage reference 454 while the cathode 452 of each of the LEDs 50 connects to a fourth voltage reference 456. In one embodiment, the third voltage reference 454 is +2 VDC and the fourth voltage reference 456 is signal ground. The anode 450 of each of the LEDs 50 may connect to the third voltage reference 454 separately, or in combination, as shown in FIG. 32.

Switching elements M3, M4, M5, M6 respectively connect to the cathodes 452 of the LEDs 50. The switching elements M3, M4, M5, M6 control current flow through the LEDs 50 thereby controlling operation of the LEDs 50. The switching elements M3, M4, M5, M6 may be further defined as transistors, and more specifically, N-channel MOSFETs. Each of the MOSFETs M3, M4, M5, M6 includes a gate, source, and drain. The gate of each MOSFET M3, M4, M5, M6 connects to the tracker controller 62. The source of each MOSFET M3, M4, M5, M6 ultimately connects to the fourth voltage reference 456, and more specifically, signal ground. In FIG. 32, the sources of the MOSFETs M3, M4, M5, M6 are connected to a shared line 458 in a parallel configuration. The drain of each MOSFET M3, M4, M5, M6 respectively connects to the cathode 452 of one of the LEDs 50.

The tracker controller 62 controls activation/deactivation of the LEDs 50. Mainly, the tracker controller 62 selectively controls the switching elements M3, M4, M5, M6 to allow or prevent current flow through the LEDs 50.

In one embodiment, the tracker controller 62 receives an input signal indicating how the tracker controller 62 is to control any given LED 50 or combination of LEDs 50. The tracker controller 62 may receive the input signal from the navigation computer 26. In response, the tracker controller 62 sends an LED control signal to the gate of the MOSFET or MOSFETs M3, M4, M5, M6 connected to any given LED 50 or combination of LEDs 50. In FIG. 32, the tracker controller 62 sends four separate LED control signals and each LED control signal is sent to the gate of each MOSFET M3, M4, M5, M6. In one embodiment, the tracker controller 62 sequentially sends the control signals to the MOSFETs M3, M4, M5, M6 to sequentially control activation or deactivation of the LEDs 50. The tracker controller 62 may send the LED control signals to the MOSFETs M3, M4, M5, M6 for controlling the LEDs 50 according various other configurations, sequences, cycles, or combinations.

If the input signal indicates that the tracker controller 62 is to activate any given LED 50, the tracker controller 62 sends the LED control signal to the gate of the respective MOSFET M3, M4, M5, M6. Doing so causes the MOSFET M3, M4, M5, M6 to form a closed circuit path between the source and the drain of such that current freely flows through the respective LED 50 between the third and fourth voltage references 454, 456 to illuminate the respective LED 50.

If no input signal is received by the tracker controller 62 or when the input signal indicates that the tracker controller 62 is to deactivate any given LED 50, the tracker controller 62 sends the LED control signal to the gate of the MOSFET M3, M4, M5, M6 to deactive the given LED 50. Mainly, the LED control signal causes the MOSFET M3, M4, M5, M6 to form an open circuit between the source and the drain of the MOSFET such that current is prevented from flowing between the third voltage reference 454 and signal ground 456 through the LED 50.

The LEDs 50 may be detachable from and attachable to the tracking head 412. In FIG. 32, each LED 50 is coupled to a unit 460 that is detachable from and attachable to the PCB assembly. For simplicity, each unit 460 is represented in FIG. 32 by a dotted line surrounding each of the LEDs 50. In one embodiment, each unit 460 includes a first and a second terminal 462, 464 for selectively connecting each LED 50 to the PCB assembly. In FIG. 32, the first terminal 462 selectively connects the anode 450 of each LED 50 to the third voltage reference 454. The second terminal 464 selectively connects the cathode 452 of each LED 50 to drain of each respective MOSFET M3, M4, M5, M6.

In FIG. 32, a voltage sensing circuit 470 is provided for measuring operating voltages of any given LED 50 or combination of LEDs 50. The voltage sensing circuit includes a resistor R3 and a capacitor C1 that are arranged as a series RC circuit. The voltage sensing circuit 470 is generally connected between the LEDs 50 and the tracker controller 62. Resistor R3 connects to the sources of the MOSFETs M3, M4, M5, M6 at the shared line 458 and capacitor C1 connects between resistor R3 and the fourth reference voltage 456. In one embodiment, the voltage sensing circuit 470 measures operating voltage of the LEDs 50 between the third and fourth voltage reference 454, 456.

The voltage sensing circuit 470 sends to the tracker controller 62 a voltage sense signal representing a measured operating voltage of the LEDs 50. In one embodiment, the voltage sensing circuit 470 protects the LEDs 50 from inappropriate voltage conditions. The tracker controller 62 may process the voltage sense signal and, in response, modify the LED control signal based on the value of the voltage sense signal. For instance, the tracker controller 62 may change the voltage of the LED control signal(s) if the tracker controller 62 determines that the voltage sense signal is above a predetermined threshold level. In another embodiment, the tracker controller 62 utilizes the voltage sensing circuit 470 for determining whether an LED 50 is malfunctioning. The tracker controller 62 can communicate the malfunction of the LED 50 to the navigation system 20 so that the navigation system 20 can anticipate such malfunction and respond accordingly. The voltage sensing circuit 470 may be implemented according to various other configurations and methods.

In FIG. 32, a current sensing circuit 480 is provided for measuring operating currents of any given LED 50 or combination of LEDs 50. The current sensing circuit 480 protects the LEDs 50 from inappropriate current conditions. The current sensing circuit 480 includes a resistor R4 and a capacitor C2 that are arranged as a series RC circuit. The current sensing circuit 480 is connected generally between the LEDs 50 and the tracker controller 62. Resistor R4 connects to the sources of the MOSFETs M3, M4, M5, M6 at the shared line 458 and capacitor C2 connects between resistor R4 and signal ground 456. In one embodiment, the current sensing circuit 480 measures total operating current of the LEDs passing between the third and fourth voltage reference 454, 456.

In one mode of operation, the current sensing circuit 480 provides to the tracker controller 62 a current sense signal. The current sense signal may be derived from the measured operating current of the LEDs 50. The tracker controller 62 may process the current sense signal and determine whether the current sense signal conforms to a predetermined value. For instance, the tracker controller 62 may determine that the current sense signal is above a predetermined threshold voltage level.

A current limiting circuit 482 is further provided in FIG. 32 for limiting current provided to the LEDs 50. In FIG. 32, the current limiting circuit 482 includes an amplifier 484 for regulating the current through the LEDS 50. The amplifier 484 includes a first and second input terminal 486, 488 and an output terminal 490. The current limiting circuit 482 includes a MOSFET M7 for controlling the current through the LEDs 50. The MOSFET M7 includes a gate, a source, and a drain.

The first input terminal 486 of the amplifier 484 connects to the tracker controller 62. The second input terminal 488 of the amplifier 484 connects to the gate and the source of the MOSFET M7. A capacitor C3 is included between the second input terminal 488 and the gate of the MOSFET M7. A resistor R5 is included between the second input terminal 488 and the source of the MOSFET M7. Resistor R6 connects between the source of the MOSFET M7 and the signal ground 456. The output terminal 490 of the amplifier 484 connects to the gate of the MOSFET M7. Resistor R7 connects between the output 490 of the amplifier 484 and the gate of the MOSFET M7. The drain of the MOSFET M7 connects to the sources of the MOSFETs M3, M4, M5, M6 at the shared line 458.

In one mode of operation, the tracker controller 62 sends a current limiting signal to the current limiting circuit 482. The tracker controller 62 may send the current limiting signal based on the value of the current sense signal provided by the current sensing circuit 480. In FIG. 32, the current limiting signal sent by the tracker controller 62 is received at the first input terminal 486 of the amplifier 484. The amplifier 484 controls the MOSFET M7 based on the current limiting signal received from the tracker controller 62. In one instance, the amplifier 484 deactivates each of the LEDs 50 in response to the current limiting signal. Specifically, the amplifier 484 delivers a signal from the output terminal 490 to the gate of MOSFET M7. Doing so causes MOSFET M7 to form an open circuit between the source and the drain. As such, current is prevented from flowing between the third and fourth voltage reference 454, 456 thereby deactivating each of the LEDs 50. In other embodiments, the amplifier limits current through the LEDs 50, but does not entirely deactivate the LEDs 50, in response to the current limiting signal.

The current sensing circuit 480 and the current limiting circuit 482 may be implemented according to various other configurations and methods.

In some embodiments, the tracker 44 may include four or more tracking LEDs 50 so that if the tracking signal from one of the LEDs 50 is obstructed, position and orientation data can still be obtained from the remaining LEDs 50. In this instance, before any error signals are generated, the navigation computer 26 will first run through a complete tracking cycle. The complete tracking cycle includes sequentially activating all the LEDs 50 on the tracker 44 to determine if the optical sensors 40 receive tracking signals from at least three of the LEDs 50 in the tracking cycle. The error signal is then generated if an optical sensor 40 (or all optical sensors 40 in some embodiments) did not receive tracking signals from at least three LEDs 50 in the tracking cycle.

The navigation system 20 is configured to assist with positioning of the tracker 44 by the surgeon or other medical personnel. This assistance helps to place the tracking head 212 (or tracking heads 312, 412) in a desired orientation that provides line-of-sight between the LEDs 50 and the optical sensors 40 and helps to reduce line-of-sight errors that may otherwise be encountered during a surgical procedure.

Once the bone plate 200, 200' is mounted to the bone, such as femur F, the tracking head 212 is movable relative to the bone plate 200, 200' via the connector assembly 214. In particular, the tracking head 212 is movable about pivot axis P and rotational axis R (see FIG. 4). The connector assembly 214 allows movement of the tracking head 212 in these two degrees of freedom relative to the bone plate 200, 200' to place the tracking head 212 in the desired orientation. This helps to provide the line-of-sight between the LEDs 50 and the optical sensors 40.

Before navigation begins, the medical personnel are instructed to place the tracking head 212 in an initial orientation in which, visually, the tracking head 212 appears to be oriented so that the LEDs 50 will be within the line-of-sight of the optical sensors 40 and unobstructed throughout the surgical procedure. Once the user has placed the tracking head 212 in the initial orientation, the navigation computer 26 provides instructions to the medical personnel setting up the tracker 44 on how to further move the tracking head 212 to reach the desired orientation, if necessary.

The navigation computer 26 first determines the initial orientation of the tracking head 212 and whether the tracking head 212 is already in the desired orientation. If the tracking head 212 is not in the desired orientation, the navigation system 20, through software instructions displayed on displays 28, 29, instructs the user to move the tracking head 212 relative to the bone plate 200, 200' in one or more of the degrees of freedom to reach the desired orientation.

The tracker 44 includes an orientation sensor 320, as shown in FIG. 22. In one embodiment, the orientation sensor 320 is a three-axis gravity sensor 320 configured to measure gravity (acceleration) along three axes, the x-axis, y-axis, and z-axis.

The gravity sensor 320 is located inside the tracking head 212. The gravity sensor 320 is operatively connected to the tracker controller 62. The tracker controller 62 receives gravity measurements from the gravity sensor 320 with respect to the x-axis, y-axis, and z-axis. These signals are analyzed by the navigation system 20 to determine the current orientation of the tracking head 212 relative to gravity. It should be appreciated that the accelerometer 70, in some embodiments, could be used as the gravity sensor 320.

Referring to FIG. 22, the x-axis and y-axis are oriented in a plane of the tracking head 212 that is parallel with a front face of the tracking head 212. The z-axis is oriented perpendicular to the x-axis and y-axis. When the gravity measurement along the z-axis is zero, then gravity is not acting along the z-axis meaning that the x-y plane of the tracking head 212 is oriented vertically.

Figure 33A:
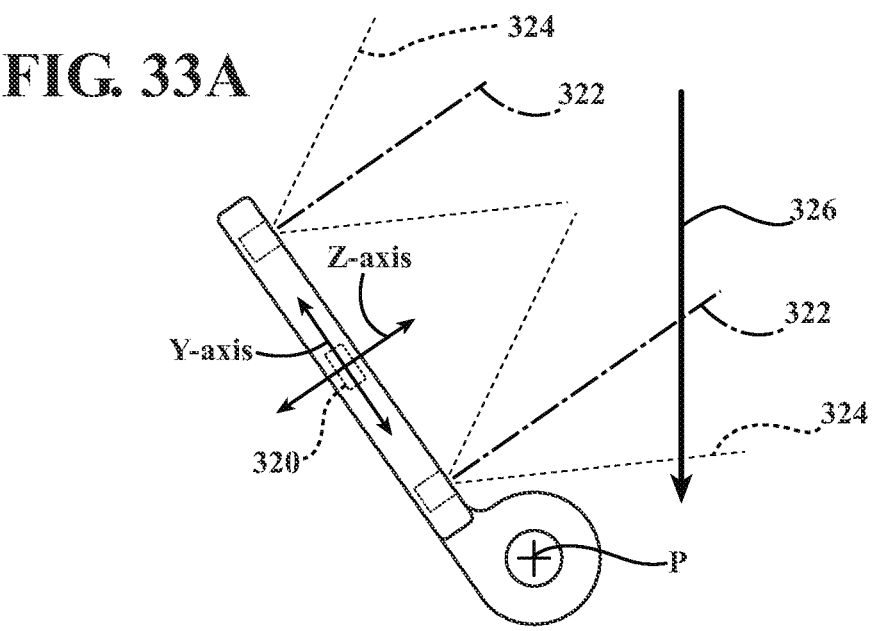
FIGS. 33A and 33B are schematic views of a tracking head in different tilt positions relative to gravity.
Figure 33B:
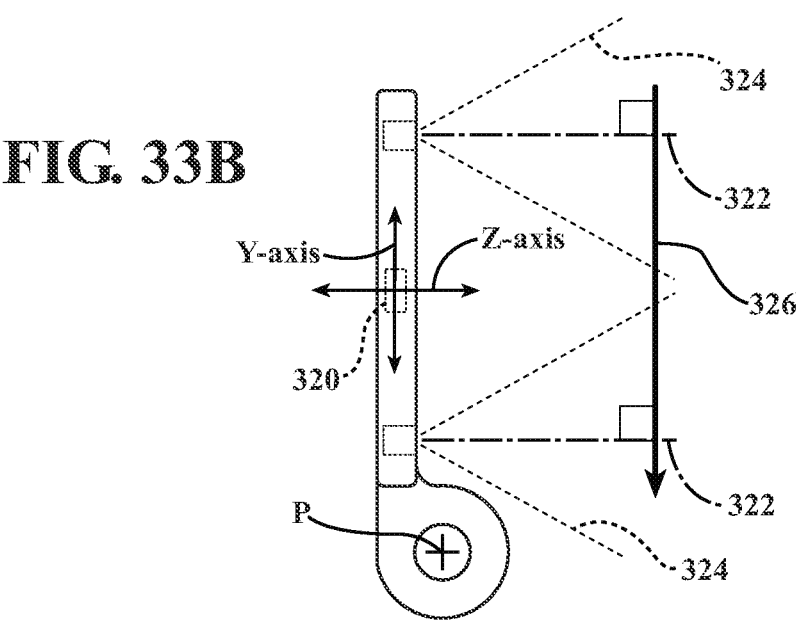

Referring to FIGS. 33A and 33B, in one embodiment, the desired orientation includes having the tilt angle about pivot axis P and the rotational axis R set to angles resulting in the z-axis gravity measurement being zero.

Referring to FIG. 33A, the signals transmitted by the LEDs 50 are considered line-of-sight tracking signals that have a central signal axis 322 defining the center of a signal emitting region 324. The desired orientation is further defined in one embodiment as the central signal axes 322 of the LEDs 50 being perpendicular to the direction of gravity, e.g., perpendicular to a vector 326 oriented in the direction of gravity.

In this embodiment, the navigation computer 26 is configured to instruct the user to adjust the tilt angle of the tracking head 212 until the z-axis gravity measurement is zero. This occurs when the x-y plane of the tracking head 212 is oriented vertically relative to the gravity vector 326, as shown in FIG. 33B.

The instructions to the user to adjust the tilt angle are carried out by the navigation system 20 through displays 28, 29, in which the current orientation of the tracking head 212 is graphically represented. The current orientation is dynamically adjusted as the user changes the tilt angle. The desired orientation of the tracking head 212 is also shown graphically so that the user can visually determine how close the current orientation is to the desired orientation. When the current orientation is at the desired orientation, the displays 28, 29 may flash green or have some other visual indicator that the tracking head 212 is in the desired orientation relative to gravity. It should be appreciated that the desired orientation may include predefined deviations from an ideal orientation in which the x-y plane is perfectly vertical relative to gravity, such as deviations of +/−ten percent, +/−five percent, or +/−two percent.

In alternative embodiments, an LED on the tracking head 212 may indicate to the user when the current orientation is at the desired orientation by being activated to emit a green colored light. Alternatively, an audible indicator may be provided on the tracker 44 to indicate that the tracking head 212 is in the desired orientation.

Once the tilt angle is set so that the tracking head 212 is at the desired orientation relative to gravity (see, e.g., FIG. 33B), the adjustment fastener 286 of the connector assembly 214 is tightened so that the tracking head 212 is unable to tilt relative to the bone plate 200, 200'. In some cases only tilt adjustment of the tracking head 212 may be necessary to place the tracking head 212 in the desired orientation.

In other cases, rotational adjustment about rotational axis R may be needed after the tilt adjustment to place the tracking head 212 in the desired orientation. In these cases, the desired orientation may include an additional rotational adjustment in which the gravity measurement along the z-axis moves from being approximately zero to being non-zero. Adjustment may also be iterative in which tilt adjustment is performed first to place the tracking head 212 vertically, then rotational adjustment is performed which causes the gravity measurement along the z-axis to be non-zero, and then further tilt adjustment is performed to place the z-axis back to approximately zero (i.e., to move the tracking head 212 back to vertical).

During rotational adjustment, the LEDs 50 are being tracked by the optical sensors 40. In particular, the navigation computer 26 is configured to determine, based on the signals received by the optical sensors 40, which rotational orientation of the tracking head 212 provides the best line-of-sight to the LEDs 50.

The desired rotational orientation can be determined by instructing the user to rotate the tracking head 212 through a maximum range of movement, e.g., 360 degrees, one or more times. While the tracking head 212 is rotated, the navigation computer 26 determines at which rotational positions (e.g., rotational angles) about axis R line of sight for each LED 50 is present and at which rotational positions there is no line of sight for each LED 50. This may include rotating the tracking head 212 though its maximum range of movement at various positions of the knee joint, i.e., at the flexed and at the extended positions of the knee joint. This will determine a range of line-of-sight positions about axis R for each LED 50. A best fit algorithm can then be used to determine the positions about axis R that best fits within the ranges of line-of-sight positions for all of the LEDs 50.

Figure 34B:
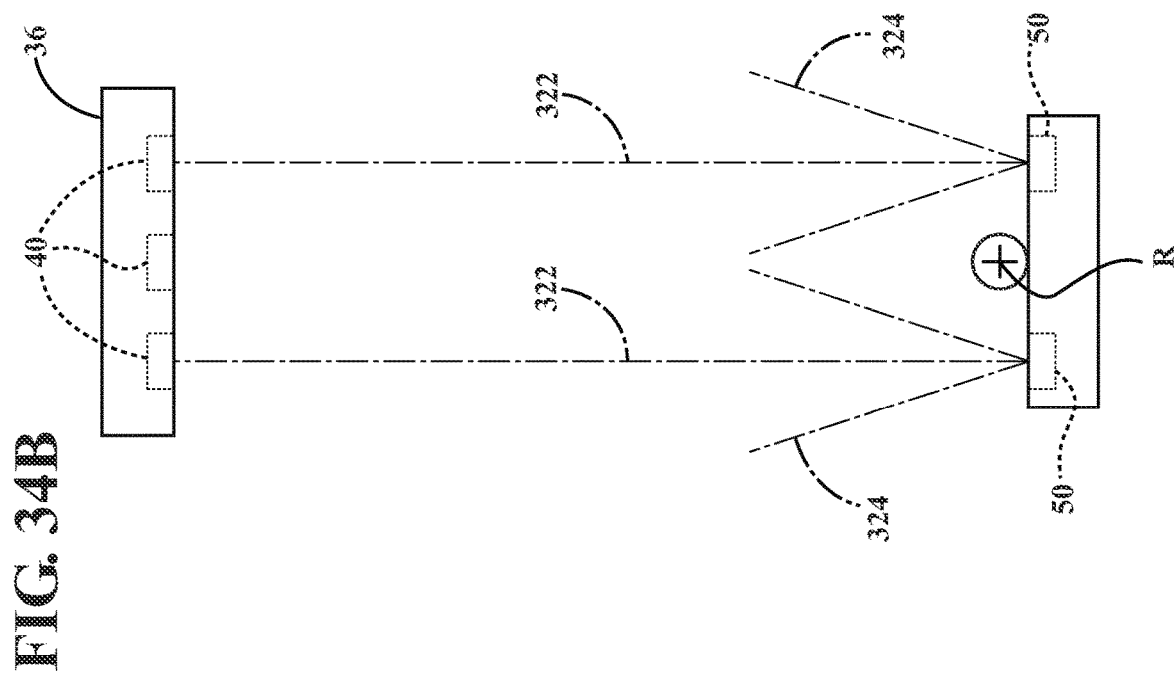
FIGS. 34A and 34B are schematic views of the tracking head in different rotational positions.
Figure 34A:
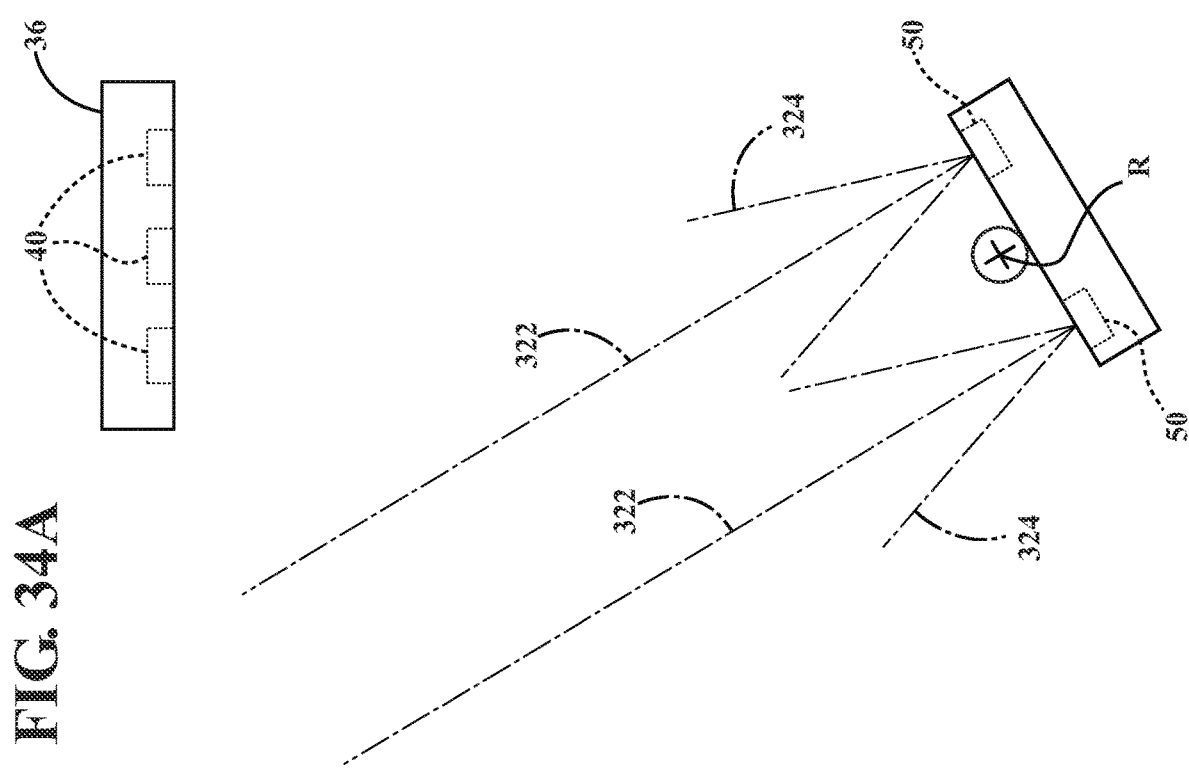
Figure 35:
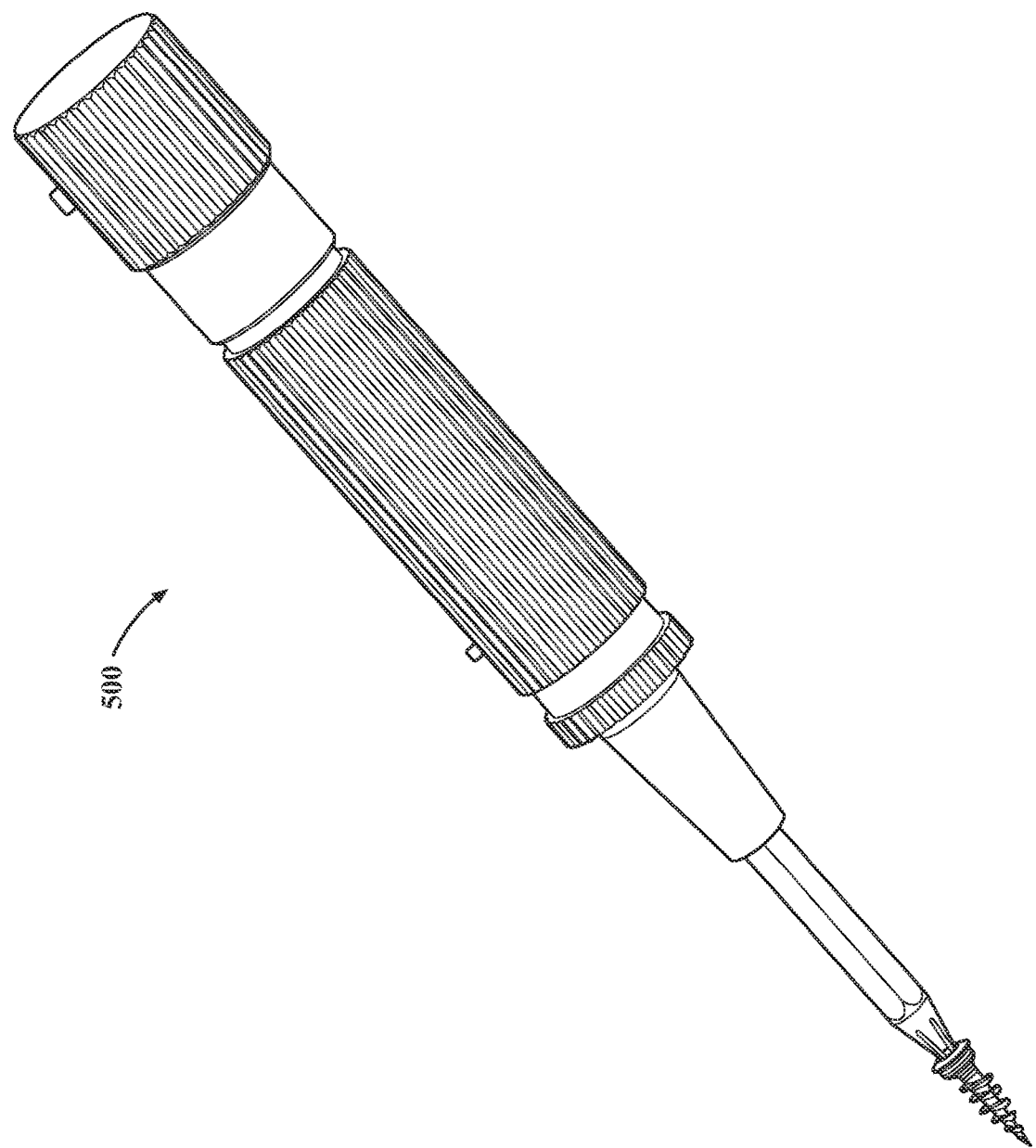
FIG. 35 is a perspective view of a screw driver.

The navigation computer 26 instructs the user, through the displays 28, 29 to rotate the tracking head 212 until the current rotational position meets the desired rotational position determined by the navigation computer 26. See, for instance, the desired rotational position shown in FIG. 34B, as compared to a current rotational position shown in FIG. 34A. Instruction to the user may be accomplished by showing a representation of the current rotational position and the desired rotational position on the displays 28, 29 and dynamically changing the current rotational position as the user makes the adjustment toward the desired rotational position.

Like with adjusting the tilt angle, an LED on the tracking head 212 may indicate to the user when the rotational position is at the desired rotational position by being activated to emit a green colored light. Alternatively, an audible indicator may be provided on the tracker 44 to indicate that the current rotational position is at the desired rotational position. It should be appreciated that the desired rotational position may include predefined deviations from an ideal rotational position, such as deviations of +/−ten percent, +/−five percent, or +/−two percent.

When the desired rotational orientation is met, the adjustment fastener 261 of the connector assembly 214 is tightened so that the tracking head 212 is unable to rotate relative to the bone plate 200, 200'. The tracking head 212 is now fixed from moving relative to the bone plate 200, 200' and the bone.

In some embodiments, the LEDs 50 are being tracked by the optical sensors 40 during adjustment of both the tilt angle and rotational angle. In particular, the navigation computer 26 is configured to determine, based on the signals received by the optical sensors 40, which tilt and rotational orientation of the tracking head 212 provides the best line-of-sight from the LEDs 50 to the optical sensors 40.

In these embodiments, the desired orientation can be determined by instructing the user to tilt and rotate the tracking head 212 through their maximum ranges of movement, one or more times, either sequentially or alternately. While the tracking head 212 is tilted and rotated, the navigation computer 26 determines at which tilt and rotational positions (e.g., tilt and rotational angles) about axes P and R line of sight for each LED 50 is present and at which tilt and rotational positions there is no line of sight for each LED 50. This will determine a range of line-of-sight positions about axes P and R for each LED 50. A best fit algorithm can then be used to determine the positions about axes P and R that best fits within the ranges of line-of-sight positions for all of the LEDs 50.

This process may be iterative and include several adjustments by the user about the axes P and R to find a suitable position for the tracking head 212. In certain instances, the navigation computer 26 may be unable to identify an orientation in which line-of-sight is maintained for all of the LEDs 50 because of a poor initial orientation set by the user. In this case, the navigation computer 26 may first instruct the user to reorient the tracking head 212 so that the LEDs 50 visually appear to be facing the optical sensors 40 and then continue with measuring the orientation of the tracking head 212 through various movements to find the best fit that maintains the line-of-sight for all of the LEDs 50.

In some cases, tilting adjustment may be processed first with the tracking head 212 being moved through its entire range of tilting motion, one or more times, and possibly at multiple knee positions including flexed and extended positions. The best fit tilt angle is then determined and the tilt angle is then fixed at the best fit tilt angle. The tracking head 212 can thereafter be moved through its entire range of rotational motion, one or more times, and possibly at multiple knee positions including flexed and extended positions. The best fit rotational angle is then determined and the rotational angle is then fixed at the best fit rotational angle.

In some embodiments, a third degree of freedom may be adjusted to a desired position, such as a height of the tracker 44. In the embodiment shown only two degrees of freedom are adjusted due to the fact that the tracker 44 moves up and down as the surgeon flexes the knee joint. In this case, the LEDs 50 of the tracking head 212 may be raised or lowered relative to the optical sensors 40 without breaking the line-of-sight between the LEDs 50 and sensors 40.

A screw driver 500 is shown in FIGS. 35-51. The screw driver 500 is used to place the bone screws 202.

Figure 36:
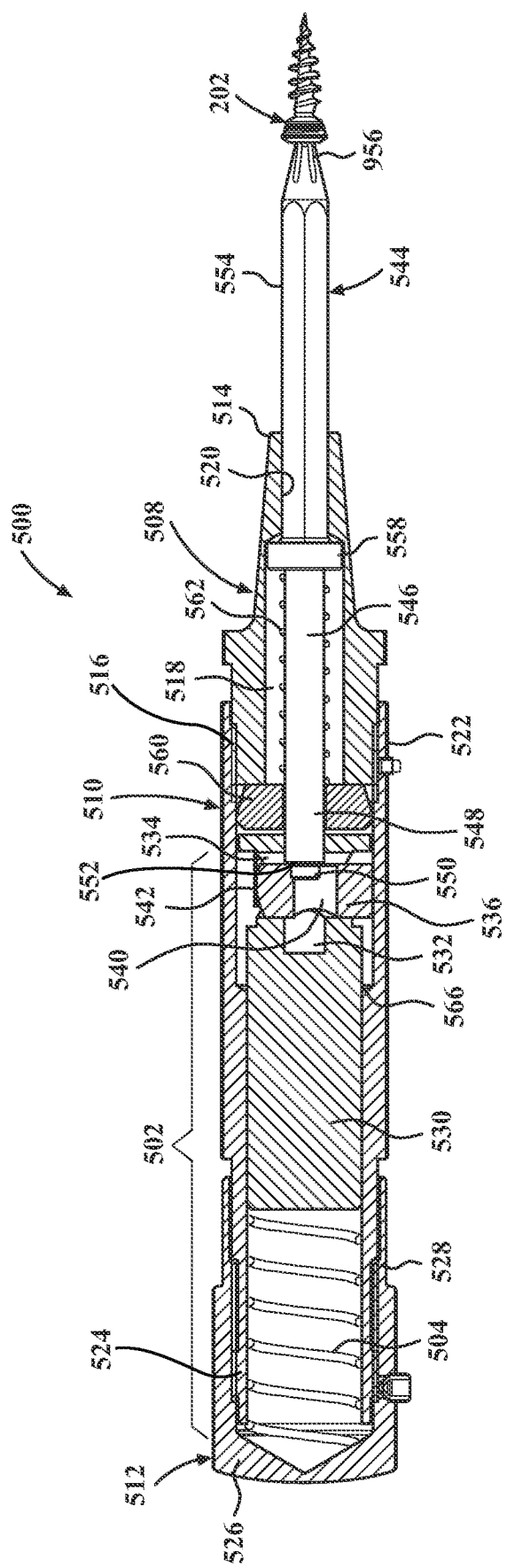
FIG. 36 is a cross-sectional view of the screw driver taken down the center of the screw driver.
Figure 38:
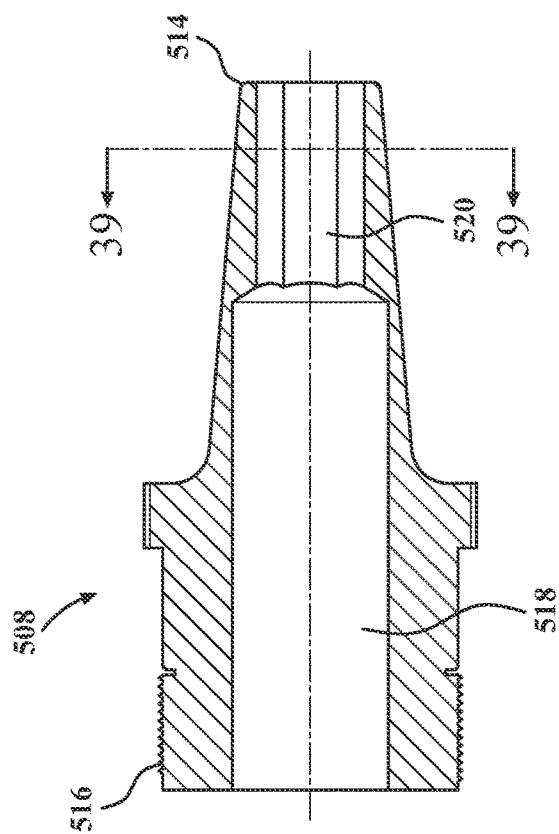
FIG. 38 is a cross-sectional view of the nose tube taken down the center of the nose tube.
Figure 39:
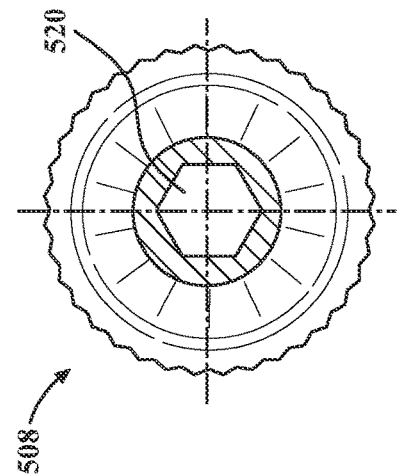
FIG. 39 is a cross-sectional view of the nose tube taken generally along line 39-39 in FIG. 38.
Figure 37:
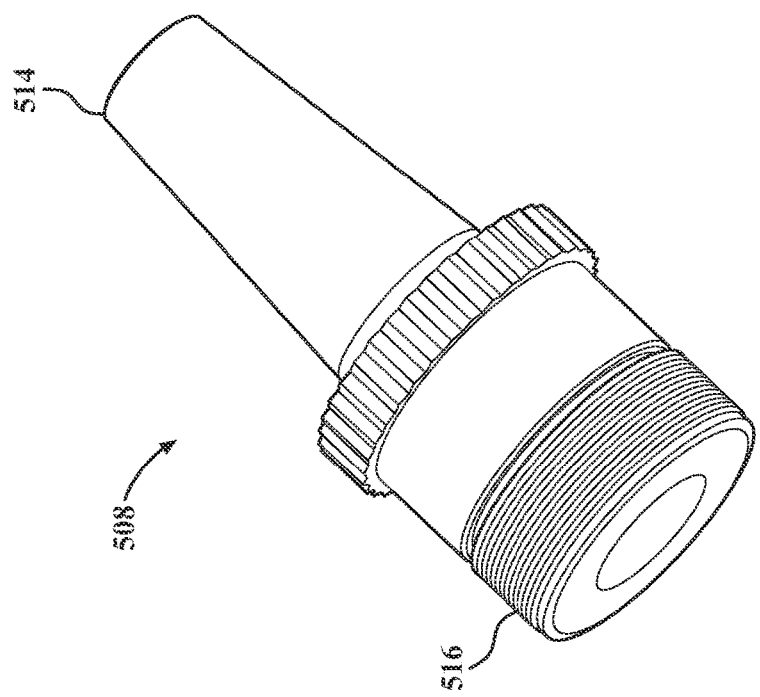
FIG. 37 is a perspective view of a nose tube.
Figures 40, 41:
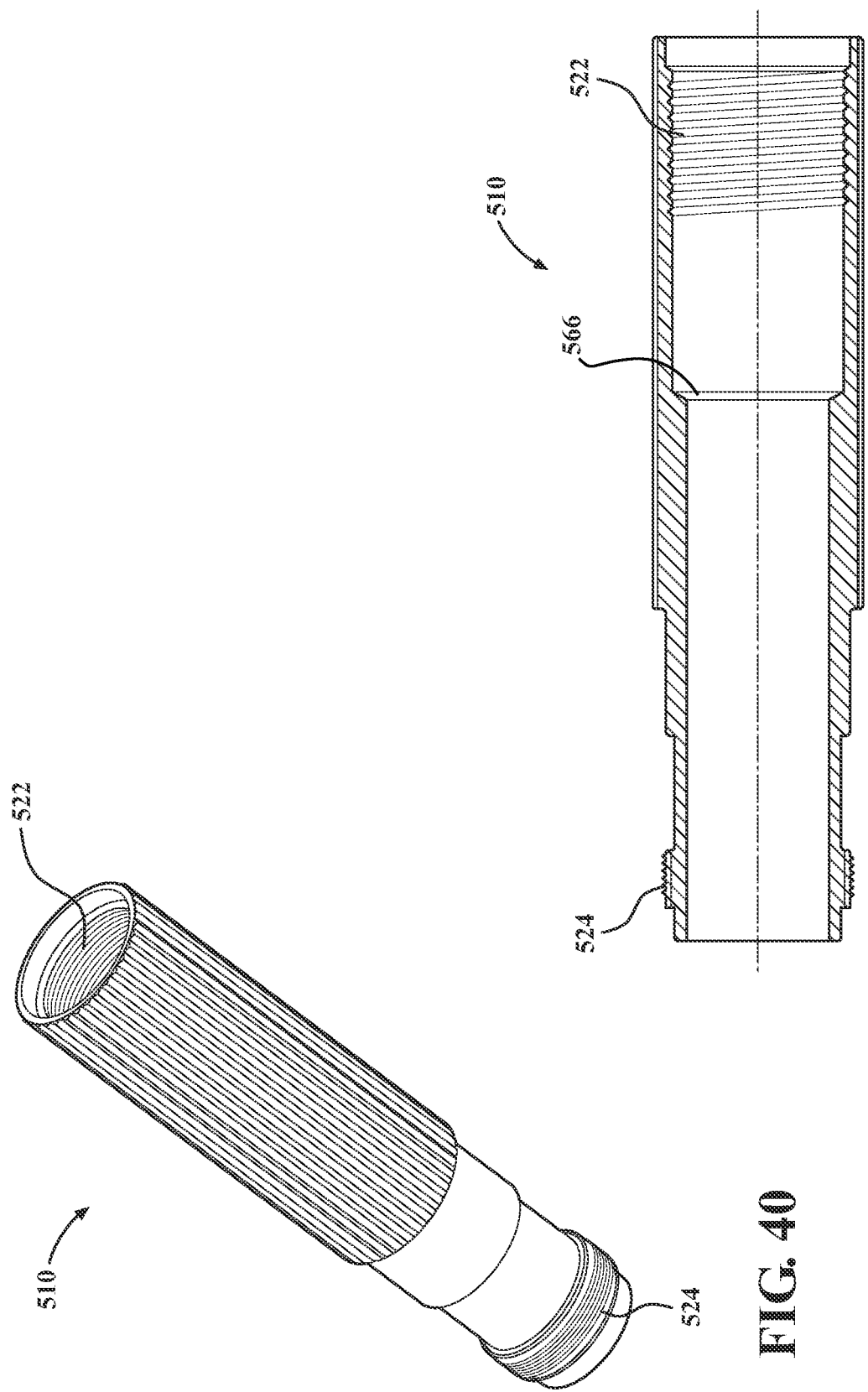
FIG. 40 is a perspective view of a middle tube.
FIG. 41 is a cross-sectional view of the middle tube taken down the center of the middle tube.
Figure 42:
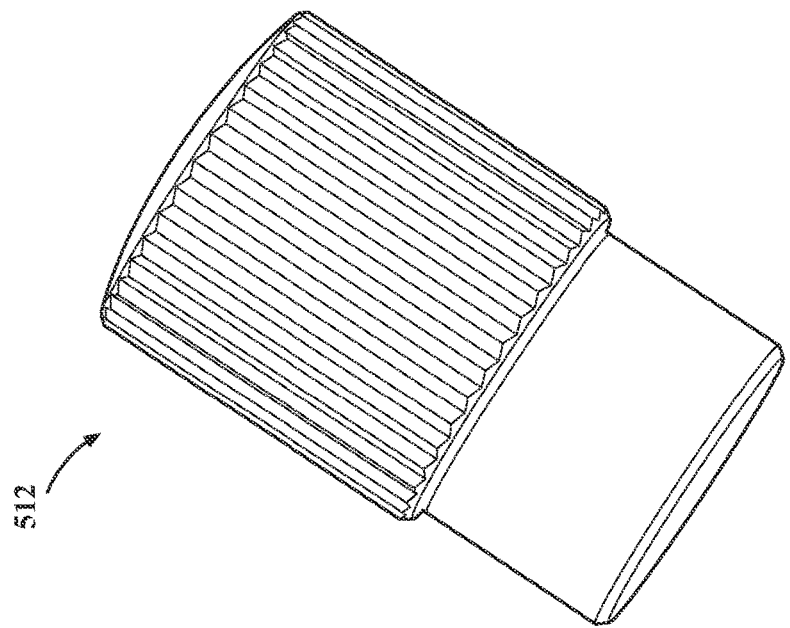
FIG. 42 is a perspective view of a rear cap.
Figure 43:
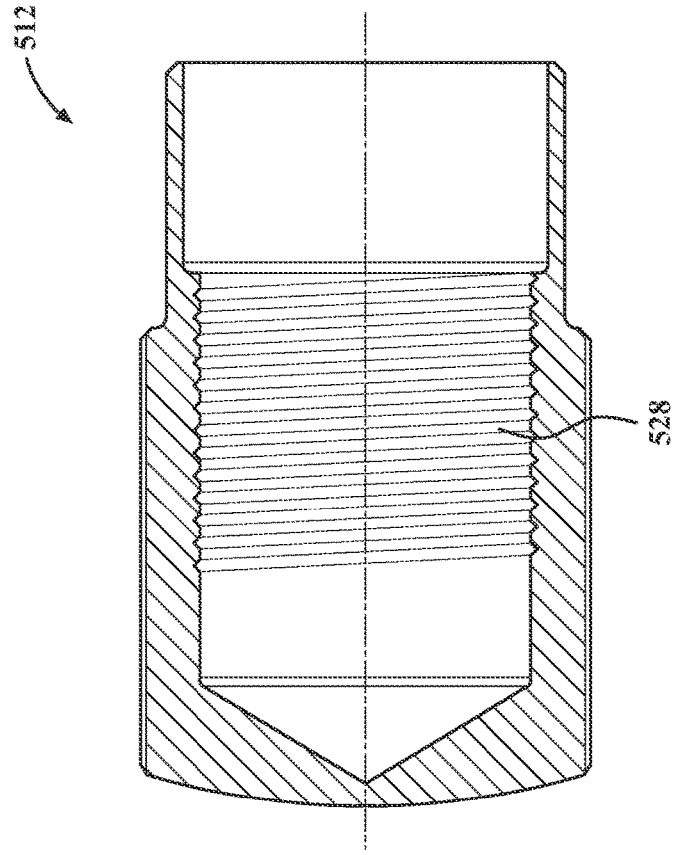
FIG. 43 is a cross-sectional view of the rear cap taken down the center of the rear cap.
Figure 45:
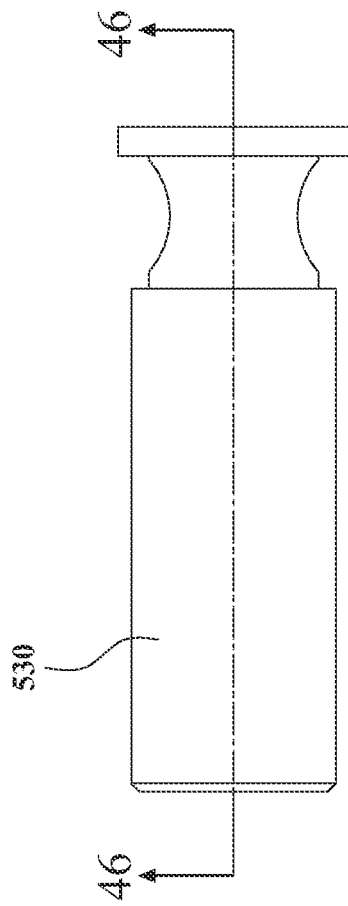
FIG. 45 is an elevational view of the hammer.
Figure 46:
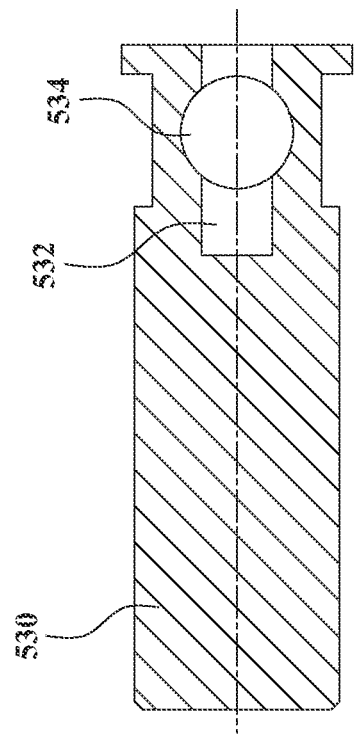
FIG. 46 is a cross-sectional view of the hammer taken generally along the line 46-46 of FIG. 45.
Figure 44:
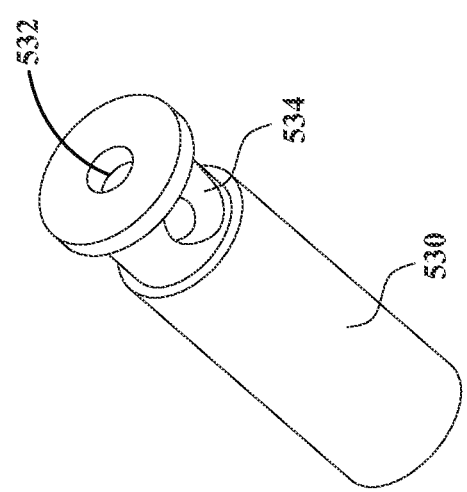
FIG. 44 is a perspective view of a hammer.
Figure 49:
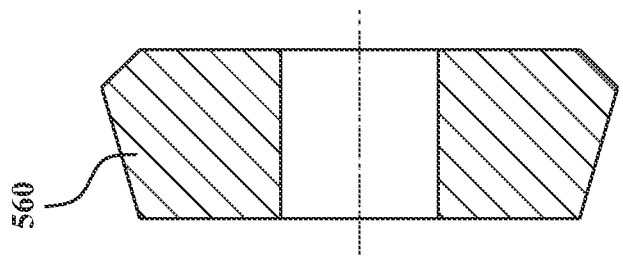
FIG. 49 is a cross-sectional view of a spring cap.
Figure 48:
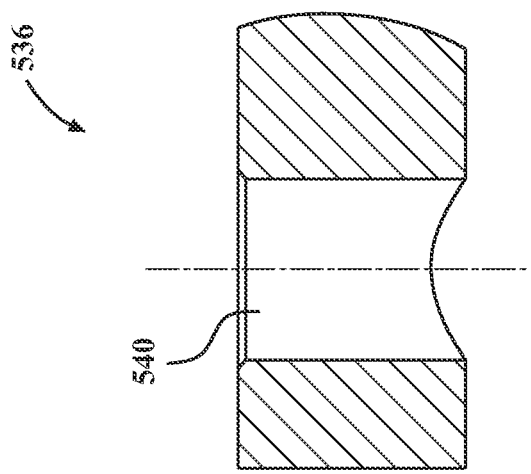
FIG. 48 is a cross-sectional view of the trigger member taken down the center of the trigger member.
Figure 47:
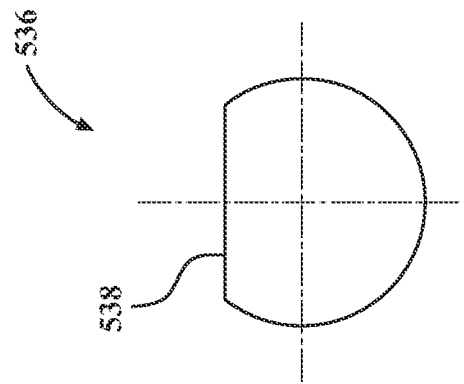
FIG. 47 is an end view of a trigger member.

Referring to FIG. 36, the screw driver 500 includes an integrated impactor 502 that punches each bone screw 202 into the bone prior to screwing. When the screw driver 500 is pressed against the bone screw 202, the impactor 502 stores energy in a rear spring 504. The energy is eventually released as a force that drives the bone screw 202 into the bone. The impactor 502 starts in a rest state in which no energy is stored, is operated to gradually increase the stored energy, and then is actuated to release the energy.

The screw driver 500 includes a body. The body comprises a nose tube 508, middle tube 510, and rear cap 512. The nose tube 508, middle tube 510, and rear cap 512 are separate parts that are releasably connected together for purposes of assembling internal components. It should be appreciated that in other embodiments, the nose tube 508, middle tube 510, and rear cap 512 may be permanently fixed together.

The nose tube 508 has a generally conical distal end 514. The nose tube 508 extends from its distal end 514 to an externally threaded proximal end 516. The nose tube 508 is hollow. The nose tube 508 defines a proximal bore 518 and distal bore 520. The proximal bore 518 is larger in cross-sectional area than the distal bore 520. The proximal bore 518 is circular in cross-section and the distal bore 520 is hexagonal in cross-section.

The middle tube 510 is generally cylindrical. The middle tube 510 has an internally threaded distal end 522 and an externally threaded proximal end 524. The internally threaded distal end 522 threads onto the externally threaded proximal end 516 of the nose tube 508.

The rear cap 512 has a top 526. The rear cap 512 extends distally from the top 526 to an internally threaded section 528. The internally threaded section 528 threads onto the externally threaded proximal end 524 of the middle tube 510.

The impactor 502 includes a hammer 530 disposed in the middle tube 510. The hammer 530 is generally cylindrical in shape. The rear spring 504 is disposed between the rear cap 512 and the hammer 530. The rear spring 504 biases the hammer 530 distally. Compression of the rear spring 504 can be adjusted by loosening or tightening the rear cap 512 to decrease or increase the stored energy of the hammer 530.

A receiving hole 532 is formed in the hammer 530. The receiving hole 532 is disposed about a central axis of the hammer 530. The receiving hole 532 is cylindrically shaped. A cross bore 534 is formed in a direction perpendicular to the receiving hole 532 (see FIG. 46).

The impactor 502 includes a trigger 536 located in the cross bore 534. The trigger 536 is semi-cylindrical in shape. The trigger 536 has a flat bottom 538 (see FIG. 47). A throughbore 540 is defined in the trigger 536. When the impactor 502 is in the rest state, a leaf spring 542 biases the trigger 536 to a position in which the throughbore 540 is offset to the receiving hole 532, i.e., they are misaligned.

A driving rod 544 ultimately receives the energy stored in the impactor 502 to drive in the bone screws 202. The driving rod 544 has a cylindrical shaft 546 with a proximal end 548. The proximal end 548 is shaped for mating reception within the receiving hole 532 of the hammer 530.

Figure 50:
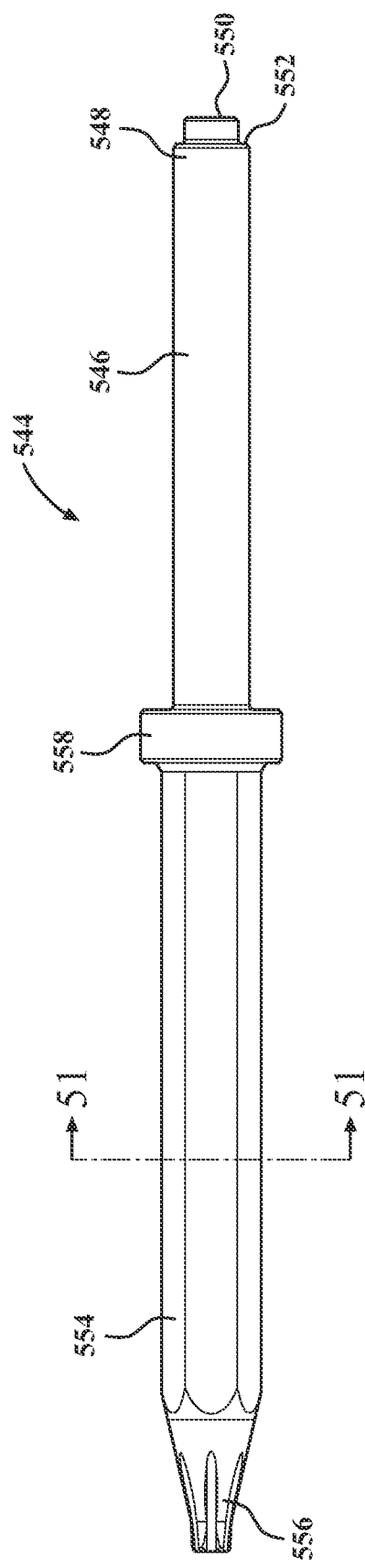
FIG. 50 is an elevational view of a driving rod.
Figure 51:
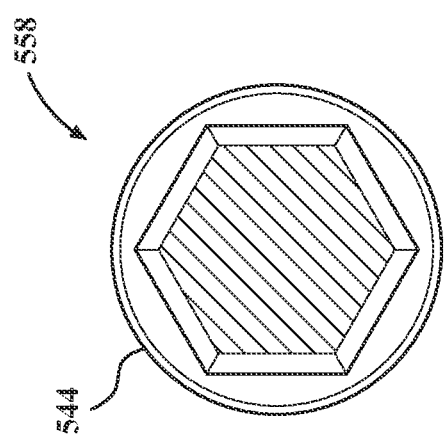
FIG. 51 is a cross-sectional view of the driving rod taken generally along the line 51-51 in FIG. 50.

A boss 550 is located on the proximal end 548 of the driving rod 544 to form a shoulder 552 (see FIG. 50). In the rest state of the impactor 502, the shoulder 552 engages the flat bottom 538 of the trigger 536. In this state, the boss 550 protrudes into the throughbore 540 defined in the trigger 536, but the shoulder 552 prevents the cylindrical shaft 546 from entering the throughbore 540.

The driving rod 544 has a hexagonal shaft 554 with a distal end 556. The hexagonal shaft 554 mates with the hexagonal-shaped distal bore 520 of the nose tube 508 so that rotation of the body by the user also rotates the hexagonal shaft 554. The distal end 556 has features adapted to engage heads of the bone screws 202 to rotate and drive the bone screws 202 into the bone when the body of the screw driver 500 is rotated.

A collar 558 is fixed to the hexagonal shaft 554. The collar 558 prevents the driving rod 544 from falling out of the nose tube 508. The collar 558 is cylindrical in shape to mate with the proximal bore 518 of the nose tube 508.

A spring cap 560 is centrally disposed inside the middle tube 510 between the nose tube 508 and the hammer 530. The spring cap 560 is press fit inside the middle tube 510.

A rod spring 562 is disposed about the cylindrical shaft 546 of the driving rod 544. The rod spring 562 acts between the spring cap 560 and the collar 558 of the driving rod 544 to return the screw driver 500 to the rest state after the hammer 530 is actuated. The spring cap 560 defines a throughbore (not numbered) for receiving the cylindrical shaft 546 of the driving rod 544 and centering the cylindrical shaft 546 inside the middle tube 510.

The screw driver 500 is pressed against the bone screw 202 by gripping the rear cap 512 and/or middle tube 510 and urging them distally. The bone screw 202 is thus pressed against the bone. At the same time, the driving rod 544 travels proximally in the middle tube 510. The shoulder 552 pushes the trigger 536 proximally while the leaf spring 542 keeps the trigger 536 throughbore 540 misaligned with the receiving hole 532 of the hammer 530.

The middle tube 510 includes an inclined inner surface 566. The inclined inner surface 566 engages the trigger 536 when the trigger 536 reaches the inclined inner surface 566. When this occurs, the inclined inner surface 566 acts like a cam to push the trigger 536 in a manner that centers the throughbore 540 of the trigger 536 and places the throughbore 540 into alignment with the receiving hole 532 of the hammer 530. Likewise, the proximal end 548 of the driving rod 544 is now aligned to fit within the throughbore 540, which allows the trigger 536 to slide down the driving rod 544 thereby releasing the hammer 530. The hammer 530 then moves forward, propelled by the rear spring 504.

Because the receiving hole 532 in the hammer 530 has a predefined depth, the boss 550 on the proximal end 548 of the driving rod 544 eventually bottoms out in the receiving hole 532 and the force of the hammer 530 is transmitted into the driving rod 544 and the bone screw 202 punching the bone screw 202 into the bone.

OTHER EMBODIMENTS

In one embodiment, when each of the trackers 44, 46, 48 are being actively tracked, the firing of the LEDs occurs such that one LED 50 from tracker 44 is fired, then one LED 50 from tracker 46, then one LED 50 from tracker 48, then a second LED 50 from tracker 44, then a second LED 50 from tracker 46, and so on until all LEDs 50 have been fired and then the sequence repeats. This order of firing may occur through instruction signals sent from the transceivers (not shown) on the camera unit 36 to transceivers (not shown) on the trackers 44, 46, 48 or through wired connections from the navigation computer 26 to the tracker controller 62 on each of the trackers 44, 46, 48.

The navigation system 20 can be used in a closed loop manner to control surgical procedures carried out by surgical cutting instruments. Both the instrument 22 and the anatomy being cut are outfitted with trackers 50 such that the navigation system 20 can track the position and orientation of the instrument 22 and the anatomy being cut, such as bone.

In one embodiment, the navigation system 20 is part of a robotic surgical system for treating tissue. In some versions, the robotic surgical system is a robotic surgical cutting system for cutting away material from a patient's anatomy, such as bone or soft tissue. The cutting system could be used to prepare bone for surgical implants such as hip and knee implants, including unicompartmental, bicompartmental, or total knee implants. Some of these types of implants are shown in U.S. patent application Ser. No. 13/530,527, entitled, "Prosthetic Implant and Method of Implantation", the disclosure of which is hereby incorporated by reference.

In one embodiment, the navigation system 20 communicates with a robotic control system (which can include the manipulator controller 54). The navigation system 20 communicates position and/or orientation data to the robotic control system. The position and/or orientation data is indicative of a position and/or orientation of instrument 22 relative to the anatomy. This communication provides closed loop control to control cutting of the anatomy such that the cutting occurs within a predefined boundary.

In one embodiment, each of the femur F and tibia T has a target volume of material that is to be removed by the working end of the surgical instrument 22. The target volumes are defined by one or more boundaries. The boundaries define the surfaces of the bone that should remain after the procedure. In some embodiments, navigation system 20 tracks and controls the surgical instrument 22 to ensure that the working end, e.g., bur, only removes the target volume of material and does not extend beyond the boundary, as disclosed in U.S. patent application Ser. No. 13/958,070, filed Aug. 2, 2013, entitled, "Surgical Manipulator Capable of Controlling a Surgical Instrument in Multiple Modes", the disclosure of which is hereby incorporated by reference.

Several embodiments have been discussed in the foregoing description. However, the embodiments discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. A plate for attaching to an anatomic structure with one or more fasteners, the plate comprising:
    a body comprising at least three corners, a top surface, and a bottom surface opposite the top surface, the body defining one or more openings configured to receive a respective one of the one or more fasteners, wherein the bottom surface is concave to define a space configured to accommodate a portion of the anatomic structure;
    at least three bone pad surfaces, with each bone pad surface extending from the bottom surface of one of the corners; and
    at least three spikes, with each spike extending away from one of the bone pad surfaces.

2. The plate of claim 1, wherein a boundary is defined at a location in which an edge of at least one bone pad surface transitions to the bottom surface, and wherein the edge of the at least one bone pad surface is angled or curved at the boundary.

3. The plate of claim 1, wherein at least one bone pad surface is configured to be oriented substantially parallel to a portion of the anatomic structure to which the at least one bone pad surface is configured to contact.

4. The plate of claim 1, wherein at least one spike comprises a base and the bone pad surface from which the at least one spike extends completely surrounds the base.

5. The plate of claim 1, wherein at least one spike comprises a base and the bone pad surface from which the at least one spike extends partially surrounds the base.

6. The plate of claim 1, wherein at least one spike is coupled to the bottom surface of the body and the at least one spike extends through the bone pad surface from which the at least one spike extends.

7. The plate of claim 1, wherein at least one spike is integrally formed with the bone pad surface.

8. The plate of claim 1, wherein at least one spike is fastened to the bone pad surface.

9. The plate of claim 1, wherein the body further comprises a peripheral edge extending between the top surface and the bottom surface, wherein at least one bone pad surface extends to the peripheral edge.

10. A surgical tracking assembly, comprising:
    a tracking head;
    an extension arm comprising a mounting end and a base end, and the tracking head being coupled to the extension arm at the mounting end; and
    a plate coupled to the extension arm at the base end, the plate configured for attachment to an anatomic structure with one or more fasteners, the plate comprising:

a body comprising at least three corners, a top surface, and a bottom surface opposite the top surface, the body defining one or more openings configured to receive a respective one of the one or more fasteners, wherein the bottom surface is concave to define a space configured to accommodate a portion of the anatomic structure;

at least three bone pad surfaces, with each bone pad surface extending from the bottom surface of one of the corners; and at least three spikes, with each spike extending away from one of the bone pad surfaces.

11. The surgical tracking assembly of claim 10, wherein the tracking head comprises optical tracking elements.

12. The surgical tracking assembly of claim 11, wherein the optical tracking elements are passive tracking elements.

13. The surgical tracking assembly of claim 11, wherein the optical tracking elements are active tracking elements.

14. The surgical tracking assembly of claim 10, wherein the tracking head comprises one or both of: a gyroscope sensor and an accelerometer.

15. The surgical tracking assembly of claim 10, wherein at least one spike comprises a base and the bone pad surface from which the at least one spike extends completely surrounds the base.

16. The surgical tracking assembly of claim 10, wherein at least one spike is coupled to the bottom surface of the body and the at least one spike extends through the bone pad surface from which the at least one spike extends.

17. The surgical tracking assembly of claim 10, wherein at least one spike is integrally formed with the bone pad surface from which the at least one spike extends.

18. The surgical tracking assembly of claim 10, wherein the body further comprises a peripheral edge extending between the top surface and the bottom surface, wherein at least one bone pad surface extends to the peripheral edge.

* * * * *